(12) United States Patent
Zhang et al.

(10) Patent No.: US 9,340,810 B2
(45) Date of Patent: May 17, 2016

(54) POLYPEPTIDES HAVING CELLULOLYTIC ENHANCING ACTIVITY AND POLYNUCLEOTIDES ENCODING SAME

(75) Inventors: Yu Zhang, Beijing (CN); Lan Tang, Beijing (CN); Svend Hostgaard Bang Henriksen, Aalborg (DK)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 14/006,021

(22) PCT Filed: Apr. 25, 2012

(86) PCT No.: PCT/CN2012/074673
§ 371 (c)(1),
(2), (4) Date: Sep. 18, 2013

(87) PCT Pub. No.: WO2012/146171
PCT Pub. Date: Nov. 1, 2012

(65) Prior Publication Data
US 2014/0026261 A1   Jan. 23, 2014

Related U.S. Application Data

(60) Provisional application No. 61/485,358, filed on May 12, 2011.

(30) Foreign Application Priority Data

Apr. 25, 2011   (WO) ............... PCT/CN2011/073275

(51) Int. Cl.
*C12P 19/14*   (2006.01)
*C07K 14/37*   (2006.01)
*C12P 19/02*   (2006.01)
*C12N 15/82*   (2006.01)

(52) U.S. Cl.
CPC ............... *C12P 19/14* (2013.01); *C07K 14/37* (2013.01); *C12P 19/02* (2013.01); *C12N 15/82* (2013.01); *C12P 2203/00* (2013.01)

(58) Field of Classification Search
None
See application file for complete search history.

(56) References Cited

U.S. PATENT DOCUMENTS

| | | |
|---|---|---|
| 2010/0143971 A1 | 6/2010 | Spodsberg et al. |
| 2011/0010805 A1 | 1/2011 | Duan et al. |

FOREIGN PATENT DOCUMENTS

| | | | |
|---|---|---|---|
| WO | 2004/031378 | A2 | 4/2004 |
| WO | 2005/074647 | A2 | 8/2005 |
| WO | 2005/074656 | A2 | 8/2005 |
| WO | 2007/089290 | A2 | 8/2007 |
| WO | 2008/148131 | A1 | 12/2008 |
| WO | 2008/151043 | A1 | 12/2008 |
| WO | 2009/085859 | A2 | 7/2009 |
| WO | 2009/085864 | A2 | 7/2009 |
| WO | 2009/085868 | A1 | 7/2009 |
| WO | 2009/085935 | A2 | 7/2009 |
| WO | 2010/065830 | A1 | 6/2010 |
| WO | 2010/138754 | A2 | 12/2010 |
| WO | 2011/005867 | A1 | 1/2011 |
| WO | 2011/035027 | A2 | 3/2011 |
| WO | 2011/039319 | A1 | 4/2011 |
| WO | 2011/041397 | A1 | 4/2011 |
| WO | 2011/041504 | A1 | 4/2011 |

OTHER PUBLICATIONS

Uniprot. Putative uncharacterized protein. 2006. Accession Q2GWR1.*
Uniprot. Function: Enzyme of T. reesei is involved in degradation of polysaccharides. 2007. Accession A2R5J9.*
Guo et al. Protein tolerance to random amino acid change. 2004. PNAS. 101(25):9205-9210.*
Koseki et al. Biochemical charaacterization of a glycoside hydrolase family 61 endoglucanase from Aspergillus kawachii. 2008. Appl. Microbiol. Biotechnol. 77:1279-1285.*
Hemsworth et al, Jun. 14, 2013, Current Opinion in Structural Biology, vol. 23, pp. 660-668.*
Levasseur et al, 2013, Biochechnology for Biofuels, pp. 1-14.*
Morgenstern et al, Sep. 12, 2014.*
Anonymous, Genbank Accession No. EAA30263 (2007).
Birren et al., Genbank Accession No. XP_001219904 (2008).
Birren et al., Genbank Accession No. XP_001220412 (2008).
Birren et al., Genbank Accession No. XP_001223687 (2008).
Birren et al., Genbank Accession No. XP_001224181 (2008).
Birren et al, Genbank Accession No. XP_001225249 (2008).
Birren et al,, Genbank Accession No. XP_001225930 (2008).
Birren et al., Genbank Accession No. XP_001227508 (2008).
Birren et al., Genbank Accession No. XP_001227732 (2008).
Birren et al., Genbank Accession No. EAQ88348 (2010).
Coleman et al., Genbank Accession No. XP_003046131 (2010).
Espagne et al., Genbank Accession No. XP_001903701 (2008).
Espagne et al., Genbank Accession No. XP_001905203 (2010).
Espagne et al., Genbank Accession No. XP_001905612 (2010).
Espagne et al., Genbank Accession No. XP_001905623 (2010).
Espagne et al., Genbank Accession No. XP_001905728 (2010).
Espagne et al., Genbank Accession No. XP_001906078 (2010).
Espagne et al., Genbank Accession No. XP_001906795 (2010).
Espagne et al., Genbank Accession No. XP_001906810 (2010).

(Continued)

*Primary Examiner* — Eileen B O Hara
(74) *Attorney, Agent, or Firm* — Robert L. Starnes

(57) ABSTRACT

The present invention provides isolated polypeptides having cellulolytic enhancing activity and isolated polynucleotides encoding the polypeptides. The invention also provides nucleic acid constructs, vectors, and host cells comprising the polynucleotides as well as methods of producing and using the polypeptides.

62 Claims, 28 Drawing Sheets

(56) References Cited

OTHER PUBLICATIONS

Espagne et al, Genbank Accesssion No. XP_001907069 (2010).
Espagne et al., Genbank Accession No. XP_001907502 (2010).
Espagne et al., Genbank Accession No. XP_001907637 (2010).
Espagne et al., Genbank Accession No. XP_001907702 (2010).
Espagne et al., Genbank Accession No. XP_001907679 (2010).
Galagan et al., Genbank Accession No. XP_962644 (2008).
Galagan et al., Genbank Accession No. XP_965498 (2008).
Schulein et al., Journal of Biotechnology, vol. 57, No. 1-3, pp. 71-81 (1998).
Shulte et al., Genbank Accession No. CAD21296 (2006).
Harris et al, 2010, Biochem 49 (15), 3305-3316.

* cited by examiner

```
seq1>
         M  K  L  S  V  V  L  T  G  L  A  A  A  L  A  E  A  H  Y
     1   atgaagctcagcgttgtcctcacaggcctggcggcagccctcgccgaggctcattGTCAG
                                                                  T  F
    61   TCCATACGACAGCGAAACCCCTGGATGATCACGAGACTAACCAGTCCTACCAGacacctt
         P  S  V  G  N  T  A  D  W  Q  V  V  R  Q  T  T  N  F  Q  S
   121   ccccagcgtcggcaacaccgccgactggcaggtcgtgcgccagacgaccaacttccagag
         N  G  P  V  T  D  V  N  S  D  Q  I  R  C  Y  E  R  F  P  G
   181   caacggccccgtgacggacgtcaactcggaccagatccggtgctacgagcgcttccccgg
         Q  G  A  P  G  I  Y  N  V  T  A  G  Q  T  I  S  Y  N  A  K
   241   ccaggggggcgcccggcatctacaacgtcaccgccggccagaccatctcgtacaacgccaa
         A  S  I  S  H  P  G  P  M  A  F  Y  I  A  K  V  P  A  G  Y
   301   ggcctctatctcccacccgggccccatggccttctacatcgccaaggtccctgccggcta
         T  A  A  N  W  D  G  R  G  A  V  W  S  K  I  Y  Q  D  M  P
   361   caccgccgccaactgggatggcaggggcgccgtgtggtccaagatctaccaggacatgcc
         R  I  A  G  S  L  T  W  P  T  N
   421   gcgcattgcggggagtctgacctggcctaccaatgGTACGAAATCCTCTTCTATCCTTCA
                                                                  A  R
   481   TACTTGCTATTCCTCCAACTGCCTGGCAGCTCACACTAACTTCCACACACCCAGgcgccc
            S  V  S  V  T  I  P  R  C  L  Q  D  G  H  Y  L  L  R  A  E
   541   gttccgtctcggtaaccatccccgctgcctgcaagacggccactacctgttgcgcgccg
         H  I  G  L  H  S  A  S  G  V  G  G  A  Q  F  Y  I  S  C  A
   601   agcacatcggcctgcacagcgcgagcggcgtgggcggcgcgcagttctacatctcgtgtg
         Q  L  Y  V  S  G  G  T  G  T  W  N  P  R  N  K  V  A  F  P
   661   cccagctctacgtcagcggcggcaccggcacttggaacccgcgcaacaaggtcgcgttcc
         G  A  Y  S  P  T  H  P  G  I  M  I  N  I  Y  W  P  V  P  T
   721   ccggcgcctacagcccgacgcacccgggcatcatgatcaacatctactggccggtgccga
         S  Y  T  P  P  G  P  P  V  E  T  C  *
   781   cgagctacacgccgccggggccgccggttgagacgtgctga
```

Fig. 1

```
seq2>
         M   R   P   F   L   A   A   L   A   A   A   T   T   V   H   A   H   G   W   V
   1   atgcgccccttcctcgccgccctcgccgcggccaccacggtccacgcccacggctgggtc
         D   N   A   T   I   D   G   V   F   Y   Q   L   Y   H   P   Y   M   D   P   Y
  61   gacaacgccaccatcgacggcgtcttctaccagctctaccacccgtacatggacccgtac
         M   G   E   F   A   P   P   R   I   S   R   K   L   V   W   N   G   Y   V   N
 121   atgggcgagttcgccccgcctcgcatctcgcgcaagctggtgtggaacggctacgtgaac
         D   V   T   S   I   D   L   Q   C   G   G   H   T   A   E   G   Q   I   G   T
 181   gacgtgacgtccatcgacctgcaatgcggcggacacacggccgaagggcaaatcggcacg
         E   P   A   P   L   H   A   P   A   T   A   G   S   T   V   N   L   R   W   T
 241   gaacccgcgccgctgcacgccccgccacggccgggtcgacggtcaacctccgctggacg
         L   W   P   D   S   H   M   G   P   I   M   T   Y   M   A   R   C   P   D   E
 301   ctgtggccggactcgcacatggggcccatcatgacgtacatggcgcggtgtccggacgag
         G   C   D   K   W   L
 361   ggttgtgataagtggttGCCGGGGGAGGAGTAAGTGTTTCCTGGCGGGAATGGCTGTGTA 421   TTTGAGAAGGAGATATTATGAGTGAAACTGGGAGAGGCGAGAAGAAGAGATGCTGACGCG
                                 P   V   W   F   K   I   H   E   A   G   R   Y   T   T
 481   GGTTTTGCTCTCCTCAGaccagtctggttcaaaatccacgaagccggccggtacaccacc
         D   K   S   Y   P   D   D   I   W   E   V
 541   gacaagtcttaccccgacgacatctgggaagttGTAAGTGCCCTGCCTACCTATCCATCC 601   CTAATTCCCTCCCTCCCCTCTCCACCTCCTCCTTCCGCGCCCCCTCCCCCCCCTTATTT
                         T   R   L   M   Y   P   A   N   E   G   Y   N
 661   GCTAACCAACCCCCTCCCTTACAGacccgcctcatgtaccccgccaacgaaggctacaac
         Y   T   I   P   A   C   L   A   S   G   H   Y   L   V   R   H   E   I   I   A
 721   tacaccatccccgcctgcctcgcatccggccactacctggtccggcacgagatcatcgcc
         L   H   S   A   W   A   K   G   E   A   Q   F   Y   P   S   C   H   Q   L   T
 781   ttacactcggcctgggccaaaggcgaagcgcagttctatccctcgtgccaccagctgacc
         V   T   S   I   G   G   N   V   R   E   A   P   A   E   Y   R   V   S   F   P
 841   gtcacctccatcggcggtaacgtgcgcgaagcgccggccgagtaccgcgtcagtttcccc
         G   A   Y   K   D   D   P   G   I   F   I   N   V   W   N   P
 901   ggcgcgtacaaggacgatgatccgggtattttcatcaacgtttggaaccGTAAGTTCTTT 961   TTTTGTTCCCCTTCCTCCCAACCTACCTAGGTGTCGTAATGTGGTCCGTAAGGGTTTGTT
                                                         G   P   Y   T   I
1021   TGTTGTTGAGGGATATAGCTGACAATGGATGTGTGATAACACAGctggccccctacaccat
         P   G   P   P   V   W   T   C   P   E   S   E   *
1081   tcccggaccgccggtctggacgtgccccgagtctgagtaa
```

Fig. 1 (continued)

```
seq3>
        M  R  L  S  L  T  T  L  L  A  S  A  L  S  V  Q  G  H  A  I
    1   atgagactctccctgacaaccctcctggcctctgccctgtccgtccagggtcacgccatc
                                                                   F
   61   ttcCAGGTGCGTTCCTTTCACCACCCACATCATCATGATGAACCTCAAAGTTGCTAACCC
                 Q  R  V  T  V  N  G  Q  D  Q  G  S  L  T  G  L  R  A
  121   CCGCTGGGcagagagttaccgtcaacggccaggaccaaggctcgttgactggtctccggg
           P  N  N  N  P  V  Q  N  V  N  S  Q  D  I  I  C  G  A  P
  181   ccccgaataacaacaaccccgtgcagaacgtcaacagccaggacatcatctgtggcgctc
           G  S  R  S  Q  S  V  I  N  V  N  A  G  D  R  I  G  A  W  Y
  241   ccgggtcgcggtcacagtccgtcatcaacgtcaatgccggcgaccgcatcggtgcctggt
           Q  H  V  I  G  G  A  Q  F  P  G  D  P  D  N  P  I  A  R  S
  301   accagcatgtcatcggcggcgcccagttccccggcgacccggacaacccgatcgccaggt
           H  K  G  P  I  S  V  Y  L  A  K  V  D  N  A  A  T  A  N  H
  361   cccacaagggccccatctccgtctatctggccaaggtggacaacgctgccacggcgaacc
           Q  G  L  Q  W
  421   accagggtctgcaatgGTAAACATACCTCGGGTCAAGTCAGAACCTCTGTGATCGCCGAG
                             F  K  I  W  H  D  G  F  N  P  S
  481   ACGACTAACCCCTCTTTCCCATAAACAGgttcaagatctggcacgacggcttcaacccct
           T  R  Q  W  A  V  D  T  M  I  N  N  N  G  W  V  Y  F  N  L
  541   ccacccggcaatgggccgtcgacaccatgatcaacaacaacggctgggtctatttcaacc
           P  Q  C  I  A  P  G  H  Y  L  M  R  V  E  L  L  A  L  H  S
  601   tcccgcagtgcatcgctcccggccactatctcatgcgcgtcgagctgctcgctctccact
           A  T  Y  Q  G  Q  A  Q  F  Y  I  S  C  A  Q  I  N  V  Q  S
  661   cggccacctaccaaggccaggcgcagttctacatctcgtgcgcccagatcaacgtccagt
           G  G  N  F  T  P  W  Q  T  V  S  F  P  G  A  Y  Q  A  N  H
  721   cgggcggcaactttactccctggcagacggttagcttccccggcgcctaccaggccaacc
           P  G  I  Q  V  N  I  Y  G  A  M  G  Q  P  D  N  G  G  R  P
  781   accccggcattcaggtcaacatttacggcgccatgggccagccggataacggcggcaggc
           Y  Q  I  P  G  P  E  P  I  Q  C  *
  841   cctaccagattccgggcccggagccgattcagtgctga
```

Fig. 1 (continued)

```
seq4>
         M  G  P  T  W  A  V  I  L  G  L  I  A  P  S  V  L  N
    1    atgggaccgacctgggcagtgattctggggctgattgctccttctgtgctcaGTCACAGT 61    TGCGTCTCCCAACAGACCTCTCGACTTTTATCAAGCTGGTACTGACTCATAACCCAACTC
               I  H  G  I  L  L  V  N  G  T  E  T  P  E  W  K  Y  V
  121    ACCTAGatatccatgggatcctcctggtcaatggcacagagacaccagagtggaaatacg
           L                                                       D
  181    tcctGTATGTTTCCTCATATCCTAGCCCCATTGTACGAGTTGTTGACGTGATACAGcgat
         V  A  P  A  V  P  I  S  N  P  D  S  L  P  P  G  Y  Q  G  Y
  241    gttgcgccggcggttccaatttcaaacccagactctctcccccctggataccaaggctat
         K  V  D  P  I  I  G  S  G  N  P  N  I  T  C  G  R  L  A  F
  301    aaggttgatcccatcatcggatccgggaaccccaacatcacttgtggccggctagcattt
         D  S  A  P  K  T  Q  I  A  D  V  L  A  G  S  E  V  G  F  R
  361    gactcggcacccaagacgcaaatcgccgatgtgctagccggctccgaggtaggattccga
         V  S  A  D  G  L  G  N  R  D  L  E  K  G  Y  I  P  T  F  W
  421    gtctcggctgatggcttgggaaatcgggatctggagaagggctacatcccgacgttctgg
         H  P  G  P  A  Q  A  Y  L  S  R  A  P  N  D  D  L  Y  S  Y
  481    cacccaggtccggcccaggcatacttgtcacgtgccccgaacgacgacctgtacagctac
         K  G  D  G  D  W  F  K  I  A  Y  A  G  P  V  D  D  L  T  W
  541    aaaggcgacggggactggttcaagattgcctacgctggcccggtggacgacctgacgtgg
         S  L  W  P  G  V  S  D
  601    tcccttTggccgggagtttcagatGTATGTTCATCCTCCATAGTCCTGTTTTTGCCCTCT
                                          F  N  F  T  I  P  L  S  T  P
  661    CCAGGACCAAATTATTAATATCGAGTCGCAGttcaacttcaccattccgttgtcgacacc
            P  G  K  Y  L  L  R  I  E  N  F  M  P  T  A  S  T  G  Y  L
  721    ccctggcaagtatttgctccgaatcgagaacttcatgccaacggcctcgacaggatatct
            Q  F  Y  V  N  C  A  F  V  N  I  I  G  P  G  G  T  P  T
  781    tcagttctacgtcaattgtgcatttgtcaacatcattggaccaggaggtgggaccccgac
            E  F  I  R  I  P  G  D  Y  T  D  E  D  P  G
  841    cgagttcattcgaattcccggggattacaccgacgaggatccagGTGAGTTTGTGTTATG 901    AGACATGTTCAACTCGCACCGACGAATGCTTGTTTCCTGACAGAGATTTGTAAAAACTAG
            F  L  V  P  P  E  Q  S  S  L  D  G  R  V  P  R  D  Q  L  K
  961    gctttctcgttccccggagcaaagctccttggatggcagagtcccaagggaccagttga
            L  M  S  Y  T  P  P  G  P  A  V  W  T  G  *
 1021    aactgatgagctacacgccaccaggtcctgcggtgtggacggggtga
```

Fig. 1 (continued)

```
seq5>
        M  K  A  L  T  L  L  A  A  A  T  A  A  S  A  H  T  I  F  V
   1    atgaaggccctcaccctcctcgccgccgcgaccgcggcctcggcgcacaccatcttcgtg
        Q  L  E  A  D  G  T  R  Y  P  V  S  H  G  V  R  T  P  Q  Y
   61   cagctcgaggccgacggcacgcgctaccccgtctcgcacggcgtgcgcaccccgcagtac
        D  G  P  I  T  D  V  S  S  N  D  L  A  C  N  G  G  P  N  P
  121   gacggccccatcaccgacgtctcgtccaacgacctggcctgcaacggcgggcccaacccg
        T  M  K  T  D  K  I  I  T  V  T  A  G  S  T  V  K  A  I  W
  181   accatgaagacggacaagatcatcaccgtgacggcgggcagcaccgtcaaggccatctgg
        R  H  T  L  Q  S  G  P  N  D  V  M  D  P  S  H  K  G  P  T
  241   cggcacacgctgcagtcgggccccaacgacgtcatggaccccagccacaagggcccgacg
        L  A  Y  L  K  K  V  D  N  A  L  T  D  S  G  V  G  G  G  W
  301   ctggcgtacctgaagaaggtggacaacgcgctgacggattcgggcgtgggcggcggctgg
        F  K  I  Q  E  D  G  H  S  N  G  N  W  G  T  L  K  V  I  N
  361   ttcaagatccaggaggacgggcacagcaatgggaattggggcacgctcaaggtaatcaac
        N  Q  G  I  H  Y  I  D  I  P  D  C  I  D  S  G  Q  Y  L  L
  421   aaccagggcattcactatatcgatatccccgactgcatcgacagcgggcagtatttgttg
        R  A  E  M  I  A  L  H  A  A  G  S  P  G  G  A  Q  L  Y
  481   cgggccgagatgatcgctctgcacgctgccgggtcgccgggcggtgcgcagctttatGTG 541   AGTTTCTTCCTTCTTTTCTTCTTCTCTCCCTTTGTGATAAGAATAAAGATCCACACCACA
                                                M  E  C  A  Q  I  E
  601   GTCAAACCAAAGCATCCTAACCTCGGCATCTACTCACAGatggaatgcgcccaaatcgaa
        I  V  G  G  K  G  T  V  K  P  Q  T  Y  S  I  P  G  I  Y  K
  661   atcgtcggcggcaagggcaccgtcaagccccagacctactccatcccgggcatctacaag
        S  N  D  P  G  I  L  I  N  I  Y  S  M  P  S  S  Q  Y  I
  721   tccaacgacccgggcatcctcatcaacatctactccatgtcgccctcgagccagtacatc
        I  P  G  P  P  L  F  T  C  N  G  G  G  S  N  N  G  G
  781   atccccggcccgcccctcttcacctgcaacggcggcggcggcagcaacaacggcggcggc
        N  N  G  G  S  N  P  P  V  Q  Q  P  P  A  T  T  L  T  T  A
  841   aacaacggcggcagcaaccccccgtccagcagccccccgccaccaccctcaccaccgcc
        I  A  Q  P  T  P  I  C  S  V  Q  Q  W  G  Q  C  G  G  Q  G
  901   atcgcccagcccacgcccatctgctccgtccagcagtggggtcagtgcggcggccagggc
        Y  S  G  C  T  T  C  A  S  P  Y  R  C  N  E  I  N  A  W  Y
  961   tatagcggctgcaccacctgcgcgtcgccgtataggtgtaacgagatcaacgcgtggtat
        S  Q  C  L  *
 1021   tcgcagtgcttgtaa
```

Fig. 1 (continued)

```
seq6>
         M   A   P   K   T   S   T   F   L   A   S   L   T   G   A   A   L   V   A   A
   1   atggctcccaagacctcgacgttccttgcctccctcacgggcgccgccctcgtggctgcc
         H   G   H   V   S   H   I   I   V   N   G   V   Q   Y   R   N   Y   D   P   T
  61   cacggccatgtcagccacatcattgtcaatggcgtccagtaccggaactacgaccccacc
         T   D   F   Y   S   G   N   P   P   T   V   I   G   W   S   A   L   N   Q   D
 121   accgacttctacagcggcaaccctccgaccgtgatcggctggtcggccctcaaccaggac
         N   G   F   I   E   P   N   N   F   G   T   P   D   I   I   C   H   K   S   A
 181   aacggcttcatcgagcccaacaacttcggcaccccgacatcatctgccataagtcggcc
         K   P   G   G   G   H   V   T   V   R   A   G   D   K   I   S   I   V   W   T
 241   aagcccggcggcggccacgtcacggtgagggccggtgacaagatcagcatcgtctggacc
         P   E   W   P   E   S   H   V   G   P   V   I   D   Y   L   A   A   C   N   G
 301   cccgagtggcccgagtcgcacgtcggccccgtcatcgactaccttgccgcgtgcaacggc
         D   C   E   T   V   D   K   T   S   L   R   F   F   K   I   D   G   A   G   Y
 361   gactgcgagacggtcgacaagacctccctccgcttcttcaagatcgacggcgccggctac
         D   A   A   A   G   R   W   A   A   D   A   L   R   A   N   G   N   S   W   L
 421   gacgccgcggccggccgctgggccgccgacgctctgcgcgccaacggcaactcgtggctt
         V   Q   I   P   A   D   L   K   A   G   N   Y   V   L   R   H   E   I   I   A
 481   gtgcagatccccgccgacctcaaggccggcaactacgtgcttcggcacgagatcatcgcc
         L   H   G   A   A   N   P   N   G   A   Q   A   Y   P   Q   C   I   N   I   R
 541   ctgcacggcgccgccaaccccaacggcgcccaggcctacccgcagtgcatcaacatccgc
         V   T   G   G   N   N   Q   P   S   G   V   P   G   T   Q   L   Y   K   A
 601   gtcaccggcggcggcaacaaccagccctcgggcgtccccggcacccagctctacaaggcc
         S   D   P   G   I   L   F   N   P   W   V   A   N   P   Q   Y   P   V   P   G
 661   tcggacccgggcatcctcttcaaccccctgggtcgccaaccctcagtaccccgtcccgggc
         P   A   L   I   P   G   A   V   S   S   I   P   Q   S   R   S   T   A   T   A
 721   ccggccctcatccccggcgccgtgagctccatccctcagagccgctcgaccgccaccgcc
         T   G   T   A   T   R   P   G   A   D   T   D   P   T   G   V   P   P   V   V
 781   acgggcaccgccacccgccccggcgccgacacggacccgacgggcgtccctcccgtcgtc
         T   T   T   S   A   P   A   Q   V   T   T   T   T   S   S   R   T   T   S   L
 841   accaccacttctgccccggctcaggtgaccaccaccaccagcagccgcaccacctccctc
         P   Q   I   T   T   T   F   A   T   S   T   T   P   P   P   P   A   A   T   Q
 901   cctcagatcaccaccaccttcgcgaccagcaccaccccgccgcccccggccgctacccag
         S   K   W   G   Q   C   G   G   N   G   W   T   G   P   T   V   C   A   P   G
 961   agcaagtggggccagtgcggcggcaacggctggaccggcccgaccgtctgcgcgccgggc
         S   S   C   N   K   L   N   D   W   Y   S   Q   C   I   *
1021   tcgagctgcaacaagctcaacgactggtactcgcagtgcatctaa
```

Fig. 1 (continued)

seq7>

```
          M  Y  L  L  P  I  A  A  A  A  L  A  F  T  T  T  A  Y  A  H
  1   atgtatctttt acctatcgcc gcggccgccc tagcgttcac caccaccgca tacgcccac
          A  Q  V  Y  G  L  R  V  N  D  Q  H  Q  G  D  G  R  N  K  Y
 61   gcccaagtct acggcttgcg tgtcaacgac caacaccaag gcgatgggcg caacaaatac
          I  R  S  P  S  S  N  S  P  I  R  W  D  H  V  T  H  P  F  L
121   atccgctcgc ccagcagcaa ttcccccatc cggtgggacc acgtaaccca cccattcctc
          I  C  N  I  R  D  D  N  Q  P  P  G  P  A  P  D  F  V  R  A
181   atctgcaaca tccgcgacga caaccaaccc ccgggtcccg cgcctgactt tgtccgcgcc
          F  A  G  D  R  V  A  F  Q  W  Y  H  A  R  P  N  D  P  T  D
241   ttcgccggcg accgcgtggc gttccaatgg taccacgccc gccccaacga cccgacggat
          Y  V  L  D  S  S  H  L  G  V  L  V  T  W  I  A  P  Y  T  D
301   tacgtcctcg acagctccca cctcggcgtc ctcgttacct ggatcgcgcc gtacacggac
          G  P  G  T  G  P  I  W  T  K  I  H  Q  D  G  W  N  G  T  H
361   gggcccggga ccggccccat ttggaccaag atccaccagg acgggtggaa cggcacgcac
          W  A  T  S  R  L  I  S  N  G  G  F  V  E  F  R  L  P  G  S
421   tgggccacga gccggctcat cagcaacggc gggttcgtcg agttccggct gcccggctcg
          L  K  P  G  K  Y  L  V  R  Q  E  I  I  A  L  H  Q  A  D  M
481   ctaaagcccg ggaagtacct ggtgcggcag gagattatcg ctctgcacca ggccgacatg
          P  G  P  N  R  G  P  E  F  Y  P  S  C  A  Q  L  E  V  F  G
541   cccggtccga accgcgggcc tgagttctac cccagctgcg cgcaattgga ggttttt ggg
          S  G  E  A  A  P  P  Q  G  Y  D  I  N  K  G  Y  A  E  S  G
601   tctggtgagg cggcgccgcc gcaggggtat gatatcaaca aggggtatgc ggagagcggg
          D  K  L  W  F  N  I  Y  I  N  K  N  D  E  F  K  M  P  G  P
661   gataagttgt ggttcaacat ttacatcaac aagaatgatg agttcaaaat gcctggaccg
          E  V  W  D  G  G  C  R  F  G  E  R  W  A  T  E  E  P  G  K
721   gaggtttggg atggtgggtg tcggtttgga gagcgatggg caaccgagga accaggcaag
          P  K  V  N  Q  H  G  *
781   cccaaggtga accaacacgg ataa
```

Fig. 1 (continued)

```
seq8>
        M  K  L  L  A  P  L  M  L  A  G  A  A  S  A  H
   1  atgaagctcctcgctcctctgatgctggctggcgccgccagcgcccGTGAGTAACCCCTG
                                                          T  I  F
  61  GCTGGATCTCATGCTGGTGCCAGTGTTCCATGACTGACAACCACCCTCAGacaccatctt
        T  S  L  E  V  D  G  R  N  Y  G  T  G  N  G  V  R  V  P  S
 121  cacctccctcgaggttgatggccgcaactacggcacgggcaacggcgtccgcgtcccctc
        Y  N  G  P  V  E  D  V  T  S  N  S  I  A  C  N  G  P  P  N
 181  ctacaacggccccgtcgaggatgtcacgtccaactcgatcgcctgcaacggcccgccgaa
        P  T  S  P  T  D  T  V  I  T  V  Q  A  G  Q  N  V  T  A  I
 241  cccgaccagccccgaccgacacggtcatcaccgtccaggctggccagaacgtgactgccat
        W  R  Y  M  L  N  T  Q  G  T  S  P  N  D  I  M  D  S  S  H
 301  ctggcggtacatgctcaacacccagggcacctcgcccaacgacatcatggacagcagcca
        K  G  P  T  L  A  Y  L  K  K  V  N  D  A  R  T  D  S  G  V
 361  caagggtcctactctcgcctacctcaagaaggtcaacgatgcccggactgactcgggcgt
        G  D  G  W  F  K  I  Q  H  D  G  F  D  G  T  T  W  G  T  E
 421  cggcgatggctggttcaagatccagcacgacggcttcgacggcaccacctggggcaccga
        R  V  I  F  G  Q  G  R  H  T  I  K  I  P  E  C  I  E  P  G
 481  gcgcgtcatcttcggccagggccgtcacaccatcaagatccccgagtgcatcgagcccgg
        Q  Y  L  L  R  A  E  M  I  A  L  H  G  A  Q  N  Y  P  G  A
 541  ccagtacctgctgcgtgctgagatgatcgccctccacggcgcccagaactacccgggtgc
        Q  F  Y  M  E  C  A  Q  L  N  I  V  G  G  T  G  T  K  K  P
 601  tcagttctacatggagtgcgcccagctcaacattgtcggtggcaccggcaccaagaaacc
        S  T  V  S  F  P  G  A  Y  K
 661  cagcaccgtcagcttccctggcgcttacaagGTATGTCCGAGTTTGGTACCGAGATAACT
                                           G  T  D  P  G  V  K  L
 721  GGAGATGAGAAAAGTGATGCTAACAAACCATGACAGggcaccgaccccggcgtcaagctc
        S  I  W  W  P  P  V  T  N  Y  V  I  P  G  P  D  V  F  K  C
 781  agcatctggtggccgcccgtcaccaactacgtcattcccggccccgatgtcttcaagtgc
        *
 841  taa
```

Fig. 1 (continued)

```
seq9>
         M   K   L   L   S   T   L   A   A   I   A   A   T   L   A   T   A   D   A   H
   1   atgaagctcctctcaaccctcgccgccattgcggccaccttggccacggcggatgcgcac
         Y   I   F   N   I   L   Y   V   N   G   Q   R   M   G   G   E   Y   T   Y   V
  61   tacatcttcaacatcctgtacgtcaacggccagcgcatgggcggcgagtacacctacgtg
         R   R   N   S   N   S   Y   F   P   V   F   P   D   I   L   N   S   N   D   M
 121   cggcgcaactccaactcgtacttccccgtgttccccgacatcctcaactccaacgacatg
         R   C   N   V   G   A   R   P   G   N   T   Q   T   A   T   V   R   A   G   D
 181   cgttgcaacgtgggtgccagaccgggcaacacccaaaccgccaccgtcagggccggcgac
         R   I   G   F   K   V   F   N   N   E   V   I   E   H   P   G   P   G   F   I
 241   aggatcggcttcaaggtcttcaacaacgaggtcatcgagcaccctggtcccggcttcatc
         Y   M   S   K   A   P   G   S   V   N   N   Y   D   G   S   G   D   W   F   K
 301   tacatgtccaaagccccgggcagcgtcaacaactatgacggcagcggggactggttcaag
         V   Y   E   T   G   L   C   R   G   G   G   N   V   D   T   N   W   C   S   Y
 361   gtttacgagaccggtctctgccgcggtggtggcaacgtcgacaccaactggtgctcgtac
         Y   K   D   R   L   E   F   T   I   P   P   K   T   P   P   G   E   Y   L   V
 421   tacaaggaccggctcgagtttaccatcccgcccaagactcctcccggcgagtatctggtg
         R   I   E   H   I   G   L   H   E   G   H   V   N   R   A   Q   F   Y   I   T
 481   cgtatcgagcatatcggtctgcacgagggccacgtcaacagggcgcagttctacatcacc
         C   A   Q   L   K   I   E   G   P   G   G   G   N   P   N   P   L   V   K   I
 541   tgcgcgcagctcaagattgaggggcccggcggcggcaacccgaacccactcgtgaagatc
         P   G   I   Y   R   A   N   D   P   G   I   A   Y   N   K   W   T   N   N   P
 601   ccgggcatctacagggccaacgaccccggcatcgcctacaacaagtggaccaacaacccg
         A   P   Y   I   M   P   G   P   K   V   W   D   G   N   *
 661   gcgccgtacatcatgccgggtcccaaggtgtgggatggcaactaa
```

Fig. 1 (continued)

```
seq10>
        M   L   G   S   A   L   L   L   L   G   T   A   L   G   A   T   A   H   Y   T
  1   atgctgggaagcgctcttctgctcctgggcactgccctgggcgccaccgcccactacacg
        F   P   R   I   N   S   G   G   D   W   Q   Y   V   R   R   A   D   N   W   Q
 61   ttccctaggatcaacagcggcggcgactggcagtatgtccgccgggccgacaactggcag
        D   N   G   F   V   G   N   V   N   S   P   Q   I   R   C   F   Q   S   R   H
121   gacaacggcttcgttggcaacgtcaactcgcctcagatccgtgcttccagagcaggcac
        Q   A   A   P   A   T   L   N   V   T   A   G   S   T   V   T   Y   Y   A   N
181   caggccgccccggccaccctcaacgtcaccgccggctccacggtgacctactacgccaat
        P   N   V   Y   H   P   G   P   M   A   F   Y   M   A   R   V   P   D   G   Q
241   cccaacgtctatcaccccggcccgatggccttctacatggcccgcgtccccgatggccag
        D   I   N   S   W   T   G   E   A   V   W   F   K   I   Y   H   E   Q   P
301   gatatcaactcgtggaccggcgagggtgccgtgtggttcaagatctaccacgagcagcct
        T   G   L   G   Q   Q   L   R   W   S   S   D   G
361   accggcctgggccagcagctgaggtggtctagcgatgGTACGTGAATGGTGATCCTGTGG
                                                                                K   N   S
421   CATCTCAACCTCTTCCAGACTTCTGACCCGAGCCCCCGCGGCCCTACAGgcaagaactcg
        F   Q   V   Q   I   P   R   C   I   R   S   G   Y   Y   L   L   R   A   E   H
481   ttccaggttcagatccccgctgcatccgctctggctactacctgctccgtgctgagcac
        I   G   L   H   S   A   G   S   P   G   G   A   Q   F   Y   I   S   C   A   Q
541   atcggcttgcacagcgccggcagccctggtggcgctcagttctacatctcttgcgcccag
        L   A   V   N   G   G   S   T   E   P   P   N   K   V   S   F   P   G   A
601   ctcgccgtcaacggcggtggcagcaccgagcccccaacaaggtgtccttccctggtgcc
        Y   S   P   S   D   P   G   I   Q   I   N   I   Y   W   P   V   P   T   S   Y
661   tacagcccgtccgaccccggcattcagatcaacatctactggcctgttccgacctcgtac
        K   N   P   G   P   P   V   F   Q   C   *
721   aagaaccccggccccccggtcttccagtgctaa
```

Fig. 1 (continued)

```
seq11>
      M  K  L  L  P  G  L  L  L  A  A  T  A  A  Q  A  H  Y
   1  atgaagctgcttcctgggttgcttctggcagccacggctgcccaagcccattGTACGTTT
  61  CCGATCCCCAAGACCATCTTCGAGAATTTTCGAGCCAGATCTTTCTGAGAGAGTTGCTGA
                      T  F  P  R  L  V  V  N  G  Q  P  E  E  R  D
 121  CAATTCCTGCTAGacacattccccaggctcgttgtcaacgggcagcctgaggagagggac
      W  S  V  T  R  M  T  K  N  H  Q  S  K  S  G  I  E  N  P  T
 181  tggtcggtcactcggatgacaaagaaccaccagagcaagtcgggaattgaaaacccaact
      S  P  D  I  R  C  Y  S  S  Q  T  A  P  N  V  A  I  V  P  A
 241  agccccgacatccgttgctacagctcgcagactgcccctaacgtggcgattgtgccggcc
      G  S  T  I  H  Y  I  S  T  Q  Q  I  N  H  P  G  P  T  Q  Y
 301  gggtctaccatccactacatctcgacccaacaaatcaaccatcctggcccgactcagtac
      Y  L  A  K  V  P  A  G  Q  S  A  K  T  W  D  G  S  G  N  V
 361  tatctcgccaaggtcccagctggtcagtcagccaagacctgggatggctctggcaacgtg
      W  F  K  I  A  T  S  M  P  E  Y  D  Q  N  R  Q  L  V  W  P
 421  tggttcaagatcgccacgagcatgccggagtacgatcaaaacaggcagctggtttggccc
      G  H  N
 481  ggtcataGTAAGGACTCACTCTCGTCCGATCATCTCTTTTGAGTGAGTCTTGGGCATACC
                      T  Y  Q  T  I  N  A  T  I  P  A  N
 541  CACTGACTACGTCTGCTATGACAGataccatcagaccatcaacgccaccatcccggcca
          T  P  S  G  E  Y  L  L  R  V  E  Q  I  A  L  H  M  A  S  Q
 601  acacgccgagcggagagtacctcctgcgtgtcgagcaaattgccctccacatggccagcc
          P  N  K  A  Q  F  Y  I  S  C  S  Q  I  Q  I  T  N  G  G  N
 661  agccgaacaaggcccagttctacatctcgtgctctcagattcagattaccaatggcggaa
          G  T  P  G  P  L  V  A  F  P  G  A  Y  R  S  N  D  P  G  I
 721  acggcactccgggccctctagttgcattcccggggcatacaggagcaacgaccctggca
          L  V  N  L  Y  S  G  M  Q  P  S  Q  Y  Q  P  P  G  P  A  V
 781  tcctggtcaatctctacagcggcatgcagccttcgcagtaccagcccctggaccggccg
          W  R  G  *
 841  tgtggcgtggctga
```

Fig. 1 (continued)

```
seq12>
        M   L   L   N   S   V   I   G   S   A   V   L   L   A   T   G   A   A   A   H
    1   atgctcctgaactcggtcatcggctcggccgtcctcctggccaccggcgccgccgcccac
        G   A   V   T   S   Y   V   I   A   G   K   N   Y   P   G
   61   ggtgccgtgaccagctacgtcattgccgggaagaactaccctggGTAGGTAACCTCGTGG
                                                        Y   N   G   Y   A
  121   AAGCGAATGCAGGCAGTTCATTCACTAACACATACCTCCGTTAGctacaacggctacgcc
        P   S   T   T   P   N   T   I   Q   W   Q   W   S   T   Y   D   P   I   Y   S
  181   ccgtccaccaccccaacacgatccagtggcaatggtcgacctacgaccccatctactcc
        A   T   D   P   K   L   R   C   N   G   G   R   S   A   T   Q   S   A   P   A
  241   gccaccgaccccaagctccgctgcaacggcggccgctcggccacgcagtccgccccggct
        A   P   G   D   N   I   T   A   I   W   Q   Q   W   T   H   S   Q   G   P   I
  301   gctccgggcgacaacataccgccatctggcagcagtggacgcatagccagggccccatc
        L   V   W   M   Y   K   C   P   G   A   F   S   S   C   D   G   S   G   Q   G
  361   ctcgtctggatgtacaagtgtcccggcgccttcagctcgtgcgacggctcgggccagggc
        W   F   K   I   D   E   A   G   F   N   G   D   G   K   T   V   F   L   D   T
  421   tggttcaagattgacgaggccggcttcaatggcgacggcaagaccgtgttcctcgacacc
        E   R   P   S   G   W   E   I   A   K   L   V   G   G   N   K   G   W   T   S
  481   gagcgcccctccggctgggagatcgccaagctggttggcggcaacaagggctggaccagc
        T   I   P   K   N   L   A   P   G   N   Y   L   V   R   H   E   L   I   A   L
  541   accatccccaagaacctggccccgggcaactacctggtccgccacgagttgattgccctt
        H   Q   A   N   A   P   Q   W   Y   P   E   C   A   Q   V   V   I   T   G   S
  601   caccaggccaacgccccgcagtggtaccctgagtgcgcgcaggtcgtgatcaccggctcg
        G   T   K   E   P   P   A   S   Y   K   A   A   I   P   G   Y   C   N   Q   N
  661   ggcactaaggagccgcctgcgtcgtacaaggctgccattcccggctactgcaaccagaac
        D   P   N   I   R
  721   gatcccaacattcggGTATGTGAGGCCTATTTGGAGTTCGGCTAAGGCATGATACTAACT
                        V   P   I   N   D   H   S   I   P   Q   T   Y   K   I   P   G   P
  781   CTACCCCCAGgttcctatcaacgaccactccatccccagacctacaagatccctggcc
            P   V   W   R   G   E   *
  841   ctccggtctggcgcggcgagtaa
```

Fig. 1 (continued)

```
seq13>
      M  K  L  T  T  S  I  A  L  L  A  A  A  G  A  Q  A  H  Y
  1   atgaagctcaccacctccatcgccctgctggctgcggccggcgcgcaggctcactGTACG 61   TGCTCCCTCATCTCATCCATCTCCTCAGACCATGTTTTACCTATTGGTTACTAACAAGCT
                   T  F  P  R  T  K  V  D  G  V  T  S  G  E  W  E  T
121   CTCACGCAGacaccttccccgcaccaaggtcgacggcgtcacctcgggcgagtgggaga
        I  R  I  T  E  N  H  W  S  H  G  P  V  T  D  V  T  S  Q  A
181   cgatccgcatcaccgagaaccactggtcgcacggccccgtgacggacgtgacctcgcagg
        M  T  C  Y  E  K  T  P  G  Q  G  A  P  K  T  V  N  V  K  A
241   ccatgacgtgctacgagaagacgcccggccagggcgcgcccaagacggttaacgtgaagg
        G  G  T  V  T  F  T  V  D  T  D  V  G  H  P  G  P  L  H  F
301   ccggcggcaccgtcaccttcaccgtcgacacggacgtgggccacccgggcccgctgcact
        Y  L  A  K  V  P  A  G  K  T  A  A  T  F  D  G  K  G  A  V
361   tctacttggccaaggtgcccgcgggcaagacggccgcgacgtttgacggcaagggcgccg
        W  F  K  I  Y  Q  D  G  P  G  G  L  G  T  S  S  L  T  W  P
421   tgtggttcaagatttaccaggacggccccggcgggttggggaccagctcgttgacttggc
        S  F  G
481   ctagctttgGTGAGCTTTCTTTTCTTTATTTTCTTCAATCCTCCCATAATTACCTCCCGA
                                                                 K
541   CGAGGAAATAAATATACCTTACCTGATATTAACCCATCCCCCCCACCTCCTCCAGgcaa
        K  E  V  S  V  Q  I  P  P  C  V  Q  D  G  E  Y  L  L  R  V
601   gaaggaagtctctgtccaaatccccccctgcgtgcaggacggcgagtacctgctgcgcgt
        E  H  I  A  L  H  S  A  A  S  V  G  G  A  Q  L  Y  I  S  C
661   cgagcacattgcgctgcacagcgccgcgagcgtcggcggcgcgcagctctacatttcgtg
        A  Q  I  N  V  T  G  G  T  G  T  L  N  P  G  Q  L  V  S  F
721   cgcgcaaatcaacgtcaccggcggcaccggcacgctcaacccgggccagctcgtctcgtt
        P  G  A  Y  K  P  T  D  P  G  I  L  F  Q  L  Y  W  P  P  P
781   cccgggcgcctacaagcccaccgacccgggcatcctgttccagctctactggccgccgcc
        T  Q  Y  I  N  P  G  P  A  P  V  K  C  *
841   gacccagtacatcaaccccggtccggcgccggtgaagtgctga
```

Fig. 1 (continued)

```
seq14>
       M  K  T  L  A  S  A  L  I  A  A  G  L  L  A  Q  Y  A  A  A
  1  atgaagactctcgcatccgccctcattgccgcgggccttctggcccagtacgccgctgcc
       H  A  I  F  Q  F  A  S  S  G  G  T  D  F  G  T  S  C  V  R
 61  catgccattttccagtttgccagcagcggtggcactgactttgggacgtcctgtgttagg
       M  P
121  atgccgGTGAGTGAACGGGTGCCCCTGAACATGTGTTGCTCACGAAACAAGGTTATGTTG
                  P  N  N  S  P  V  T  S  V  T  S  S  D  M  A  C  N
181  ACTCTATACAGcccaacaactctcccgtcacgagcgtcaccagcagtgacatggcttgca
          V  G  G  S  R  G  V  S  G  I  C  E  V  N  A
241  atgttggcggatctcgcggtgtatctggcatttgcgaggtgaacgGTAAGAGTTCTCCTC
                                                              G  S
301  AGCCTTTTCTCTGTCAAGCACTAAACAGCACTCGCTAACCATTTCAATCTCAGccggctc
       D  F  T  V  E  M  H  A  Q  P  N  D  R  S  C  A  S  E  A  I
361  cgacttcaccgtcgagatgcacgcgcagcccaacgaccggtcgtgcgccagcgaagccat
       G  G  N  H  F  G  P  V  M  V  Y  M  A  K  V  D  D  A  T  R
421  tggcggcaaccacttcgggcccgtcatggtgtacatggccaaggtggacgacgcgacgcg
       A  D  G  A  S  A  S  W  F  K  V  D  E  F  G  Y  D  A  G  S
481  ggcggacggtgcgtcggcgtcttggttcaaggtggacgagttcggctacgacgccggctc
       K  T  W  G  T  D  M  L  N  K  N  C  G  K  R  T  F  R  I  P
541  caagacatggggaaccgacatgctcaacaagaactgcggcaagcggacgttccgcatccc
       S  K  I  P  S  G  D  Y  L  V  R  A  E  A  I  A  L  H  T  A
601  gagcaaaatcccgtctggggactatctggtgcgtgcggaggctattgctttgcacaccgc
       G  Q  P  S  G  A  Q  F  Y  M  S  C  Y
661  gggccagccgtcgggtgcgcagttttatatgagctgctatGTGAGTTCTTCCATGCTTCC
                                                        Q  V  R  I  K  G
721  CCTTGTGGTGTCACTGTATAGAAGATGCTAATATCTCCCACAGcaagttcgcatcaaggg
       S  N  N  G  Q  L  P  A  G  V  R  I  P  G  A  Y  S  A  T  D
781  cagcaacaacggtcagcttccggctggtgttcggattcctggcgcctacagcgcgacgga
       P  G  I  L  V  D  I  W  G  N  G  F  S  Q  Y  T  I  P  G  P
841  cccgggcatcctcgtcgatatctggggcaatggtttcagccagtacactattcctggccc
       R  V  I  D  G  S  F  F  *
901  tcgtgtcattgatgggagcttttctga
```

Fig. 1 (continued)

```
seq15>
        M  P  R  F  T  K  S  I  V  S  A  L  A  G  A  S  L  V  A  A
   1    atgcctcgcttcaccaagtccattgtctcggccctggccggcgcttccctggtcgcagcc
        H  G  H  V  T  H  I  V  I  N  G  V  L  Y  P  N  F  D  P  T
  61    cacggccatgtcacccacatcgtcatcaacggcgtgctgtacccgaacttcgaccctaca
        S  H  P  Y  L  Q  N  P  P  T  V  V  G  W  T  A  A  N  T  D
 121    tcccacccttacctgcagaacccgccgaccgttgtgggctggaccgccgccaacaccgac
        N  G  F  V  A  P  D  Q  F  A  S  G  D  I  I  C  H  N  Q  A
 181    aacggcttcgttgctcccgaccagttcgcctcgggcgatatcatctgccacaaccaggcc
        T  N  A  G  G  H  A  V  V  A  A  G  D  K  I  W  I  Q  W  D
 241    accaacgcgggcggccacgccgtggtcgcggccggcgacaagatttggatccagtgggac
        Q  W  P  E  S  H  H  G  P  V  L  D  Y  L  A  S  C  G  S  S
 301    cagtggcctgagagccaccacggccccgtcctcgactacctcgcctcctgcggcagctcg
        G  C  E  S  V  N  K  L  D  L  E  F  F  K  I  G  E  K  G  L
 361    ggctgcgagtcggtcaacaagctcgacctcgagttcttcaagatcggcgaaaagggcctg
        I  D  G  S  S  A  P  G  R  W  A  S  D  E  L  I  A  N  N  A
 421    atcgacggctcctccgcgccgggccggtgggcgtcggacgagctgatcgccaacaacgcc
        G  W  L  V  Q  I  P  A  D  I  A  P  G  H  Y  V  L  R  H  E
 481    ggctggctggtccagatccccgccgacattgcgcccggccactacgtcctgcgccacgaa
        I  I  A  L  H  A  A  G  Q  P  N  G  A  Q  N  Y  P  Q  C  F
 541    atcatcgccctccacgccgccggccagcccaacggcgcccagaactacccgcagtgcttc
        N  L  L  V  T  G  S  G  T  A  R  P  Q  G  V  K  G  T  A  L
 601    aacctcctcgtcacgggctccggcaccgcgcggccgcagggcgtcaagggaacagcgctg
        Y  T  P  N  D  K  G  I  L  A  G  I  Y  N  A  P  V  S  Y  E
 661    tacacccccaacgacaagggcatcttggcgggcatctacaatgccccgtctcgtacgag
        I  P  G  P  A  L  Y  S  G  A  A  R  N  L  Q  Q  S  S  S  Q
 721    attcccggccccgcgctctactccggcgccgccaggaacttgcagcagagctcgtcccag
        A  T  S  T  A  T  A  L  T  G  D  A  V  P  V  P  T  Q  A  P
 781    gccacgtcgactgccacggctttgactggggacgcggtgcctgttccgacccaagccccc
        V  T  T  T  S  S  S  S  A  D  A  A  T  A  T  S  T  T  V  Q
 841    gtcactaccacttcctcttcttcggccgatgccgccaccgccacctccaccaccgtccag
        P  P  Q  Q  T  T  L  T  T  A  I  A  T  S  T  A  A  A  A  P
 901    ccgccccagcaaaccacccctcacgaccgccatcgccacgtcgaccgctgctgctgccccg
        T  T  T  A  G  S  G  N  G  G  N  R  P  F  P  T  R  C  P  G
 961    acgaccaccgccggcagcggaaacgtggcaaccggcccttcccaacccgctgccctggc
        L  A  G  L  G  F  D  K  R  R  Q  L  R  A  E  E  G  V  Q
1021    ctggctgggctcgggtttgacaagcgccgtcgccagctccgcgctgaggagggtgtgcag
        V  V  A  *
1081    gtggttgcttga
```

Fig. 1 (continued)

```
seq16>
        M  K  G  L  L  S  I  A  A  L  S  L  A  V  G  E  A  S  A  H
   1 atgaagggacttctcagcatcgccgcccttccctggcggttggtgaggcttcggcccac
        Y  I  F  Q  Q  L  S  T  G  G  T  K  H  P  M  W  K  Y  I  R
  61 tacatcttccagcagctctcgacgggtggcaccaagcaccccatgtggaagtacatccgc
        Q  H  T  N  Y  N  S  P  V  I  D  L  D  S  N  D  L  R  C  N
 121 cagcacaccaactacaactctcccgtcatcgacctcgactccaacgacctccgctgcaat
        V  G  A  R  G  A  G  T  E  T  V  T  V  A  A  G  S  S  L  T
 181 gtcggtgcccggggtgctggaactgagaccgttacggtcgctgctggctcgagcctgacc
        F  H  L  D  T  P  V  Y  H  Q  G  P  V  S  V
 241 ttccacctcgacacccccgtctaccaccagggccctgtgtcggtGTAAGTAGAAGTTCTC
                                                  Y  M  S  K
 301 AGACGAACCACCAATGTCGGCAGATAATTTCTAACTCCGATGTCCAGctatatgtccaag
        A  P  G  S  V  S  D  Y  D  G  S  G  G  W  F  K  I  Q  D  W
 361 gctcccggctccgtgtcggactatgacggcagcggcggctggttcaagattcaagactgg
        G  P  T  F  T  G  S  G  A  T  W  K  L  D  D  S  Y  T  F  N
 421 ggcccgaccttcaccggcagcggcgccacctggaagctggatgactcctacaccttcaac
        I  P  S  C  I  P  D  G  E  Y  L  V  R  I  Q  S  L  G  I  H
 481 atccccctcgtgcattcccgacggcgagtacctcgtccgcatccagtccctgggtatccac
        N  P  W  P  A  G  I  P  Q  F  Y  I  S  C  A  Q  V  R  V  T
 541 aaccctggccggcgggtattccgcagttctatatctcgtgcgctcaggtgcgcgtcacc
        G  G  G  N  A  N  P  S  P  Q  V  S  I  P  G  A  F  K  E  T
 601 ggcggtggcaacgcgaacccgagcccgcaggtgtcgatcccaggtgccttcaaggagacc
        D  P  G  Y  T  A  N
 661 gacccgggctacactgccaacGTGAGTTTCCATCCATGCTACATATCCCTTTTACGCTCT
                              I  Y  N  N  F  R  S  Y  T  V
 721 CGATCCCATGACTAACCCCCCCCTGAAAAGatctacaacaacttccgcagctacaccgtc
        P  G  P  S  V  F  T  C  S  G  N  S  G  G  G  S  N  P  S  N
 781 cccggcccgtccgtcttcacctgcagcggcaacagcggcggcggctccaaccccagcaac
        P  N  P  P  T  P  T  T  F  T  T  Q  V  T  T  P  T  P  A  S
 841 cctaaccccccgaccccgacgaccttcaccacccaggtgaccaccccgaccccggcgtct
        P  P  S  C  T  V  A  K  W
 901 ccgccctcttgcaccgtcgcgaagtgGTACGTCTGAAAAAAAATCTCCTCCAGGCCGGAC
                                 G  Q  C  G  G  Q  G  Y  S  G
 961 ATGAGAAAACTAACATGAACGAAAACAGgggccagtgcggtggccagggctacagcggc
        C  T  N  C  E  A  G  S  T  C  R  Q  Q  N  A  Y  Y  S  Q  C
1021 tgcaccaactgcgaggccggctcgacctgcaggcagcagaacgcttactattctcagtgc
        I  *
1081 atctaa
```

Fig. 1 (continued)

```
seq17>
        M  R  P  F  S  L  V  A  L  A  T  A  V  S  G  H  A  I  F  Q
    1   atgaggcccttctcactcgtcgctctggcgacggccgtcagcggccacgccatcttccag
        R  V  S  V  N  G  V  D  Q  G  Q  L  K  G  V  R  A  P  S  S
   61   cgcgtgtcggttaacggcgtcgaccaaggccagctcaagggcgtccgcgctcccctcgagc
        N  Y  P  I  E  N  V  N  H  P  D  F  A  C  N  T  N  I  Q  H
  121   aactacccatcgagaacgtcaaccaccccgactttgcctgcaacaccaacatccagcac
        R  D  G  T  V  I  K  I  P  A  G  A  T  V  G  A  W  W  Q  H
  181   cgcgacggcaccgtcatcaagatccccgccggcgccaccgtcggcgcctggtggcagcac
        E  I  G  G  P  S  F  P  G  D  P  D  N  P  I  A  A  S  H  K
  241   gagatcggcgggccctcgttcccgggtgacccggataacccgatcgctgcttcgcacaag
        G
  301   gGTGAGTTCCCATAGATAGATCTCTTCTCTCCCGACCCCTTGTATCCTCTCATAACTAAC
                                   P  I  Q  V  Y  L  A  K  V  D  N  A  A  T
  361   CACCTCAACCCCCAGgccctatccaagtctacctcgccaaggtcgacaacgccgcgacc
        A  S  P  N  G  L  R  W  F  K  I  A  E  K  G  L  S  G  G  V
  421   gcctccccaacggcctgcggtggttcaagattgccgagaagggcctgtcgggcggcgtc
        W  A  V  D  E  M  I  R  N  N  G  W  H  Y  F  T  M  P  Q  C
  481   tgggccgtcgacgagatgatccgcaacaacggctggcactacttcaccatgccgcagtgc
        I  A  P  G  H  Y  L  M  R  V  E  L  L  A  L  H  S  A  S  F
  541   atcgcgcccggccactacctgatgcgcgtcgagctgttggcgctgcactcggccagcttc
        P  G  G  A  Q  F  Y  M  E  C  A  Q  I  E  V  T  G  S  G  N
  601   ccggcggcgcccagttctacatggagtgcgcccagatcgaggtcaccggctcgggcaac
        F  S  P  S  E  T  V  S  F  P  G  A  Y  P  A  N  H  P  G  I
  661   ttctcgccctccgagacggtcagcttccccggcgcctacccggccaaccacccgggtatc
        V  V  S  I  Y  D  A  Q  G  N  A  N  N  G  G  R  E  Y  Q  I
  721   gtcgtcagcatctacgacgcccagggtaacgccaacaacggcgggcgcgagtaccagatc
        P  G  P  R  P  I  T  C  S  G  G  G  S  N  N  G  G  G  N  N
  781   cccgggccgcggccgatcacctgctccggcggtggaagcaacaatggtggcgggaacaac
        N  G  G  G  N  N  N  G  G  G  N  N  N  G  G  G  N  N  N  G
  841   aatggtggtggaaacaacaacggcggcggcaacaacaacggcggtgggaacaacaacggt
        G  G  N  T  G  G  G  S  A  P  L  W  G  Q  C  G  G  N  G  Y
  901   ggtggtaacaccggtggcggctcggcgccgctctggggccagtgcggcggcaatgggtat
        T  G  P  T  T  C  A  E  G  T  C  K  K  Q  N  D  W  Y  S  Q
  961   accggcccgacgacttgtgccgagggtacttgcaagaagcagaatgactggtactcgcag
        C  T  P  *
 1021   tgtacgccttag
```

Fig. 1 (continued)

```
seq18>
         M  V  L  R  S  L  S  I  L  A  F  V  A  R  G  V  F  A  H  G
     1   atggtgttgcggtctctctctatcctggccttcgtagccagaggcgtcttcgcccacggt
         G  L  S  N  Y  T  V  G  D  T  W  Y  S  G
    61   ggcctctccaactacacggtcggcgacacgtggtatagcggGTGCGTCCATGAACAACTC
   121   CTATATCTTCCCCCCCTCCACATTGCGACCGCTGCACATCTCACTCGTCCATAAACAACA
                                                                Y  D
   181   ACATCAATCGGTAGACACTGTCCAAAAGCTAACCACCGTACCTCCTGAACACAGctacga
         P  F  T  P  A  A  A  Q  L  S  Q  P  W  L  I  Q  R  Q  W  T
   241   ccccttcaccccgccgccgcccaactctcccaaccctggctgatccaacgccaatggac
         S  I  D  P  L  F  S  P  T  S  P  Y  L  A  C  N  F  P  G  T
   301   cagcatcgacccgctcttctccccgacctctccctacctcgcctgcaacttccccggcac
         A  P  P  S  Y  I  P  L  R  A  G  D  I  L  T  A  V  Y  W  F
   361   cgcgccaccatcttacatccctctccgcgccggcgacatcctcaccgcggtttactggtt
         W  L  H  P  V  G  P  M  S  V  W  L  A  R  C  A  G  D  C  R
   421   ctggctgcaccccgtggggccgatgagcgtttggctggcgcggtgcgcaggggactgccg
         D  E  D  V  T  R  A  R  W  F  K  I  W  H  A  G  F  L  E  G
   481   cgacgaggacgtgacgcgggcgcgctggttcaagatctggcatgcggggtttctggaggg
         P  N  L  E  L  G  M  W  Y  Q  K  K  F  Q  R  W  D  G  P
   541   gccgaatttggagctcgggatgtggtatcagaagaagttccagcggtgggatggcgggcc
         A  L  W  R  V  I  P  R  G  L  K  K  G  L  Y  M  V  R  H
   601   ggcgctctggcgggtgaggataccgagggggttgaagaagggggttgtacatggtcaggca
         E  I  L  S  I  H  V  G  G  R  P  Q  F  Y  P  E  C  A  H  L
   661   tgagattttgtcgattcatgtgggtggacggccccagttttatcccgagtgtgcgcactt
         N  V  T  E  G  G  E  V  V  V  P  G  E  W  T  R  R  F  P  G
   721   gaatgtgacggagggtggtgaggtggtagtgccggggagtggacgagaaggttccctgg
         A  Y  D  D  D
   781   ggcgtatgacgatgatgGTGAGTGCCTTGCTAGACGGGAAGGCTCTATGGATGGGGCGGA
                                                              K  S  V  F
   841   TGAGACGAAAGGCTGGTGTGAGACTGTCAGCACTGACGGCCTGCAGacaagtcagtcttc
         I  D  I  Y  R  P  E  H  E  N  R  T
   901   atcgatatctaccggccggaacatgaaaacaggacgGTACGTGGACAAGCAAGCCTCGG
                                                     D  Y  E  I  P  G  G  P  I
   961   ATTTTTCAGATTTTCGACTCTGACAACGAACAGgactatgagatccctggaggcccgatt
         W  E  S
  1021   tgggaaagGTACGTACAATCGCATCATCTTGACTCTGTATTCAGGGGCTAACATAAACAC
             L  G  E  M  E  L  W  P  E  *
  1081   AGcttggggggagatggagttatggcctgaatga
```

Fig. 1 (continued)

seq19>
```
         M  R  T  V  F  A  A  A  L  A  A  L  A  A  R  E  V  A  G  H
   1 atgaggaccgtcttcgccgccgcactggcagcactcgctgcccgggaagtcgccggccat
     A  T  F  Q  Q  L  W  V  D  G  T  D  Y
  61 gccacgttccagcaactctgggttgacggaaccgattatATAAGTGCCCCCCTTTTCTCG
                                            G  S  T  C  V  R  L  P
 121 GTTCCATTTGATATCATGATGCTGACACCCCAGCACggcagcacctgcgtccgcctccc
     A  S  N  S  P  L  T  D  V  T  S  S  D  F  A  C  N  I  G  G
 181 cgccagcaacagccccctgaccgacgtcaccagcagcgacttcgcctgcaacatcggcgg
     R  R  G  V  G  G  K  C  P  V  K  A  G  G  V  V  T  I  E  M
 241 ccggcgcggcgtgggcggcaaatgccccgtcaaagccggcggcgtggtcacgatcgagat
     H  Q  Q  P  N  D  R  N  C  R  S  E  A  I  G  G  M  H  W  G
 301 gcatcagcagcccaacgaccggaactgccgcagcgaggccatcggcggcatgcactgggg
     P  V  Q  V  Y  L  S  K  V  P  D  A  S  T  A  E  P  T  Q  V
 361 tccggtgcaggtctacctcagcaaggtccccgacgcgtcgaccgccgagccgacgcaggt
     G  W  F  K  I  F  S  N  A  W  K  K  P  G  G  N  S  G  D
 421 gggctggttcaagatcttctccaacgcgtgggccaagaagcccggcggcaactcgggcga
     D  D  Y  W  G  T  R  E  L  N  G  C  C  G  R  M  D  V  P  I
 481 cgacgactactggggcacgcgcgagctcaacggctgctgcgggcgcatggacgtgccgat
     P  T  D  L  E  D  G  D  Y  L  L  R  A  E  A  L  H  A
 541 ccccaccgacctggaagacggcgactacctgctgcgcgccgaggcgctggcgctgcacgc
     M  P  G  Q  F  Y  M  S  C  Y  Q  I  T  I  T  G  G  T  G  T
 601 catgccgggccagttctacatgtcgtgctaccagatcaccatcacgggcggcacgggcac
     A  K  P  A  T  V  R  F  P  G  A  Y  T  N  N  D  A  G  I  R
 661 cgcgaagccggcgactgtccgcttccccggagcgtacaccaacaacgacgccggcatccg
     A  N  I  H  A  P  L  S  T  Y  I  A  P  G  P  E  V  Y  S  G
 721 cgccaacatccacgccccgctgagcacctacatcgcgcccggcccggaggtgtactccgg
     G  T  T  R  A  P  G  E  G  C  P  G  C  A  T  T  C  Q  V  G
 781 cggtaccacccgggcgcccggtgagggctgccccgggatgtgctacgacctgccaggttgg
     S  S  P  S  A  Q  A  P  G  H  G  T  A  V  G  G  A  G  G
 841 ctcgtcgcccagcgcgcaggctccaggccatggcacggccgtgggcggcggagctggtgg
     P  S  A  C  T  V  Q  A  Y  G  Q  C  G  G  Q  G  Y  T  G  C
 901 cccgtctgcttgcaccgtccaggcgtatggccagtgcggtggccagggatacacgggttg
     T  E  C  A
 961 caccgagtgcgcgGTAAGTTGGGACTTCCTTGTCATTAAAATCGCAAATGGAACGGATGG
                    D  G  F  V  C  R  D  V  S  A  P  W  Y  S
1021 GCTAACATTTGCGGGTGCAGatggtttcgtttgccgcgacgtctcggctccgtggtact
     Q  C  Q  P  A  F  *
1081 ctcagtgccagcctgctttctaa
```

Fig. 1 (continued)

```
seq20>
         M  R  L  P  Q  V  A  S  V  L  A  L  A  A  Q  V  H  G  H  G
    1  atgaggctcccccaagtggcttccgttctggccctcgcggcccaggtccacggtcacggc
         Y  I  Y  R  V  T  A  D  N  I  V
   61  tacatctaccgtgtcaccgccgacaacattgtGTAAGCGCCCTCAGATTCCGGACCTCTT
                                      Y  P  G  Y  D  I  Y  V
  121  CCTACCTGGTGGCTAACCTTCTCTCAACTCTTCAGctacccgggatacgacatctatgtc
         D  P  L  L  Q  P  P  P  Y  R  I  A  Y  G  G  G  Q  T  G  P
  181  gatcccctcctccaaccgccccgtaccgcattgcctacggtggtggccagacgggtccc
         V  Y  D  I  N  S  K  D  I  A  C  Q  R  V  H  S  P  A  P  G
  241  gtctatgatatcaacagcaaggatatcgcctgccagcgcgtccacagcccgctccgggt
         L  I  A  Q  A  R  A  G  S  N  I  T  F  W  W  S  R  W  L  Y
  301  ctgattgcccaggctcgcgcgggcagcaacatcaccttctggtggtcgcggtggctgtac
         S  H  K  G  P  I  S  A  W  M  A  P  Y  E  G  D  I  A  N  V
  361  agccacaagggtcccatctcggcatggatggctccgtatgagggcgacattgccaatgtg
         D  V  N  Q  L  E  F  F  K  I  G  E  E  F  H  D  E  T  G  K
  421  gacgtcaaccagctcgagttcttcaagattggcgaggagttccacgatgagaccggcaag
         W  A  T  E  K  L  V  D  D  P  E  G  K  W  T  V  K  I  P  A
  481  tgggcgacggagaagctggtggacgaccccgagggcaagtggaccgtcaagatccccgcc
         D  I  K  P  G  L  Y  V  V  R  N  E
  541  gatatcaagcccggtctctatgtcgtgcggaacgagGTAAGTTTCATCCGTCCCAAAAAA
                                                                I  I
  601  GGGGTCCCATCCCATGCATGGTGCATGCCCAGTCTAATCATCATCTCCCGGATAGatcat
         A  L  H  F  A  V  R  M  P  P  F  F  A  A  F  T  P  L  G  P
  661  cgccctccacttcgccgtccgcatgcctcccttctttgccgccttcacccccctcggacc
         Q  F  Y  M  T  C  F  A  F  N  I  T  G  D  G  T  A  T  P  Q
  721  gcagttctacatgacctgcttcgccttcaacatcaccggcgacggcacggccactcccca
         G  Y  K  F  P  G  A  Y  S  K  D  D  P  A  L  W  W  D  L  E
  781  gggctacaagttccctggcgcctacagcaaggacgatccggccctgtggtgggatctgga
         E  N  K  N  P  Y  P  G  A  G  P  K  P  H  V  S  A  Y  D  V
  841  ggagaacaagaacccgtaccccggcgccggccccaagccccacgtctcggcctacgatgt
         D  L  V  P  N  E  L  Y  I  V  S  P  T  N  N  A  T  A  D  E
  901  cgacctcgtccccaacgagttgtacatcgtcagcccgacgaacaacgcgacggctgatga
         L  Y  W  E  A  Q  R  Q  A  L  A  A  Q  A  A  T  T  E  Y  F
  961  gctctactgggaggcccagaggcaggcgcttgctgcccaggcggcgacgacggagtactt
         D  S  I  G  G  *
 1021  tgactcgattggtggctaa
```

Fig. 1 (continued)

```
seq21>
         M   H   V   Q   S   L   L   A   G   A   L   A   L   A   P   S   A   S   A   H
    1    atgcacgtccagtctctccttgccggagcgctcgctctggctccgtcggcgtctgctcac
         F   L   F   P   H   L   M   L   N   G   V   R   T   G   A   Y   E   Y   V   R
   61    ttcctcttcccgcacctgatgctgaacggtgtccgcacgggagcctacgagtatgtccgg
         E   H   D   F   G   F   M   P   H   N   N   D   W   I   N   S   P   D   F   R
  121    gagcacgacttcggcttcatgccgcacaacaacgactggatcaactcgcccgatttccgt
         C   N   E   G   S   W   R   H   R   R   E   P   K   T   A   V   V   T   A   G
  181    tgcaacgaggggtcctggcgtcatcgccgcgagcccaagaccgccgtagtcactgccggc
         V   D   V   V   G   F   N   L   H   L   D   F   D   L   Y   H   P   G   P   V
  241    gttgacgtcgtgggcttcaacctgcacctggactttgacctgtaccatccgggccccgtg
         T
  301    acgGTAAGCACATCTGAGTCAGAACATACCTCCCTGTGACGTAGACTAATGAGTCTCTTA
                 I   Y   L   S   R   A   P   G   D   V   R   D   Y   D   G   S   G   D
  361    CCGCAGatctatctctcccgcgccccggcgacgtgcgtgactacgacggatctggtgac
         W   F   K   V   Y   Q   L   G   T   R   Q   P   F   N   G   T   D   E   G   W
  421    tggttcaaggtgtaccagctgggcacccgccaacccttcaacggcactgacgagggctgg
         A   T   W   K   M   K   N   W   Q   F   R   L   P   A   E   I   P   A   G   E
  481    gccacttggaagatgaagaactggcagttccgcctgcccgctgagatcccggcgggcgag
         Y   L   M   R   I   E   Q   M   S   V   H   P   P   Y   R   Q   K   E   W   Y
  541    tacctgatgcgcatcgagcagatgagcgtgcaccctccttaccgccagaaggagtggtac
         V   Q   C   A   H   L   K   I   N   S   N   Y   N   G   P   A   P   G   P   T
  601    gtgcagtgcgcccacctaaagatcaacagcaactacaacggccccgcgcccggcccgacc
         I   K   I   P   G   G   Y   K   I   S   D   P   A   I   Q   Y   D   Q   W   A
  661    atcaagattcccggagggtacaagatcagcgatcctgcgattcaatatgaccagtgggcg
         Q   P   P   P   T   Y   A   P   M   P   G   P   P   L   W   P   N   N   N   P
  721    cagccgccgccgacgtacgcgcccatgccgggaccgccgctgtggcccaacaacaatcct
         Q   Q   G   N   P   N   Q   G   G   N   N   G   G   G   N   Q   G   G   G   N
  781    cagcagggcaacccgaatcagggcggaaataacggcggtggcaaccagggcggcggcaat
         G   G   C   T   V   P   K   W
  841    ggtggctgcaccgttccgaagtgGTATGTAGAGTTCTTCACTATTATCATGAGATGCAGC
                                 G   Q   C   G   G   Q   G   Y   S   G   C
  901    GTTGGACTTGTGCTTACACCTAGAACAGgggccaatgcggtggtcagggttacagcgggt
                R   N   C   E   S   G   S   T   C   R   A   Q   N   D   W   Y   S   Q   C   L
  961    gcaggaactgcgagtctggctcgacatgccgtgcccagaacgactggtactcgcagtgcc
            *
 1021    tgtaa
```

Fig. 1 (continued)

```
seq22>
       M  P  P  P  L  L  A  T  V  L  S  L  L  A  L  T  R  G  A  L
   1   atgccaccaccactactggccaccgtcctctccttgctagccctcacccgcggcgccctt
       S  H  S  H  L  A  H  V  I  I  N  G  Q  L  Y  H  G  F  D  P
  61   tcccattcccacctagcccacgtcatcatcaacggccagctctaccacggcttcgaccca
       R  P  N  Q  N  N  H  P  A  R  V  G  W  S  T  T  A  T  D  D
 121   cgtccaaaccaaaacaaccatccagcccgtgtcggctggtccacgaccgccacagatgac
       G  F  V  T  P  G  N  Y  S  H  P  D  I  I  C  H  R  G  G  V
 181   ggcttcgtcaccccgggcaattactcccatcccgacatcatctgccaccgcggcggcgtc
       S  P  R  A  H  A  P  V  T  A  G  G  K  V  Q  V  Q  W  N  G
 241   agcccgcgcgcccacgctcccgtcaccgccggcggcaaggtccaggtccaatggaacggc
       W  P  I  G  H  V  G  P  I  L  T  Y  I  A  P  C  G  G  L  P
 301   tggccgatcggacacgtcgggccgatcctgacctacatcgcgccgtgcggcggactgccg
       G  A  E  E  G  C  T  G  V  D  K  T  D  L  R  W  T  K  I  D
 361   ggcgccgaagaaggtgtacgggcgtggacaaaaccgacctgcggtggaccaagatcgac
       D  S  M  P  P  F  R  F  T  D  A  T  K  P  V  S  G  R  A  Q
 421   gactcgatgccgccgttccggtttaccgacgccaccaagccagtctctggcagagcgcag
       F  P  I  G  Q  V  W  A  T  D  A  L  V  E  A  N  N  S  W  S
 481   ttccccgataggccaggtctgggcgacggatgcgctggtcgaggcgaataatagctggtcg
       V  V  I  P  R  N  I  P  P  G  P  Y  V  L  R  Q  E  I  V  A
 541   gtggtcattcccaggaatatcccgccggggccgtacgttttgaggcaggagattgtggcc
       L  H  Y  A  A  K  L  N  G  A  Q  N  Y  P  L  C  L  N  L  W
 601   ctgcattacgcggcgaagttgaacggggcgcagaactatccgttgtgtctgaacctctgg
       V  E  K  G  Q  Q  D  Q  G  E  P  F  K  F  D  A  Y  D  A  R
 661   gtggaaaaggggcagcaggatcagggagagcccttcaaattcgatgcttacgacgcgagg
       E  F  Y  S  E  D  H  P  G  V  L  I  D  V  M  T  M  V  G  P
 721   gagttttacagcgaggaccatccgggtgtgttgattgatgttatgacgatggttgggccg
       R  A  V  Y  R  I  P  G  P  T  V  A  S  G  A  T  R  I  P  H
 781   agagccgtgtaccggatacctggaccgaccgtggccagtggtgccacgagaattccgcac
       S  L  Q  T  S  A  E  T  W  V  E  G  T  P  V  A  V  T  R  A
 841   tcattgcagacgagcgccgagacgtgggtggaagggacgccggtggccgtgacgagggcg
       T  E  T  V  Q  M  E  I  T  T  T  P  A  G  Q  G  A  G  V  R
 901   acggaaacggttcagatggagataactacgacacctgcaggtcagggagctggtgtgagg
       T  A  T  P  A  M  P  T  P  T  V  T  K  R  W  K  G  R  F  E
 961   acagctacccctgccatgccaacaccaacagtgacgaagaggtggaagggaagatttgag
       M  G  R  P  *
1021   atgggtaggccatga
```

Fig. 1 (continued)

```
seq23>
         M  K  S  L  T  Y  A  A  L  A  A  L  W  A  Q  Q  T  A  A  H
    1  atgaagtccctgacctacgccgcgctggccgccctctgggcccagcagaccgctgctcat
         A  T  F  Q  Q  L  W  V  D  G  V  D  Y  G  S  Q  C  A  R  L
   61  gccaccttccagcaactctgggtcgacggcgtcgactacggcagtcagtgcgcccgcctg
         P  P  S  N  S  P  I  A  S  V  T  S  T  A  M  R  C  N  N  G
  121  ccgccgtccaactcccccatcgccagcgtcacctcgaccgccatgcgctgcaacaacggt
         P  R  A  A  A  K  C  P  V  K  A  G  G  T  V  T  I  E  M  H
  181  ccccgcgctgccgccaagtgccccgtcaaggctggcggcaccgtcaccatcgagatgcac
         Q
  241  cagGTTGGTTTCCTTGAAGTGTTCCCCTACCACATATACAGACCGTAGCTAACACACCCA
            Q  P  G  D  R  S  C  N  Q  D  A  I  G  G  A  H  H  G
  301  TCCTTAGcaacccggtgaccggtcctgcaaccaggacgccattggcggtgcccaccacgg
         P  V  M  V  Y  M  S  K  V  S  D  A  F  T  A  D  G  S  S  G
  361  ccccgtgatggtgtacatgtccaaggtctctgatgccttcaccgccgacggctcgtcagg
         W  F  K  I  F  Q  D  G  W  A  K  N  P  N  G  R  V  G  D  D
  421  ctggttcaagatcttccaggacggctgggccaagaaccccaacggccgcgttggcgacga
         D  F  W  G  T  K  D  L  N  T  C  C  G  K  M  N  V  K  I  P
  481  cgacttctggggcaccaaggacctcaacacctgctgcggcaagatgaacgtcaagatccc
         A  D  I  A  P  G  D  Y  L  L  R  A  E  A  I  A  L  H  A  A
  541  cgccgacatcgcccccggcgactacctgctccgcgccgaggccatcgcgctgcacgccgc
         G  P  S  G  G  A  Q  P  Y  V  T  C  Y  Q  L  T  V  T  G  G
  601  cggccccagcggtggcgcccagccctacgtcacctgctaccagctcaccgtcacgggcgg
         G  N  A  N  P  P  T  V  N  F  P  G  A  Y  S  E  R  D  P  G
  661  cggcaacgccaacccgcccaccgtcaacttccccggcgcctacagcgagcgtgaccctgg
         I  A  V  S  I  H  G  A  L  S  N  Y  V  V  P  G  P  P  V  Y
  721  catcgccgtcagcatccacggcgctctgtccaactacgtcgtccccggtcctccggtcta
         S  G  G  S  E  K  R  A  G  S  P  C  E  G  C  E  A  T  C  K
  781  ctcgggcggcagcgagaagcgcgctggcagcccctgcgagggctgcgaggccacctgcaa
         V  G  S  S  P  S  Q  T  L  A  P  S  N  P  A  P  T  S  P  A
  841  ggtcggctcgagccccagccagactcttgctccttccaacccggccccgacctctcccgc
         N  G  G  G  N  N  G  G  G  N  T  G  G  G  C  T  V  P  K  W
  901  caacggcggcggcaacaacggtggtggcaacactggcggcggctgcaccgtgcccaagtg
         Q  Q  C  G  G  Q  G  Y  S  G  C  T  V  C  E  S  G  S  T  C
  961  gcagcagtgcggcggccagggctactcgggctgcaccgtctgcgagtctggctcgacttg
         R  A  Q  N  Q  W  Y  S  Q  C  V  *
 1021  ccgcgctcagaaccagtggtactctcagtgcgtgtaa
```

Fig. 1 (continued)

```
seq24>
        M  K  L  L  L  P  A  L  L  A  L  A  A  E  S  V  S  A  H  Y
    1   atgaagctcctcctccccgccctcctggctctggccgcgagtccgtctcggcgcactac
        I  F  Q  Q  L  T  V  A  G  T  K  Y  P  V  W  K  Y  I  R  R
   61   atcttccaacaactcaccgtcgccggcaccaagtacccgtgtggaagtacatccggcgc
        N  S  N  P  A  W  L  Q  N  G  P  V  T  D  L  A  S  T  D  L
  121   aacagcaatccggcgtggcttcaaaacggccctgtgaccgacctcgcctcgaccgacctg
        R  C  N  V  G  G  Q  V  S  N  G  T  E  T  L  T  V  R  A  G
  181   cgctgcaacgtgggcgggcaggtcagcaacggcaccgagactctcacggtccgcgcgggc
        D  Q  F  T  F  H  L  D  T  A  V  Y  H  Q  G  P  T  S  L  Y
  241   gaccagttcacgttccacctcgacacggcggtgtaccaccagggcccgacctcgctgtac
        M  S  R  A  P  G  K  V  E  D  Y  D  G  S  G  P  W  F  K  I
  301   atgtcgcgcgctccgggcaaggtggaggactatgatggcagcgggccgtggtttaagatt
        Y  D  W  G  P  T  G  N  N  W  V  M  R  D
  361   tatgattggggccgacagggaataattgggtcatgagggGTATGGTTTCCCCTATTAAT 421   TATTATTATTGTTTACTTGGGGCATCATCTGGTGGTGGTGCTGGTGACGATGATAAGAGT
                                                        S  Y  T  Y  N  I
  481   GATGGAGAAGGACCTGGCTGACGACCTAAAAACCCGATCAGattcgtacacgtacaacat
        P  R  C  I  P  D  G  E  Y  L  L  R  I  Q  Q  L  G  L  H  N
  541   ccccgctgcatccccgacggcgagtatctcctgcgcatccagcagctgggtctgcacaa
        P  G  A  A  P  Q  F  Y  I  S  C  A  Q  I  K  V  T  G  G
  601   tccgggcgccgcgccgcagttctacatcagctgcgcccagatcaaggtcaccggcggcgg
        T  T  N  P  T  P  T  A  L  I  P  G  A  F  R  A  T  D  P  G
  661   cactaccaacccgaccccacggctctgattccgggagcgttcagggctacggatccggg
        Y  T  V  N  V  S  Q  T  L  S  N  S  I  S  T  S  *
  721   atacactgtcaacgtaagtcaaactttgagcaactccatatcaacctcgtga
```

Fig. 1 (continued)

```
seq25>
      M   R   S   V   S   L   L   A   A   A   F   A   P   L   A   T   A   H   T   V
   1  atgcgttctgtttcccttcttgcggccgcttttcgcgccgctggctacggcacacacggtc
      F   T   A   L   F   I   N   N   V   H   Q   G   D   G   T   C   V   R   M   A
  61  tttacagctcttttcatcaacaatgtccaccagggcgacggcacttgcgtccgtatggct
      K   Q   G   N   L   A   T   H   P   V   S   L   N   S   N   E   M   A   C   G
 121  aagcagggcaacctcgccacccatcccgtcagtctgaacagcaatgagatggcctgcgGT
 181  GGGTAGGCCCCGTTCCTCGAGCAGCTGATCTCGAACTAACATGTTGATTCTTGAACTCCA
      R   D   G   Q   Q   P   V   A   F   T   C   P   A   P   A   G   A   K   L
 241  Ggtcgcgatggccaacaaccagtggcatttacttgcccagcacctgcgggagccaagctg
      T   L   L   F   R   M   W   A   D   G   S   Q   P   G   S   I   D   K   S   H
 301  accttattgtttcgtatgtgggcagatggctctcagccaggttccatcgacaagtctcac
      V   G   P   M   S   I   Y   L   K   K   V   S   D   M   N   T   D   S   A   A
 361  gttggtcccatgtccatctacctcaagaaagtctcagatatgaacaccgactcggccgca
      G   P   G   W   F   K   I   W   S   E   G   Y   D   A   A   T   K   K   W   A
 421  gggccgggtggttcaagatctggagtgagggctacgacgctgcgacgaagaaatgggcc
      T   E   K   L   I   A   N   N   G   L   L   S   V   N   L   P   P   G   L   P
 481  acggagaaactcatcgccaacaacggtttgctcagcgtcaacctacctcccggcctccct
      A   G   Y   Y   L   A   R   H   E   I   V   T   L   Q   N   V   T   N   N   K
 541  gcaggctactacctcgcccgccacgaaatcgtcactctccaaaacgtcaccaacaacaag
      A   D   P   Q   F   Y   V   G   C   A   Q   L   F   V   Q   G   L   G   T   A
 601  gccgatccgcagttctacgtcggctgtgcgcagctgttcgtccaagggttgggcaccgcc
      A   S   V   P   A   D   K   T   V   S   I   P   G   H   L   N   P   N   D   P
 661  gcctccgtgcctgctgacaaaaccgtttccatccccggccatctgaaccccaacgacccg
      A   L   V   F   N   P   Y   T   Q   N   A   A   T   Y   P   S   F   G   P   P
 721  gcgctggtattcaaccctataccaaaacgctgcgacatacccaagcttcggcccaccg
      L   F   F   P   N   A   A   S   A   G   S   N   K   A   Q   S   T   L   K   Q
 781  ctcttcttcccaaatgctgcttcggcgggatcaaacaaggcccagtcaacactcaagcaa
      T   S   G   V   I   P   S   D   C   L   I   K   N   A   N   W   C   G   R   E
 841  acctccggcgtcatcccctccgactgcctcatcaaaaacgccaactggtgcggccgtgaa
      V   P   D   Y   T   N   E   A   G   C   W   T   A   A   G   N   C   W   E   Q
 901  gttccagactataccaacgaggcgggatgctggacggcggcggggaactgttgggagcag
      A   D   Q   C   Y   K   T   A   P   P   S   G   H   K   G   C   K   T   W   E
 961  gctgatcaatgctacaagacagccccgccatcgggccataagggatgcaagacctgggag
      E   Q   K   C   N   V   I   Q   N   S   C   E   A   K   R   F   S   G   P   P
1021  gagcagaagtgcaacgtcatccagaactcctgtgaagcgaagaggttttcgggcccgcca
      N   R   G   V   K   F   A   D   M   D   V   N   Q   L   V   P   G   A   I   P
1081  aacaggggggtcaagtttgctgatatggatgtgaatcagcttgttccgggggcgatccct
      E   A   V   N   A   G   Q   N   G   E   A   V   V   V   D   G   T   T   S   S
1141  gaagcagtgaacgccggtcagaatggggaggcggttgttgttgacggcacaacgagctct
      A   D   E   K   A   S   V   D   L   T   T   S   S   L   P   T   P   T   P   A
1201  gcagatgagaaggcgagtgtggatttgacaacatcgtctctaccgacgccgacgctgcg
      A   E   E   N   G   K   E   D   E   R   L   A   L   D   P   T   L   T   E   D
1261  gctgaagaaaacgggaaggaggatgaaagactggctcttgatccgaccctgacggaggac
      E   S   F   F   S   V   E   P   T   S   E   P   T   G   V   Q   V   E   V   P
1321  gagtcgttttctcagttgagccaacgtctgagcccactggtgttcaggttgaggtgcct
      L   T   T   V   V   L   L   P   T   L   T   S   S   L   N   P   L   P   T   P
1381  ttgacaactgtggtcctccttccaacgctcacctcatctttgaatccattgccaaccccg
      T   S   I   S   Q   P   A   H   P   G   R   P   C   T   G   R   R   R   R   P
1441  acctcaatttcccagccggctcacccgggaagaccatgcacaggtcgccgtcgtaggccg
      R   P   G   F   P   K   H   P   R   D   F   *
1501  aggccagggtttccgaaacacccgcgcgatttttaa
```

Fig. 1 (continued)

seq26>
```
         M   F   F   R   N   A   A   T   L   A   L   A   Y   A   T   T   G   V   S   A
   1   atgttcttccgcaacgccgccactcttgctctggcctacgccaccaccggcgtctcggcc
         H   A   L   M   Y   G   V   W   V   N   G   V   D   Q   G   D   G   R   N   V
  61   cacgcgctcatgtacggcgtctgggtcaacggcgtcgaccaaggcgacggccgcaacgtc
         Y   I   R   T   P   P   N   N   S   P   V   K   D   L   A   S   P   D   I   V
 121   tacatccgcacgccccccaacaacagcccggtcaaagacctcgccagcccggacatcgtc
         C   N   V   N   G   G   R   A   V   P   D   F   V   Q   A   S   A   G   D   T
 181   tgcaacgtcaacggcggcgcgccgttccggacttcgtccaggcctcggcggggacacc
         L   T   F   E   W   L   H   N   T   R   G   D   D   I   I   D   R   S   H   L
 241   ctcaccttcgagtggctgcacaacacccgcggcgacgacatcatcgaccgctcccacctc
         G   P   I   I   T   Y   I   A   P   F   T   T   G   N   P   T   G   P   V   W
 301   ggccccatcatcacctacatcgccccttttaccacgggcaacccgacggggcccgtctgg
         T   K   I   A   E   Q   G   F   N   P   S   T   R   R   W   A   V   D   D   L
 361   accaaaatcgccgaacagggcttcaaccccttccacccgccgctgggccgtcgacgatctg
         I   D   N   G   G   K   T   D   F   V   L   P   A   S   L   A   P   G   R   Y
 421   atcgacaacggcggcaagaccgacttcgtcctgcccgcgtccctcgcgccgggcaggtac
         I   I   R   Q   E   I   I   A   H   H   E   S   E   T   T   F   E   S   N   P
 481   atcatccggcaggagatcatcgcgcaccacgagtccgaaaccacgttcgaatccaacccg
         A   R   G   A   Q   F   Y   P   S   C   V   Q   I   Q   V   S   S   G   S   G
 541   gcgcggggtgcccagttctacccgtcgtgcgtgcagatccaagtctcttctggctcgggc
         T   A   V   P   D   Q   N   F   D   F   N   T   G   Y   T   Y   A   D   P   G
 601   accgccgtgccggatcagaactttgacttcaacacgggctacacgtacgccgaccccggc
         I   H   F   N   I   Y   T   S   F   N   S   Y   S   I   P   G   P   E   V   W
 661   atccacttcaacatctacacctcgttcaacagctactccatccccggcccggaggtttgg
         T   G   A   S   T   G   G   G   N   G   N   G   N   G   N   A   T   P
 721   acgggcgctagcaccggcggcggcaacggcaacggcaacggcaacggcaatgccacgcct
         T   Q   P   T   P   T   P   T   V   T   P   T   P   I   E   T   A   Q   P   V
 781   acgcagcctactcccactcccactgtcactcccactcccatcgagaccgcccagccggtt
         T   T   T   T   T   S   T   R   P   F   P   T   R   C   P   G   R   R   L   K
 841   accacgacgaccacctcgacccggccgttccctacccgctgccctggccgccgcctcaag
         R   E   E   P   K   *
 901   cgtgaggagcccaaggcttga
```

Fig. 1 (continued)

```
seq27>
        M   A   H   P   W   A   R   C   V   Y   T   A   I   W   L   A   A   S   A   S
    1   atggctcatccatgggcacgttgcgtctatacagccatctggctcgctgcctccgcttct
        G   H
   61   ggacGTAGGTACAAGACTCCGGCAGTGCCATTTATGAACCCACAACGTGGACTGGTCCCG
                        S   R   V   W   S   V   S   V   N   G   R   Y   Q   G
  121   TGCTAACACATCACAGactcgcgcgtttggagtgtctcggtcaatggacgctaccaggga
        P   G   V   D   D   Y   L   R   A   P   P   S   D   S   P   V   V   D   L   D
  181   ccgggtgttgatgactacctgcgcgcaccgccaagtgactctccggtggtggacctggac
        S   P   T   L   N   C   N   V   N   G   N   K   P   V   P   G   F   V   E   V
  241   tcaccaaccctcaactgcaatgtcaatggaaacaagcctgttccagggttttgttgaggtg
        S   A   G   D   S   L   E   W   K   W   Y   Y   I   N   P   Y   N   P   S   D
  301   tctgcgggagattctctggaatggaagtggtactacatcaacccgtacaacccaagcgac
        M   I   I   A   A   E   H   R   G   P   I   I   T   Y   I   T   N   Y   T   D
  361   atgatcatcgcggcagaacaccgcggaccgatcatcacctacatcacgaattacaccgat
        G   Q   P   Q   G   A   V   W   T   K   I   D   H   E   G   Y   D   P   V   T
  421   ggccagcctcaaggagctgtctggaccaagattgatcacgaaggctacgatcctgtgaca
        D   R   F   A   V   D   N   L   I   A   N   R   W   K   A   I   K   L   P
  481   gaccggttcgccgtcgacaacttgatcgccaacaggggatggaaagcaatcaagcttccc
        M   L   A   D   G   K   Y   I   L   R   Q   E   I   I   A   L   H   S   A   H
  541   atgctcgccgacgggaagtacatcctgcgacaggagatcatcgcactccacagcgcacac
        N   Q   G   G   A   Q   L   Y   P   N   C   I   Q   I   K   V   V   G   G   K
  601   aaccaaggcggggcccagctgtatccgaactgcattcagatcaaggtcgttggtggcaag
        G   S   A   V   P   N   Q   N   F   D   L   N   K   G   Y   T   S   D   H   P
  661   ggaagcgcggtgcccaaccagaactttgatctcaacaaggggtacacatccgatcacccg
        G   L   R   F   N   L   W   Q   P   F   N   N   Y   T   I   P   G   P   E   V
  721   ggacttcggttcaacctgtggcaaccattcaacaattacaccattcccggtcctgaggtc
        W   K   G   V   V   V   A   S   N   G   T   T   N   S   T   T   N   L   T   N
  781   tggaagggagttgtggttgcgagcaatggtacaacgaacagcaccacaaatctcaccaac
        N   T   G   T   G   F   A   N   S   T   M   A   T   G   E   T   R   T   E   R
  841   aacaccggcaccggttttgcgaacagcactatggccactggtgaaacaaggaccgagagg
        S   F   M   T   L   T   A   S   H   S   D   T   G   V   P   A   K   S   H   T
  901   agttttatgacacttaccgcatcacattcagacactggcgtccccgccaaatctcatact
        V   A   V   S   W   T   T   S   A   A   V   V   G   S   P   I   S   V   T   T
  961   gtggctgtaagctggacaacatccgccgccgttgttgggtctccgattagcgttaccaca
        T   F   S   S   F   T   T   T   P   V   P   T   N   S   T   G   A   Y   L   Y
 1021   actttcagttcctttaccacaacaccggttccgacgaactctaccggtgcttatctctac
        R   Y   K   *
 1081   cggtacaagtga
```

POLYPEPTIDES HAVING CELLULOLYTIC ENHANCING ACTIVITY AND POLYNUCLEOTIDES ENCODING SAME

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

CROSS-REFERENCE TO RELATED APPLICATIONS

This application is a 35 U.S.C. 371 national application of PCT/CN2012/074673 filed Apr. 25, 2012, which claims priority or the benefit under 35 U.S.C. 119 of Chinese PCT application no. PCT/CN2011/073275 filed Apr. 25, 2011 and U.S. provisional application No. 61/485,358 filed May 12, 2011, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to polypeptides having cellulolytic enhancing activity and polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

WO 2005/074647, WO 2008/148131, WO 2011/035027 disclose isolated GH61 polypeptides having cellulolytic enhancing activity and the polynucleotides thereof from *Thielavia terrestris*. WO 2005/074656 and WO 2010/065830 disclose isolated GH61 polypeptides having cellulolytic enhancing activity and the polynucleotides thereof from *Thermoascus aurantiacus*. WO 2007/089290 discloses an isolated GH61 polypeptide having cellulolytic enhancing activity and the polynucleotide thereof from *Trichoderma reesei*. WO 2009/085935, WO 2009/085859, WO 2009/085864, and WO 2009/085868 disclose isolated GH61 polypeptides having cellulolytic enhancing activity and the polynucleotides thereof from *Myceliophthora thermophila*. WO 2010/138754 discloses isolated GH61 polypeptides having cellulolytic enhancing activity and the polynucleotides thereof from *Aspergillus fumigatus*. WO 2011/005867 discloses isolated GH61 polypeptides having cellulolytic enhancing activity and the polynucleotides thereof from *Penicillium pinophilum*. WO 2011/039319 discloses isolated GH61 polypeptides having cellulolytic enhancing activity and the polynucleotides thereof from *Thermoascus* sp. WO 2011/041397 discloses isolated GH61 polypeptides having cellulolytic enhancing activity and the polynucleotides thereof from *Penicillium* sp. WO 2011/041504 discloses isolated GH61 polypeptides having cellulolytic enhancing activity and the polynucleotides thereof from *Thermoascus crustaceous*. WO 2008/151043 discloses methods of increasing the activity of a GH61 polypeptide having cellulolytic enhancing activity by adding a soluble activating divalent metal cation to a composition comprising the polypeptide.

There is a need in the art for new enzymes to increase efficiency and to provide cost-effective enzyme solutions for saccharification of cellulosic material. The present invention provides GH61 polypeptides having cellulolytic enhancing activity and polynucleotides encoding the polypeptides.

SUMMARY OF THE INVENTION

The present invention relates to isolated polypeptides having cellulolytic enhancing activity selected from the group consisting of:

(a) a polypeptide having at least 50% sequence identity to the mature polypeptide of SEQ ID NO: 8, SEQ ID NO: 14, SEQ ID NO: 40, SEQ ID NO: 42, SEQ ID NO: 44, or SEQ ID NO: 54, or at least 60% sequence identity to the mature polypeptide of SEQ ID NO: 4 or SEQ ID NO: 52, or at least 65% sequence identity to SEQ ID NO: 36, SEQ ID NO: 38, or SEQ ID NO: 50, or at least 70% sequence identity to the mature polypeptide of SEQ ID NO: 10, SEQ ID NO: 18, or SEQ ID NO: 32, or at least 75% sequence identity to the mature polypeptide of SEQ ID NO: 30, or SEQ ID NO: 46, or at least 80% sequence identity to the mature polypeptide of SEQ ID NO: 6, SEQ ID NO: 12, SEQ ID NO: 20, SEQ ID NO: 22, SEQ ID NO: 26, SEQ ID NO: 28, or SEQ ID NO: 48, or at least 85% sequence identity to the mature polypeptide of SEQ ID NO: 2, SEQ ID NO: 16, or SEQ ID NO: 24, or at least 97% sequence identity to SEQ ID NO: 34;

(b) a polypeptide encoded by a polynucleotide that hybridizes under medium, medium-high, high, or very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, (ii) the cDNA sequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or (iii) the full-length complement of (i) or (ii);

(c) a polypeptide encoded by a polynucleotide having at least 50% sequence identity to the mature polypeptide coding sequence of SEQ ID NO: 7, SEQ ID NO: 13, SEQ ID NO: 39, SEQ ID NO: 41, SEQ ID NO: 43, or SEQ ID NO: 53, or the cDNA sequence thereof; or at least 60% sequence identity to the mature polypeptide coding sequence of SEQ ID NO: 3 or SEQ ID NO: 51, or the cDNA sequence thereof; or at least 65% sequence identity to the mature polypeptide coding sequence of SEQ ID NO: 35, SEQ ID NO: 37, or SEQ ID NO: 49, or the cDNA sequence thereof; or at least 70% sequence identity to the mature polypeptide coding sequence of SEQ ID NO: 9, SEQ ID NO: 17, or SEQ ID NO: 31, or the cDNA sequence thereof; or at least 75% sequence identity to the mature polypeptide coding sequence of SEQ ID NO: 29, or SEQ ID NO: 45, or the cDNA sequence thereof; or at least 80% sequence identity to the mature polypeptide coding sequence of SEQ ID NO: 5, SEQ ID NO: 11, SEQ ID NO: 19, SEQ ID NO: 21, SEQ ID NO: 25, SEQ ID NO: 27, or SEQ ID NO: 47, or the cDNA sequence thereof; or at least 85% sequence identity to the mature polypeptide coding sequence of SEQ ID NO: 1, SEQ ID NO: 15, or SEQ ID NO: 23, or the cDNA sequence thereof; or at least 97% sequence identity to the mature polypeptide coding sequence of SEQ ID NO: 33, or the cDNA sequence thereof;

(d) a variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54 comprising a substitution, deletion, and/or insertion at one or more (e.g., several) positions; and (e) a fragment of the polypeptide of (a), (b), (c), or (d) that has cellulolytic enhancing activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to methods of inhibiting the expression of a polypeptide having cellulolytic enhancing activity in a cell, comprising administering to the cell or expressing in the cell a double-stranded RNA (dsRNA) molecule, wherein the dsRNA comprises a subsequence of a polynucleotide of the present invention. The present also relates to such a double-stranded RNA (dsRNA) molecule, wherein optionally the dsRNA is an siRNA or an miRNA molecule.

The present invention also relates to compositions comprising the polypeptide of the present invention.

The present invention also relates to methods for degrading or converting a cellulosic material, comprising: treating the cellulosic material with an enzyme composition in the presence of a polypeptide of the present invention.

The present invention also relates to methods for producing a fermentation product, comprising: (a) saccharifying a cellulosic material with an enzyme composition in the presence of a polypeptide of the present invention; (b) fermenting the saccharified cellulosic material with one or more fermenting microorganisms to produce the fermentation product; and (c) recovering the fermentation product from the fermentation.

The present invention also relates to methods of fermenting a cellulosic material, comprising: fermenting the cellulosic material with one or more fermenting microorganisms, wherein the cellulosic material is saccharified with an enzyme composition in the presence of a polypeptide of the present invention.

The present invention also relates to a polynucleotide encoding a signal peptide comprising or consisting of amino acids 1 to 17 of SEQ ID NO: 2, amino acids 1 to 16 of SEQ ID NO: 4, amino acids 1 to 19 of SEQ ID NO: 6, amino acids 1 to 27 of SEQ ID NO: 8, amino acids 1 to 15 of SEQ ID NO: 10, amino acids 1 to 20 of SEQ ID NO: 12, amino acids 1 to 21 of SEQ ID NO: 14, amino acids 1 to 15 of SEQ ID NO: 16, amino acids 1 to 19 of SEQ ID NO: 18, amino acids 1 to 17 of SEQ ID NO: 20, amino acids 1 to 16 of SEQ ID NO: 22, amino acids 1 to 21 of SEQ ID NO: 24, amino acids 1 to 17 of SEQ ID NO: 26, amino acids 1 to 20 of SEQ ID NO: 28, amino acids 1 to 20 of SEQ ID NO: 30, amino acids 1 to 19 of SEQ ID NO: 32, amino acids 1 to 15 of SEQ ID NO: 34, amino acids 1 to 18 of SEQ ID NO: 36, amino acids 1 to 19 of SEQ ID NO: 38, amino acids 1 to 18 of SEQ ID NO: 40, amino acids 1 to 19 of SEQ ID NO: 42, amino acids 1 to 21 of SEQ ID NO: 44, amino acids 1 to 19 of SEQ ID NO: 46, amino acids 1 to 18 of SEQ ID NO: 48, amino acids 1 to 17 of SEQ ID NO: 50, amino acids 1 to 20 of SEQ ID NO: 52, or amino acids 1 to 21 of SEQ ID NO: 54, which is operably linked to a gene encoding a protein; nucleic acid constructs, expression vectors, and recombinant host cells comprising the polynucleotides; and methods of producing a protein.

The present invention further relates to a whole broth formulation or cell culture composition comprising the polypeptide of the present invention.

BRIEF DESCRIPTION OF THE FIGURES

FIG. 1 shows the genomic DNA sequence and the deduced amino acid sequence of the gene encoding a *Humicola insolens* GH61 polypeptide having cellulolytic enhancing activity (SEQ ID NOs: 1 and 2, SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, SEQ ID NOs: 15 and 16, SEQ ID NOs: 17 and 18, SEQ ID NOs: 19 and 20, SEQ ID NOs: 21 and 22, SEQ ID NOs: 23 and 24, SEQ ID NOs: 25 and 26, SEQ ID NOs: 27 and 28, SEQ ID NOs: 29 and 30, SEQ ID NOs: 31 and 32, SEQ ID NOs: 33 and 34, SEQ ID NOs: 35 and 36, SEQ ID NOs: 37 and 38, SEQ ID NOs: 39 and 40, SEQ ID NOs: 41 and 42, SEQ ID NOs: 43 and 44, SEQ ID NOs: 45 and 46, SEQ ID NOs: 47 and 48, SEQ ID NOs: 49 and 50, SEQ ID NOs: 51 and 52, SEQ ID NOs: 53 and 54, respectively).

DEFINITIONS

Figure 2:
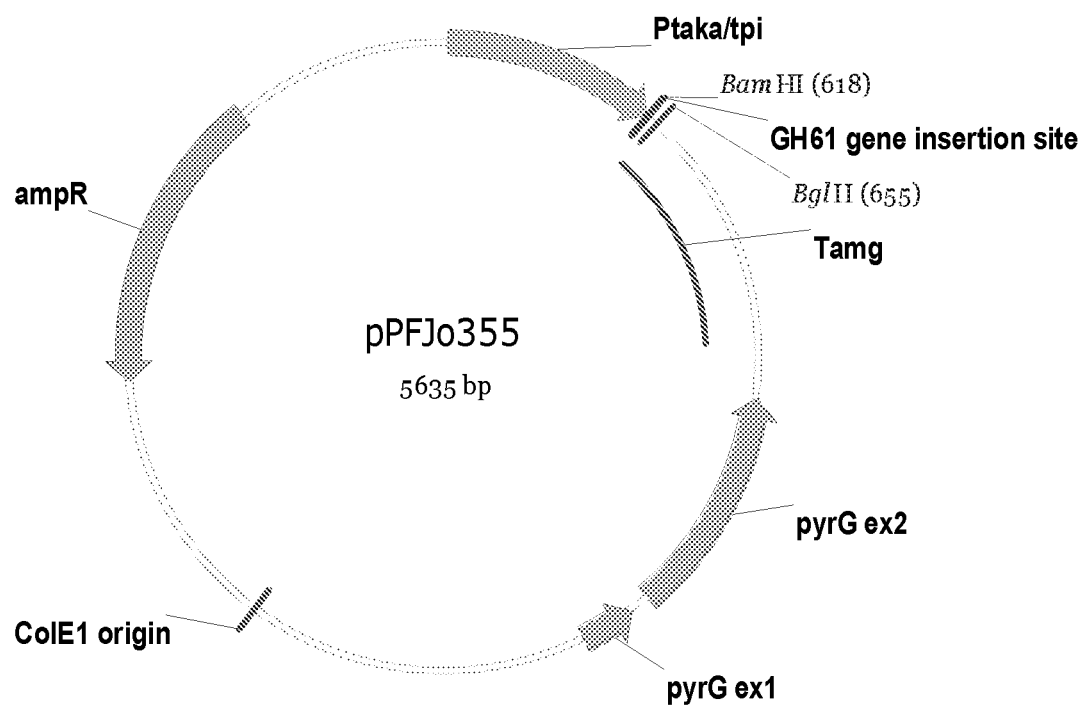
FIG. 2 shows the undigested pPFJO355 vector.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methyl-glucuronic acid per minute at pH 5, 40° C.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA. These steps include the removal of intron sequences by a process called splicing. cDNA derived from mRNA lacks, therefore, any intron sequences.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teed, 1997, Crystalline cellulose degradation: New insight into the function of cellobiohydrolases, *Trends in Biotechnology* 15: 160-167; Teed et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al, 1988, *Eur. J. Biochem.* 170: 575-581. In the present invention, the Tomme et al method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman N°1 filter paper, microcrystalline cellulose, bacterial cellulose, algal cellulose, cotton, pretreated lignocellulose, etc. The most common total cellulolytic activity assay is the filter paper assay using Whatman N°1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp mill residue, paper mill residue, waste paper, and wood (including forestry residue) (see, for example, Wiselogel et al, 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al, 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 µmole of p-nitrophenolate anion per minute at pH 5, 25° C.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 30° C., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Homologous sequence: The term "homologous sequence" is defined herein as a predicted protein having an E value (or expectancy score) of less than 0.001 in a tfasty search (Pearson, W. R., 1999, in *Bioinformatics Methods and Protocols*, S. Misener and S. A. Krawetz, ed., pp. 185-219) with the polypeptide having cellulolytic enhancing activity of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54, or the mature polypeptide thereof.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). The polypeptide of the present invention may be used in industrial applications in the form of a fermentation broth product, that is, the polypeptide of the present invention is a component of a fermentation broth used as a product in industrial applications (e.g., ethanol production). The fermentation broth product will in addition to the polypeptide of the present invention comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. The fermentation broth may optionally be subjected to one or more purification (including filtration) steps to remove or reduce one more components of a fermentation process. Accordingly, an isolated substance may be present in such a fermentation broth product.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 18 to 227 of SEQ ID NO: 2 based on the SignalP program (Nielsen et al., 1997, *Protein Engineering* 10:1-6) that predicts amino acids 1 to 17 of SEQ ID NO: 2 are a signal peptide. In another aspect, the mature polypeptide is amino acids 17 to 257 of SEQ ID NO: 4 based on the SignalP program that predicts amino acids 1 to 16 of SEQ ID NO: 4 are a signal peptide. In another aspect, the mature polypeptide is amino acids 20 to 246 of SEQ ID NO: 6 based on the SignalP program that predicts amino acids 1 to 19 of SEQ ID NO: 6 are a signal peptide. In another aspect, the mature polypeptide is amino acids 28 to 265 of SEQ ID NO: 8 based on the SignalP program that predicts amino acids 1 to 27 of SEQ ID NO: 8 are a signal peptide. In another aspect, the mature polypeptide is amino acids 16 to 310 of SEQ ID NO: 10 based on the SignalP program that predicts amino acids 1 to 15 of SEQ ID NO: 10 are a signal peptide. In one aspect, the mature polypeptide is amino acids 21 to 354 of SEQ ID NO: 12 based on the SignalP program (Nielsen et al., 1997, *Protein Engineering* 10:1-6) that predicts amino acids 1 to 20 of SEQ ID NO: 12 are a signal peptide. In another aspect, the mature polypeptide is amino acids 22 to 267 of SEQ ID NO: 14 based on the SignalP program that predicts amino acids 1 to 21 of SEQ ID NO: 14 are a signal peptide. In another aspect, the mature polypeptide is amino acids 16 to 237 of SEQ ID NO: 16 based on the SignalP program that predicts amino acids 1 to 15 of SEQ ID NO: 16 are a signal peptide. In another aspect, the mature polypeptide is amino acids 20 to 234 of SEQ ID NO: 18 based on the SignalP program that predicts amino acids 1 to 19 of SEQ ID NO: 18 are a signal peptide. In another aspect, the mature polypeptide is amino acids 18 to 226 of SEQ ID NO: 20 based on the SignalP program that predicts amino acids 1 to 17 of SEQ ID NO: 20 are a signal peptide. In one aspect, the mature polypeptide is amino acids 17 to 231 of SEQ ID NO: 22 based on the SignalP program (Nielsen et al., 1997, *Protein Engineering* 10:1-6) that predicts amino acids 1 to 16 of SEQ ID NO: 22 are a signal peptide. In another aspect, the mature polypeptide is amino acids 22 to 248 of SEQ ID NO: 24 based on the SignalP program that predicts amino acids 1 to 21 of SEQ ID NO: 24 are a signal peptide. In another aspect, the mature polypeptide is amino acids 18 to 233 of SEQ ID NO: 26 based on the SignalP program that predicts amino acids 1 to 17 of SEQ ID NO: 26 are a signal peptide. In another aspect, the mature polypeptide is amino acids 21 to 243 of SEQ ID NO: 28 based on the SignalP program that predicts amino acids 1 to 20 of SEQ ID NO: 28 are a signal peptide. In another aspect, the mature polypeptide is amino acids 21 to 363 of SEQ ID NO: 30 based on the SignalP program that predicts amino acids 1 to 20 of SEQ ID NO: 30 are a signal peptide. In one aspect, the mature polypeptide is amino acids 20 to 296 of SEQ ID NO: 32 based on the SignalP program (Nielsen et al., 1997, *Protein Engineering* 10:1-6) that predicts amino acids 1 to 19 of SEQ ID NO: 32 are a signal peptide. In another aspect, the mature polypeptide is amino acids 16 to 318 of SEQ ID NO: 34 based on the SignalP program that predicts amino acids 1 to 15 of SEQ ID NO: 34 are a signal peptide. In another aspect, the mature polypeptide is amino acids 19 to 259 of SEQ ID NO: 36 based on the SignalP program that predicts amino acids 1 to 18 of SEQ ID NO: 36 are a signal peptide. In another aspect, the mature polypeptide is amino acids 20 to 325 of SEQ ID NO: 38 based on the SignalP program that predicts amino acids 1 to 19 of SEQ ID NO: 38 are a signal peptide. In another aspect, the mature polypeptide is amino acids 19 to 298 of SEQ ID NO: 40 based on the SignalP program that predicts amino acids 1 to 18 of SEQ ID NO: 40 are a signal peptide. In one aspect, the mature polypeptide is amino acids 20 to 298 of SEQ ID NO: 42 based on the SignalP program (Nielsen et al., 1997, *Protein Engineering* 10:1-6) that predicts amino acids 1 to 19 of SEQ ID NO: 42 are a signal peptide. In another aspect, the mature polypeptide is amino acids 22 to 344 of SEQ ID NO: 44 based on the SignalP program that predicts amino acids 1 to 21 of SEQ ID NO: 44 are a signal peptide. In another aspect, the mature polypeptide is amino acids 20 to 330 of SEQ ID NO: 46 based on the SignalP program that predicts amino acids 1 to 19 of SEQ ID NO: 46 are a signal peptide. In another aspect, the mature polypeptide is amino acids 19 to 216 of SEQ ID NO: 48 based on the SignalP program that predicts amino acids 1 to 18 of SEQ ID NO: 48 are a signal peptide. In another aspect, the mature polypeptide is amino acids 18 to 490 of SEQ ID NO: 50 based on the SignalP program that predicts amino acids 1 to 17 of SEQ ID NO: 50 are a signal peptide. In one aspect, the mature polypeptide is amino acids 21 to 306 of SEQ ID NO: 52 based on the SignalP program (Nielsen et al., 1997, *Protein Engineering* 10:1-6) that predicts amino acids 1 to 20 of SEQ ID NO: 52 are a signal peptide. In another aspect, the mature polypeptide is amino acids 22 to 339 of SEQ ID NO: 54 based on the SignalP program that predicts amino acids 1 to 21 of SEQ ID NO: 54 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellulolytic enhancing activity. In one aspect, the mature polypeptide coding sequence is nucleotides 52 to 818 of SEQ ID NO: 1 or the cDNA sequence thereof based on the SignalP program (Nielsen et al., 1997, supra) that predicts nucleotides 1 to 51 of SEQ ID NO: 1 encode a signal peptide. In another aspect, the mature polypeptide coding sequence is nucleotides 49 to 1117 of SEQ ID NO: 3 or the cDNA sequence thereof based on the SignalP program that predicts nucleotides 1 to 48 of SEQ ID NO: 3 encode a signal peptide. In another aspect, the mature polypeptide coding sequence is nucleotides 58 to 875 of SEQ ID NO: 5 or the cDNA sequence thereof based on the SignalP program that predicts nucleotides 1 to 57 of SEQ ID NO: 5 encode a signal peptide. In another aspect, the mature polypeptide coding sequence is nucleotides 82 to 1064 of SEQ ID NO: 7 or the cDNA sequence thereof based on the SignalP program that predicts nucleotides 1 to 81 of SEQ ID NO: 7 encode a signal peptide. In another aspect, the mature polypeptide coding sequence is nucleotides 46 to 1032 of SEQ ID NO: 9 or the cDNA sequence thereof based on the SignalP program that predicts nucleotides 1 to 45 of SEQ ID NO: 9 encode a signal peptide. In one aspect, the mature polypeptide coding sequence is nucleotides 61 to 1062 of SEQ ID NO: 11 or the cDNA sequence thereof based on the SignalP program (Nielsen et al., 1997, supra) that predicts nucleotides 1 to 60 of SEQ ID NO: 11 encode a signal peptide. In another aspect, the mature polypeptide coding sequence is nucleotides 64 to 801 of SEQ ID NO: 13 or the cDNA sequence thereof based on the SignalP program that predicts nucleotides 1 to 63 of SEQ ID NO: 13 encode a signal peptide. In another aspect, the mature polypeptide coding sequence is nucleotides 46 to 840 of SEQ ID NO: 15 or the cDNA sequence thereof based on the SignalP program that predicts nucleotides 1 to 45 of SEQ ID NO: 15 encode a signal peptide. In another aspect, the mature polypeptide coding sequence is nucleotides 58 to 702 of SEQ ID NO: 17 or the cDNA sequence thereof based on the SignalP program that predicts nucleotides 1 to 57 of SEQ ID NO: 17 encode a signal peptide. In another aspect, the mature polypeptide coding sequence is nucleotides 52 to 750 of SEQ ID NO: 19 or the cDNA sequence thereof based on the SignalP program that predicts nucleotides 1 to 51 of SEQ ID NO: 19 encode a signal peptide. In one aspect, the mature polypeptide coding sequence is nucleotides 49 to 851 of SEQ ID NO: 21 or the cDNA sequence thereof based on the SignalP program (Nielsen et al., 1997, supra) that predicts nucleotides 1 to 48 of SEQ ID NO: 21 encode a signal peptide. In another aspect, the mature polypeptide coding sequence is nucleotides 64 to 860 of SEQ ID NO: 23 or the cDNA sequence thereof based on the SignalP program that predicts nucleotides 1 to 63 of SEQ ID NO: 23 encode a signal peptide. In another aspect, the mature polypeptide coding sequence is nucleotides 52 to 830 of SEQ ID NO: 25 or the cDNA sequence thereof based on the SignalP program that predicts nucleotides 1 to 51 of SEQ ID NO: 25 encode a signal peptide. In another aspect, the mature polypeptide coding sequence is nucleotides 61 to 925 of SEQ ID NO: 27 or the cDNA sequence thereof based on the SignalP program that predicts nucleotides 1 to 60 of SEQ ID NO: 27 encode a signal peptide. In another aspect, the mature polypeptide coding sequence is nucleotides 61 to 1089 of SEQ ID NO: 29 or the cDNA sequence thereof based on the SignalP program that predicts nucleotides 1 to 60 of SEQ ID NO: 29 encode a signal peptide. In one aspect, the mature polypeptide coding sequence is nucleotides 58 to 1083 of SEQ ID NO: 31 or the cDNA sequence thereof based on the SignalP program (Nielsen et al., 1997, supra) that predicts nucleotides 1 to 57 of SEQ ID NO: 31 encode a signal peptide. In another aspect, the mature polypeptide coding sequence is nucleotides 46 to 1029 of SEQ ID NO: 33 or the cDNA sequence thereof based on the SignalP program that predicts nucleotides 1 to 45 of SEQ ID NO: 33 encode a signal peptide. In another aspect, the mature polypeptide coding sequence is nucleotides 55 to 1110 of SEQ ID NO: 35 or the cDNA sequence thereof based on the SignalP program that predicts nucleotides 1 to 54 of SEQ ID NO: 35 encode a signal peptide. In another aspect, the mature polypeptide coding sequence is nucleotides 58 to 1100 of SEQ ID NO: 37 or the cDNA sequence thereof based on the SignalP program that predicts nucleotides 1 to 57 of SEQ ID NO: 37 encode a signal peptide. In another aspect, the mature polypeptide coding sequence is nucleotides 55 to 1036 of SEQ ID NO: 39 or the cDNA sequence thereof based on the SignalP program that predicts nucleotides 1 to 54 of SEQ ID NO: 39 encode a signal peptide. In one aspect, the mature polypeptide coding sequence is nucleotides 58 to 1022 of SEQ ID NO: 41 or the cDNA sequence thereof based on the SignalP program (Nielsen et al., 1997, supra) that predicts nucleotides 1 to 57 of SEQ ID NO: 41 encode a signal peptide. In another aspect, the mature polypeptide coding sequence is nucleotides 64 to 1032 of SEQ ID NO: 43 or the cDNA sequence thereof based on the SignalP program that predicts nucleotides 1 to 63 of SEQ ID NO: 43 encode a signal peptide. In another aspect, the mature polypeptide coding sequence is nucleotides 58 to 1054 of SEQ ID NO: 45 or the cDNA sequence thereof based on the SignalP program that predicts nucleotides 1 to 57 of SEQ ID NO: 45 encode a signal peptide. In another aspect, the mature polypeptide coding sequence is nucleotides 55 to 769 of SEQ ID NO: 47 or the cDNA sequence thereof based on the SignalP program that predicts nucleotides 1 to 54 of SEQ ID NO: 47 encode a signal peptide. In another aspect, the mature polypeptide coding sequence is nucleotides 52 to 1533 of SEQ ID NO: 49 or the cDNA sequence thereof based on the SignalP program that predicts nucleotides 1 to 51 of SEQ ID NO: 49 encode a signal peptide. In one aspect, the mature polypeptide coding sequence is nucleotides 61 to 918 of SEQ ID NO: 51 or the cDNA sequence thereof based on the SignalP program (Nielsen et al., 1997, supra) that predicts nucleotides 1 to 60 of SEQ ID NO: 51 encode a signal peptide. In another aspect, the mature polypeptide coding sequence is nucleotides 64 to 1089 of SEQ ID NO: 53 or the cDNA sequence thereof based on the SignalP program that predicts nucleotides 1 to 63 of SEQ ID NO: 53 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Pretreated corn stover: The term "PCS" or "Pretreated Corn Stover" means a cellulosic material derived from corn stover by treatment with heat and dilute sulfuric acid, alkaline pretreatment, or neutral pretreatment.

Polypeptide fragment: The term "polypeptide fragment" is defined herein as a polypeptide having one or more (e.g., several) amino acids deleted from the amino and/or carboxyl terminus of the mature polypeptide of SEQ ID NO: 2, SEQ ID NO: 4, SEQ ID NO: 6 SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54; or a homologous sequence thereof; wherein the fragment has cellulolytic enhancing activity. In one aspect, a fragment contains at least 161 amino acid residues, e.g., at least 171 amino acid residues or at least 181 amino acid residues of the mature polypeptide of SEQ ID NO: 2 or a homologous sequence thereof. In another aspect, a fragment contains at least 204 amino acid residues, e.g., at least 216 amino acid residues or at least 228 amino acid residues of the mature polypeptide of SEQ ID NO: 4 or a homologous sequence thereof. In another aspect, a fragment contains at least 193 amino acid residues, e.g., at least 204 amino acid residues or at least 215 amino acid residues of the mature polypeptide of SEQ ID NO: 6 or a homologous sequence thereof. In another aspect, a fragment contains at least 201 amino acid residues, e.g., at least 213 amino acid residues or at least 225 amino acid residues of the mature polypeptide of SEQ ID NO: 8 or a homologous sequence thereof. In another aspect, a fragment contains at least 249 amino acid residues, e.g., at least 264 amino acid residues or at least 279 amino acid residues of the mature polypeptide of SEQ ID NO: 10 or a homologous sequence thereof. In one aspect, a fragment contains at least 282 amino acid residues, e.g., at least 299 amino acid residues or at least 316 amino acid residues of the mature polypeptide of SEQ ID NO: 12 or a homologous sequence thereof. In another aspect, a fragment contains at least at least 209 amino acid residues, e.g., at least 221 amino acid residues or at least 233 amino acid residues of the mature polypeptide of SEQ ID NO: 14 or a homologous sequence thereof. In another aspect, a fragment contains at least 188 amino acid residues, e.g., at least 199 amino acid residues or at least 210 amino acid residues of the mature polypeptide of SEQ ID NO: 16 or a homologous sequence thereof. In another aspect, a fragment contains at least 181 amino acid residues, e.g., at least 192 amino acid residues or at least 203 amino acid residues of the mature polypeptide of SEQ ID NO: 18 or a homologous sequence thereof. In another aspect, a fragment contains at least 178 amino acid residues, e.g., at least 188 amino acid residues or at least 198 amino acid residues of the mature polypeptide of SEQ ID NO: 20 or a homologous sequence thereof. In one aspect, a fragment contains at least 181 amino acid residues, e.g., at least 192 amino acid residues or at least 203 amino acid residues of the mature polypeptide of SEQ ID NO: 22 or a homologous sequence thereof. In another aspect, a fragment contains at least 193 amino acid residues, e.g., at least 204 amino acid residues or at least 215 amino acid residues of the mature polypeptide of SEQ ID NO: 24 or a homologous sequence thereof. In another aspect, a fragment contains at least 182 amino acid residues, e.g., at least 193 amino acid residues or at least 204 amino acid residues of the mature polypeptide of SEQ ID NO: 26 or a homologous sequence thereof. In another aspect, a fragment contains at least 189 amino acid residues, e.g., at least 200 amino acid residues or at least 211 amino acid residues of the mature polypeptide of SEQ ID NO: 28 or a homologous sequence thereof. In another aspect, a fragment contains at least 291 amino acid residues, e.g., at least 308 amino acid residues or at least 325 amino acid residues of the mature polypeptide of SEQ ID NO: 30 or a homologous sequence thereof. In one aspect, a fragment contains at least 236 amino acid residues, e.g., at least 248 amino acid residues or at least 262 amino acid residues of the mature polypeptide of SEQ ID NO: 32 or a homologous sequence thereof. In another aspect, a fragment contains at least 257 amino acid residues, e.g., at least 272 amino acid residues or at least 287 amino acid residues of the mature polypeptide of SEQ ID NO: 34 or a homologous sequence thereof. In another aspect, a fragment contains at least 221 amino acid residues, e.g., at least 234 amino acid residues or at least 247 amino acid residues of the mature polypeptide of SEQ ID NO: 36 or a homologous sequence thereof. In another aspect, a fragment contains at least 260 amino acid residues, e.g., at least 275 amino acid residues or at least 290 amino acid residues of the mature polypeptide of SEQ ID NO: 38 or a homologous sequence thereof. In another aspect, a fragment contains at least 237 amino acid residues, e.g., at least 251 amino acid residues or at least 265 amino acid residues of the mature polypeptide of SEQ ID NO: 40 or a homologous sequence thereof. In one aspect, a fragment contains at least 238 amino acid residues, e.g., at least 252 amino acid residues or at least 264 amino acid residues of the mature polypeptide of SEQ ID NO: 42 or a homologous sequence thereof. In another aspect, a fragment contains at least 274 amino acid residues, e.g., at least 290 amino acid residues or at least 306 amino acid residues of the mature polypeptide of SEQ ID NO: 44 or a homologous sequence thereof. In another aspect, a fragment contains at least 262 amino acid residues, e.g., at least 278 amino acid residues or at least 294 amino acid residues of the mature polypeptide of SEQ ID NO: 46 or a homologous sequence thereof. In another aspect, a fragment contains at least 167 amino acid residues, e.g., at least 177 amino acid residues or at least 187 amino acid residues of the mature polypeptide of SEQ ID NO: 48 or a homologous sequence thereof. In another aspect, a fragment contains at least 400 amino acid residues, e.g., at least 424 amino acid residues or at least 448 amino acid residues of the mature polypeptide of SEQ ID NO: 50 or a homologous sequence thereof. In one aspect, a fragment contains at least 243 amino acid residues, e.g., at least 257 amino acid residues or at least 271 amino acid residues of the mature polypeptide of SEQ ID NO: 52 or a homologous sequence thereof. In another aspect, a fragment contains at least 269 amino acid residues, e.g., at least 285 amino acid residues or at least 301 amino acid residues of the mature polypeptide of SEQ ID NO: 54 or a homologous sequence thereof.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

For purpose of the present invention, the cellulolytic enhancing activity is determined by measuring the increase in reducing sugars or the increase of the total of cellobiose and glucose from the hydrolysis of phosphoric acid swollen cellulose (PASC) under the following conditions: 5 mg of PASC per ml of 50 mM sodium acetate pH 5.0 buffer containing 2 mg of *Aspergillus oryzae* GH3A beta-glucosidase WO 2002/095014) per gram of cellulose, with or without 60 mg of GH61 polypeptide per gram of cellulose, or with or without 20 mg of GH61 polypeptide per gram of cellulose, with 10 mM pyrogallol (Fluka, Milwaukee, Wis., USA) plus 10 µM copper sulfate for 3 or 4 days at 50° C.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

The polypeptides of the present invention have preferably at least 20%, e.g., at least 40%, at least 50%, at least 60%, at least 70%, at least 80%, at least 90%, at least 95%, and at least 100% of the cellulolytic enhancing activity of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0, 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

Subsequence: The term "subsequence" is defined herein as a nucleotide sequence having one or more (e.g., several) nucleotides absent from the 5' and/or 3' end of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53; or a homologous sequence thereof; wherein the subsequence encodes a polypeptide fragment having cellulolytic enhancing activity. In one aspect, a subsequence contains at least 483 nucleotides, e.g., at least nucleotides 513 or at least nucleotides 543 of SEQ ID NO: 1; or the cDNA sequence thereof. In one aspect, a subsequence contains at least 612 nucleotides, e.g., at least nucleotides 648 or at least nucleotides 684 of SEQ ID NO: 3; or the cDNA sequence thereof. In one aspect, a subsequence contains at least 579 nucleotides, e.g., at least nucleotides 612 or at least nucleotides 645 of SEQ ID NO: 5; or the cDNA sequence thereof. In one aspect, a subsequence contains at least 603 nucleotides, e.g., at least nucleotides 639 or at least nucleotides 675 of SEQ ID NO: 7; or the cDNA sequence thereof. In one aspect, a subsequence contains at least 747 nucleotides, e.g., at least nucleotides 792 or at least nucleotides 837 of SEQ ID NO: 9; or the cDNA sequence thereof. In one aspect, a subsequence contains at least 846 nucleotides, e.g., at least nucleotides 897 or at least nucleotides 948 of SEQ ID NO: 11; or the cDNA sequence thereof. In one aspect, a subsequence contains at least 627 nucleotides, e.g., at least nucleotides 663 or at least nucleotides 699 of SEQ ID NO: 13; or the cDNA sequence thereof. In one aspect, a subsequence contains at least 564 nucleotides, e.g., at least nucleotides 597 or at least nucleotides 630 of SEQ ID NO: 15; or the cDNA sequence thereof. In one aspect, a subsequence contains at least 543 nucleotides, e.g., at least nucleotides 576 or at least nucleotides 609 of SEQ ID NO: 17; or the cDNA sequence thereof. In one aspect, a subsequence contains at least 534 nucleotides, e.g., at least nucleotides 564 or at least nucleotides 594 of SEQ ID NO: 19; or the cDNA sequence thereof. In one aspect, a subsequence contains at least 543 nucleotides, e.g., at least nucleotides 576 or at least nucleotides 609 of SEQ ID NO: 21; or the cDNA sequence thereof. In one aspect, a subsequence contains at least 579 nucleotides, e.g., at least nucleotides 612 or at least nucleotides 645 of SEQ ID NO: 23; or the cDNA sequence thereof. In one aspect, a subsequence contains at least 546 nucleotides, e.g., at least nucleotides 579 or at least nucleotides 612 of SEQ ID NO: 25; or the cDNA sequence thereof. In one aspect, a subsequence contains at least 567 nucleotides, e.g., at least nucleotides 600 or at least nucleotides 633 of SEQ ID NO: 27; or the cDNA sequence thereof. In one aspect, a subsequence contains at least 873 nucleotides, e.g., at least nucleotides 924 or at least nucleotides 975 of SEQ ID NO: 29; or the cDNA sequence thereof. In one aspect, a subsequence contains at least 708 nucleotides, e.g., at least nucleotides 744 or at least nucleotides 786 of SEQ ID NO: 31; or the cDNA sequence thereof. In one aspect, a subsequence contains at least 771 nucleotides, e.g., at least nucleotides 816 or at least nucleotides 861 of SEQ ID NO: 33; or the cDNA sequence thereof. In one aspect, a subsequence contains at least 663 nucleotides, e.g., at least nucleotides 702 or at least nucleotides 741 of SEQ ID NO: 35; or the cDNA sequence thereof. In one aspect, a subsequence contains at least 780 nucleotides, e.g., at least nucleotides 825 or at least nucleotides 870 of SEQ ID NO: 37; or the cDNA sequence thereof. In one aspect, a subsequence contains at least 711 nucleotides, e.g., at least nucleotides 753 or at least nucleotides 795 of SEQ ID NO: 39; or the cDNA sequence thereof. In one aspect, a subsequence contains at least 714 nucleotides, e.g., at least nucleotides 756 or at least nucleotides 792 of SEQ ID NO: 41; or the cDNA sequence thereof. In one aspect, a subsequence contains at least 822 nucleotides, e.g., at least nucleotides 870 or at least nucleotides 918 of SEQ ID NO: 43; or the cDNA sequence thereof. In one aspect, a subsequence contains at least 786 nucleotides, e.g., at least nucleotides 834 or at least nucleotides 882 of SEQ ID NO: 45; or the cDNA sequence thereof. In one aspect, a subsequence contains at least 501 nucleotides, e.g., at least nucleotides 531 or at least nucleotides 561 of SEQ ID NO: 47; or the cDNA sequence thereof. In one aspect, a subsequence contains at least 1200 nucleotides, e.g., at least nucleotides 1272 or at least nucleotides 1344 of SEQ ID NO: 49; or the cDNA sequence thereof. In one aspect, a subsequence contains at least 729 nucleotides, e.g., at least nucleotides 771 or at least nucleotides 813 of SEQ ID NO: 51; or the cDNA sequence thereof. In one aspect, a subsequence contains at least 807 nucleotides, e.g., at least nucleotides 855 or at least nucleotides 903 of SEQ ID NO: 53; or the cDNA sequence thereof.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight.

The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Variant: The term "variant" means a polypeptide having cellulolytic enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, FEBS Letters 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1, 1,3,3-tetramethylbutyl)phenyl-polyethylene glycol) and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Cellulolytic Enhancing Activity

In an aspect, the present invention relates to isolated polypeptides having a sequence identity to the mature polypeptide of SEQ ID NO: 8, SEQ ID NO: 14, SEQ ID NO: 40, SEQ ID NO: 42, SEQ ID NO: 44, or SEQ ID NO: 54 of at least 50%, e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%; or to isolated polypeptides having a sequence identity to the mature polypeptide of SEQ ID NO: 4 or SEQ ID NO: 52 of at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%; or to isolated polypeptides having a sequence identity to the mature polypeptide of SEQ ID NO: 36, SEQ ID NO: 38, or SEQ ID NO: 50 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%; to isolated polypeptides having a sequence identity to the mature polypeptide of SEQ ID NO: 10, SEQ ID NO: 18, or SEQ ID NO: 32 of at least 70% sequence identity, e.g., at least 75%, at least 80%, at least 85%, at least 90%, at least 91%, at least 92%, at least 93%, at least 94%, at least 95%, at least 96%, at least 97%, at least 98%, at least 99%, or 100%; to isolated polypeptides having a sequence identity to the mature polypeptide of SEQ ID NO: 30, or SEQ ID NO: 46 of at least 75%, e.g., at least 80%, at least 85%, at least 90%, at least 91%, at least 92%, at least 93%, at least 94%, at least 95%, at least 96%, at least 97%, at least 98%, at least 99%, or 100%; to isolated polypeptides having a sequence identity to the mature polypeptide of SEQ ID NO: 6, SEQ ID NO: 12, SEQ ID NO: 20, SEQ ID NO: 22, SEQ ID NO: 26, SEQ ID NO: 28 or SEQ ID NO: 48 of at least 80%, e.g., at least 85%, at least 90%, at least 91%, at least 92%, at least 93%, at least 94%, at least 95%, at least 96%, at least 97%, at least 98%, at least 99%, or 100%; or to isolated polypeptides having a sequence identity to the mature polypeptide of SEQ ID NO: 2, SEQ ID NO: 16, or SEQ ID NO: 24 of at least 85% sequence identity e.g., at least 90%, at least 91%, at least 92%, at least 93%, at least 94%, at least 95%, at least 96%, at least 97%, at least 98%, at least 99%, or 100%; or to isolated polypeptides having a sequence identity to the mature polypeptide of SEQ ID NO: 34 of at least 97%, e.g., at least 98%, at least 99%, or 100%.

In one aspect, the polypeptides differ by no more than ten amino acids, e.g., nine amino acids, eight amino acids, seven amino acids, six amino acids, five amino acids, four amino acids, three amino acids, two amino acids, or one amino acid from the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54, or an allelic variant thereof; or is a fragment thereof having cellulolytic enhancing activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54. A polypeptide of the present invention preferably comprises or consists of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54, or an allelic variant thereof; or is a fragment thereof having cellulolytic enhancing activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54. In another preferred aspect, the polypeptide comprises or consists of amino acids 18 to 227 of SEQ ID NO: 2, amino acids 17 to 257 of SEQ ID NO: 4, amino acids 20 to 246 of SEQ ID NO: 6, amino acids 28 to 265 of SEQ ID NO: 8, amino acids 16 to 310 of SEQ ID NO: 10, amino acids 21 to 354 of SEQ ID NO: 12, amino acids 22 to 267 of SEQ ID NO: 14, amino acids 16 to 237 of SEQ ID NO: 16, amino acids 20 to 234 of SEQ ID NO: 18, amino acids 18 to 226 of SEQ ID NO: 20, amino acids 17 to 231 of SEQ ID NO: 22, amino acids 22 to 248 of SEQ ID NO: 24, amino acids 18 to 233 of SEQ ID NO: 26, amino acids 21 to 243 of SEQ ID NO: 28, amino acids 21 to 363 of SEQ ID NO: 30, amino acids 20 to 296 of SEQ ID NO: 32, amino acids 16 to 318 of SEQ ID NO: 34, amino acids 19 to 259 of SEQ ID NO: 36, amino acids 20 to 325 of SEQ ID NO: 38, amino acids 19 to 298 of SEQ ID NO: 40, amino acids 20 to 298 of SEQ ID NO: 42, amino acids 22 to 344 of SEQ ID NO: 44, amino acids 20 to 330 of SEQ ID NO: 46, amino acids 19 to 216 of SEQ ID NO: 48, amino acids 18 to 490 of SEQ ID NO: 50, amino acids 21 to 306 of SEQ ID NO: 52, or amino acids 22 to 339 of SEQ ID NO: 54.

In another embodiment, the present invention relates to isolated polypeptides having cellulolytic enhancing activity that are encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, (ii) the cDNA sequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or (iii) the full-length complement of (i) or (ii) (Sambrook et al., 1989, *Molecular Cloning, A Laboratory Manual,* 2d edition, Cold Spring Harbor, N.Y.).

The polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or a subsequence thereof, as well as the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54, or a fragment thereof, may be used to design nucleic acid probes to identify and clone DNA encoding polypeptides having cellulolytic enhancing activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, preferably at least 25, more preferably at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having cellulolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53 or a subsequence thereof, the carrier material is preferably used in a Southern blot.

For purposes of the present invention, hybridization indicates that the polynucleotide hybridizes to a labeled nucleic acid probe corresponding to (i) SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53; (ii) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53; (iii) the cDNA sequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53; (iv) a full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54; the mature polypeptide thereof; or a fragment thereof. In another aspect, the nucleic acid probe is SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or the cDNA sequence thereof.

In another embodiment, the present invention relates to isolated polypeptides having cellulolytic enhancing activity encoded by polynucleotides having a sequence identity to the mature polypeptide coding sequence of SEQ ID NO: 7, SEQ ID NO: 13, SEQ ID NO: 39, SEQ ID NO: 41, SEQ ID NO: 43, or SEQ ID NO: 53 of at least 50% e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%; to isolated polypeptides having cellulolytic enhancing activity encoded by polynucleotides having a sequence identity to the mature polypeptide coding sequence of SEQ ID NO: 3 or SEQ ID NO: 51 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%; to isolated polypeptides having cellulolytic enhancing activity encoded by polynucleotides having a sequence identity to the mature polypeptide coding sequence of SEQ ID NO: 35, SEQ ID NO: 37, or SEQ ID NO: 49 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%; to isolated polypeptides having cellulolytic enhancing activity encoded by polynucleotides having a sequence identity to the mature polypeptide coding sequence of SEQ ID NO: 9, SEQ ID NO: 17, or SEQ ID NO: 31 of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%; to isolated polypeptides having cellulolytic enhancing activity encoded by polynucleotides having a sequence identity to the mature polypeptide coding sequence of SEQ ID NO: 29, or SEQ ID NO: 45 of at least 75%, e.g., at least 80%, at least 85%, at least 90%, at least 91%, at least 92%, at least 93%, at least 94%, at least 95%, at least 96%, at least 97%, at least 98%, at least 99%, or 100%; to isolated polypeptides having cellulolytic enhancing activity encoded by polynucleotides having a sequence identity to the mature polypeptide coding sequence of SEQ ID NO: 5, SEQ ID NO: 11, SEQ ID NO: 19, SEQ ID NO: 21, SEQ ID NO: 25, SEQ ID NO: 27, or SEQ ID NO: 47 of at least 80%, e.g., at least 85%, at least 90%, at least 91%, at least 92%, at least 93%, at least 94%, at least 95%, at least 96%, at least 97%, at least 98%, at least 99%, or 100%; to isolated polypeptides having cellulolytic enhancing activity encoded by polynucleotides having a sequence identity to the mature polypeptide coding sequence of SEQ ID NO: 1, SEQ ID NO: 15, or SEQ ID NO: 23 of at least 85%, e.g., at least 90%, at least 91%, at least 92%, at least 93%, at least 94%, at least 95%, at least 96%, at least 97%, at least 98%, at least 99%, or 100%; or to isolated polypeptides having cellulolytic enhancing activity encoded by polynucleotides having a sequence identity to the mature polypeptide coding sequence of SEQ ID NO: 33 of at least 97%, e.g., at least 98%, at least 99%, or 100%.

In another embodiment, the present invention relates to variants of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54 comprising a substitution, deletion, and/or insertion at one or more (e.g., several) positions, for example, a substitution, deletion, and/or insertion of one or more (e.g., several) amino acids. Preferably, amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellulolytic enhancing activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al, 1992, *J. Mol. Biol.* 224: 899-904; Wlodaver et al, 1992, *FEBS Lett.* 309: 59-64. The sequence identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

In an embodiment, the number of amino acid substitutions, deletions and/or insertions introduced into the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54 is up to 10, e.g., 1, 2, 3, 4, 5, 6, 7, 8, 9, or 10.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol* 3: 568-576; Svetina et al, 2000, *J. Biotechnol* 76: 245-251; Rasmussen-Wilson et al, 1997, *Appl. Environ. Microbiol* 63: 3488-3493; Ward et al, 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Cellulolytic Enhancing Activity

A polypeptide having cellulolytic enhancing activity of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

The polypeptide having cellulolytic enhancing activity of the present invention may be a fungal polypeptide. In another aspect, the polypeptide is a *Humicola insolens* polypeptide, e.g., a polypeptide obtained from *Humicola insolens* strain NN047338.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide having cellulolytic enhancing activity the present invention.

In a preferred aspect, the nucleotide sequence comprises or consists of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or the cDNA sequence thereof. In another preferred aspect, the nucleotide sequence comprises or consists of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or the cDNA sequence thereof.

The present invention also encompasses nucleotide sequences that encode polypeptides comprising or consisting of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54; or the mature polypeptide thereof; which differ from SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or the mature polypeptide coding sequence thereof, respectively, by virtue of the degeneracy of the genetic code. The present invention also relates to mutant polynucleotides comprising or consisting of at least one mutation in the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, in which the mutant nucleotide sequence encodes the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54, respectively.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al, 1990, *PCR: A Guide to Methods and Application*, Academic Press, New York. Other nucleic acid amplification procedures such as ligase chain reaction (LCR), ligation activated transcription (LAT) and nucleic acid sequence-based amplification (NASBA) may be used. The polynucleotides may be cloned from a strain of *Humicola*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO:

13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* crylllA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al, 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease WO 96/00787), *Fusarium venenatum* amyloglucosidase WO 00/56900), *Fusarium venenatum* Dania WO 00/56900), *Fusarium venenatum* Quinn WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus neutral* alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al, 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* crylIIA gene WO 94/25612) and a *Bacillus subtilis* SP82 gene (Hue et al, 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and tip operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al, 1991, *Gene* 98: 61-67; Cullen et al, 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol (Praha)* 49: 399-405), conjugation (see, e.g., Mazodier et al., 1989, *J. Bactetiol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus etyngii*, *Thielavia terrestris*, *Trametes villosa*, *Trametes versicolor*, *Trichoderma hatzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al, 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bactetiol* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In another aspect, the cell is a *Humicola* cell. In another aspect, the cell is a *Humicola insolens* cell. In another aspect, the cell is *Humicola insolens* strain NN047338.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cells may be cultivated by shake flask cultivation, and small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The resulting polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, the whole fermentation broth is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al, 1998, *J. Plant Physiol* 152: 708-711), a promoter from a seed oil body protein (Chen et al., 1998, *Plant Cell Physiol* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al, 1993, *Plant Physiol* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the polynucleotide encoding a polypeptide of the present invention. For instance, Xu et al, 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al, 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al, 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide having cellulolytic enhancing activity of the present invention under conditions conducive for production of the polypeptide; and (b) recovering the polypeptide.

Removal or Reduction of Cellulolytic Enhancing Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having cellulolytic enhancing activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo, or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially cellulolytic enhancing activity-free product are of particular interest in the production of eukaryotic polypeptides, in particular fungal proteins such as enzymes. The cellulolytic enhancing activity-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellulolytic enhancing activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or non-viable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in such a polypeptide. The term "enriched" indicates that the cellulolytic enhancing activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

In a preferable embodiment, the composition is a cellulolytic enhancing composition or a detergent composition.

Detergent Compositions

A polypeptide having cellulolytic enhancing activity of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide having cellulolytic enhancing activity as described herein. The detergent additive as well as the detergent composition may comprise one or more (e.g., several) enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME™ and CAREZYME™ (Novozymes A/S), CLAZINASE™, and PURADAX HA™ (Genencor International Inc.), and KAC-500(B)™ (Kao Corporation).

Proteases:

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more (e.g., several) of the following positions: 27, 36, 57, 76, 87, 97, 101, 104, 120, 123, 167, 170, 194, 206, 218, 222, 224, 235, and 274.

Preferred commercially available protease enzymes include ALCALASE™ SAVINASE™, PRIMASE™, DURALASE™, ESPERASE™, and KANNASE™ (Novozymes A/S), MAXATASE™, MAXACAL™, MAXAPEM™, PROPERASE™, PURAFECT™, PURAFECT OXP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 WO 95/06720 and WO 96/27002), *P. wisconsinensis* WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™, LIPEX™, and LIPOLASE ULTRA™ (Novozymes A/S).

Amylases:

Suitable amylases (alpha and/or beta) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more (e.g., several) of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes A/S), and RAPIDASE™ and PURASTAR™ (from Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes A/S).

The detergent enzyme(s) may be included in a detergent composition by adding separate additives containing one or more (e.g., several) enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

A detergent composition of the present invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more (e.g., several) surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more (e.g., several) polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a polypeptide having cellulolytic enhancing activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A polypeptide of the invention having cellulolytic enhancing activity may also be incorporated in the detergent formulations disclosed in WO 97/07202, which is hereby incorporated by reference.

Examples are given below of preferred uses of the compositions of the present invention. The dosage of the composition of the present invention and other conditions under which the composition is used may be determined on the basis of methods known in the art.

Uses

The present invention is also directed to the following methods for using the polypeptides having cellulolytic enhancing activity, or compositions thereof.

The present invention also relates to methods for degrading or converting a cellulosic material, comprising: treating the cellulosic material with an enzyme composition in the presence of a polypeptide having cellulolytic enhancing activity of the present invention. In one aspect, the methods further comprise recovering the degraded or converted cellulosic material. Soluble products of degradation or conversion of the cellulosic material can be separated from insoluble cellulosic material using methods known in the art such as, for example, centrifugation, filtration, or gravity settling.

The present invention also relates to methods of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of the present invention. In one aspect, the fermenting of the cellulosic material produces a fermentation product. In another aspect, the methods further comprise recovering the fermentation product from the fermentation.

The methods of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment.

In practicing the methods of the present invention, any pretreatment process known in the art can be used to disrupt plant cell wall components of the cellulosic material (Chandra et al., 2007, Substrate pretreatment: the key to effective enzymatic hydrolysis of lignocellulosics?, *Adv. Biochem. Engin./Biotechnol* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment:

In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment:

The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al, 2006, *Appl. Biochem. Biotechnol.* 129-132: 496-508; Varga et al., 2004, *Appl. Biochem. Biotechnol.* 113-116: 509-523; Sassner et al, 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al, 2004, *Bioresource Technol* 91: 179-188; Lee et al, 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al, 2005, *Bioresource Technol* 96: 1959-1966; Mosier et al., 2005, *Bioresource Technol* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol* 64: 139-151; Palonen et al, 2004, *Appl. Biochem. Biotechnol.* 117: 1-17; Varga et al, 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al, 2002, *Appl. Biochem. Biotechnol* 98: 23-35; Chundawat et al, 2007, *Biotechnol. Bioeng.* 96: 219-231; Alizadeh et al, 2005, *Appl. Biochem. Biotechnol* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment:

The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment:

The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having cellulolytic enhancing activity of the present invention. The enzyme components of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme components, i.e., optimal for the enzyme components. The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase). In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having cellulolytic enhancing activity depend on several factors including, but not limited to, the mixture of cellulolytic and/or hemicellulolytic enzyme components, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having cellulolytic enhancing activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having cellulolytic enhancing activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another aspect, the polypeptide is a *Streptococcus equisimilis, Streptococcus pyogenes, Streptococcus uberis,* or *Streptococcus* equi subsp. *Zooepidemicus* polypeptide having enzyme activity.

In another aspect, the polypeptide is a *Streptomyces achromogenes, Streptomyces avermitilis, Streptomyces coelicolor, Streptomyces griseus,* or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces,* or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdatium, Chrysosporium imps, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysospotium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III WO 05/093050); and *Thermobifida fusca* endoglucanase V WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al, 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM 324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II WO 2009/042871), *Thielavia hyrcanie* cellobiohydrolase II WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II WO 2010/057086).

Examples of beta-glucosidases useful in the present invention include, but are not limited to, beta-glucosidases from *Aspergillus* aculeatus (Kawaguchi et al., 1996, *Gene* 173: 287-288), *Aspergillus fumigatus* WO 2005/047499), *Aspergillus niger* (Dan et al, 2000, *J. Biol. Chem.* 275: 4973-4980), *Aspergillus oryzae* WO 2002/095014), *Penicillium brasilianum* IBT 20888 WO 2007/019442 and WO 2010/088387), *Thielavia terrestris* WO 2011/035029), and *Trichophaea saccata* WO 2007/019442).

The beta-glucosidase may be a fusion protein. In one aspect, the beta-glucosidase is an *Aspergillus oryzae* beta-glucosidase variant BG fusion protein WO 2008/057637) or an *Aspergillus oryzae* beta-glucosidase fusion protein WO 2008/057637).

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, Biochem. J. 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In one aspect, the GH61 polypeptide having cellulolytic enhancing activity is used in the presence of a soluble activating divalent metal cation according to WO 2008/151043, e.g., manganese sulfate.

In another aspect, the GH61 polypeptide having cellulolytic enhancing activity is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® Htec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from Aspergillus aculeatus (GeneSeqP: AAR63790; WO 94/21785), Aspergillus fumigatus WO 2006/078256), Penicillium pinophilum WO 2011/041405), Penicillium sp. WO 2010/126772), Thielavia terrestris NRRL 8126 WO 2009/079210), and Trichophaea saccata GH10 WO 2011/057083).

Examples of beta-xylosidases useful in the processes of the present invention include, but are not limited to, beta-xylosidases from Neurospora crassa (SwissProt accession number Q7SOW4), Trichoderma reesei (UniProtKB/TrEMBL accession number Q92458), and Taleromyces emersonfi (SwissProt accession number Q8×212).

Examples of acetylxylan esterases useful in the processes of the present invention include, but are not limited to, acetylxylan esterases from Aspergillus aculeatus WO 2010/108918), Chaetomium globosum (Uniprot accession number Q2GWX4), Chaetomium gracile (GeneSeqP accession number AAB82124), Humicola insolens DSM 1800 WO 2009/073709), Hypocrea jecorina WO 2005/001036), Myceliophtera thermophila WO 2010/014880), Neurospora crassa (UniProt accession number q7s259), Phaeosphaeria nodorum (Uniprot accession number QOUHJI), and Thielavia terrestris NRRL 8126 WO 2009/042846).

Examples of feruloyl esterases (ferulic acid esterases) useful in the processes of the present invention include, but are not limited to, feruloyl esterases form *Humicola insolens* DSM 1800 WO 2009/076122), *Neosartorya fischeri* (UniProt Accession number A1D9T4), *Neurospora crassa* (UniProt accession number Q9HGR3), *Penicillium aurantiogriseum* WO 2009/127729), and *Thielavia terrestris* WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 WO 2006/114094 and WO 2009/073383), and *M. giganteus* WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* WO 2010/014706), *Penicillium aurantiogriseum* WO 2009/068565), *Talaromyces emersonii* (UniProt accession number Q8x211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol*, 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida* blankii. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al, 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximate $10^5$ to $10^{12}$, preferably from approximate $10^7$ to $10^{10}$, more preferably approximate $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al, Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products.

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptides

The present invention also relates to an isolated polynucleotide encoding a signal peptide comprising or consisting of amino acids 1 to 17 of SEQ ID NO: 2, amino acids 1 to 16 of SEQ ID NO: 4, amino acids 1 to 19 of SEQ ID NO: 6, amino acids 1 to 27 of SEQ ID NO: 8, amino acids 1 to 15 of SEQ ID NO: 10, amino acids 1 to 20 of SEQ ID NO: 12, amino acids 1 to 21 of SEQ ID NO: 14, amino acids 1 to 15 of SEQ ID NO: 16, amino acids 1 to 19 of SEQ ID NO: 18, or amino acids 1 to 17 of SEQ ID NO: 20, amino acids 1 to 16 of SEQ ID NO: 22, amino acids 1 to 21 of SEQ ID NO: 24, amino acids 1 to 17 of SEQ ID NO: 26, amino acids 1 to 20 of SEQ ID NO: 28, or amino acids 1 to 20 of SEQ ID NO: 30, amino acids 1 to 19 of SEQ ID NO: 32, amino acids 1 to 15 of SEQ ID NO: 34, amino acids 1 to 18 of SEQ ID NO: 36, amino acids 1 to 19 of SEQ ID NO: 38, or amino acids 1 to 18 of SEQ ID NO: 40, amino acids 1 to 19 of SEQ ID NO: 42, amino acids 1 to 21 of SEQ ID NO: 44, amino acids 1 to 19 of SEQ ID NO: 46, amino acids 1 to 18 of SEQ ID NO: 48, or amino acids 1 to 17 of SEQ ID NO: 50, amino acids 1 to 20 of SEQ ID NO: 52, or amino acids 1 to 21 of SEQ ID NO: 54. The polynucleotides may further comprise a gene encoding a protein, which is operably linked to the signal peptide. The protein is preferably foreign to the signal peptide.

In one aspect, the polynucleotides for the signal peptides are nucleotides 1 to 51 of SEQ ID NO: 1, nucleotides 1 to 48 of SEQ ID NO: 3, nucleotides 1 to 57 of SEQ ID NO: 5, nucleotides 1 to 81 of SEQ ID NO: 7, nucleotides 1 to 45 of SEQ ID NO: 9, nucleotides 1 to 60 of SEQ ID NO: 11, nucleotides 1 to 63 of SEQ ID NO: 13, nucleotides 1 to 45 of SEQ ID NO: 15, nucleotides 1 to 57 of SEQ ID NO: 17, nucleotides 1 to 51 of SEQ ID NO: 19, nucleotides 1 to 48 of SEQ ID NO: 21, nucleotides 1 to 63 of SEQ ID NO: 23, nucleotides 1 to 51 of SEQ ID NO: 25, nucleotides 1 to 60 of SEQ ID NO: 27, nucleotides 1 to 60 of SEQ ID NO: 29, nucleotides 1 to 57 of SEQ ID NO: 31, nucleotides 1 to 45 of SEQ ID NO: 33, nucleotides 1 to 54 of SEQ ID NO: 35, nucleotides 1 to 57 of SEQ ID NO: 37, nucleotides 1 to 54 of SEQ ID NO: 39, nucleotides 1 to 57 of SEQ ID NO: 41, nucleotides 1 to 63 of SEQ ID NO: 43, nucleotides 1 to 57 of SEQ ID NO: 45, nucleotides 1 to 54 of SEQ ID NO: 47, nucleotides 1 to 51 of SEQ ID NO: 49, nucleotides 1 to 60 of SEQ ID NO: 51, or nucleotides 1 to 63 of SEQ ID NO: 53.

The present invention also relates to nucleic acid constructs, expression vectors and recombinant host cells comprising such polynucleotides.

The present invention also relates to methods of producing a protein, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

EXAMPLES

Strain

The fungal strain NN047338 was isolated from a soil sample collected from Yunnan, China by the dilution plate method with PDA medium at 45° C. It was then purified by transferring a single conidium onto a YG agar plate. The strain NN047338 was identified as *Humicola insolens* Cooney & R. Emers., based on both morphological characteristics and ITS rDNA sequence.

Media

PDA medium was composed of 39 grams of potato dextrose agar and deionized water to 1 liter.

YG agar plates were composed of 5.0 g of yeast extract, 10.0 g of glucose, 20.0 g of agar, and deionized water to 1 liter.

YPM medium contained 1% yeast extract, 2% of peptone, and 2% of maltose in deionized water.

YPG medium contained 0.4% yeast extract, 0.1% of $KH_2PO_4$, 0.05% of $MgSO_4.7H_2O$, and 1.5% of glucose in deionized water.

Example 1

*Humicola insolens* Genomic DNA Extraction

*Humicola insolens* strain NN047338 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH®(Calbiochem, La Jolla, Calif., USA) and frozen in liquid nitrogen. Frozen mycelia were ground, by a mortar and a pestle, to a fine powder, and genomic DNA was isolated using a DNEASY® Plant Maxi Kit (QIAGEN Inc., Valencia, Calif., USA).

Example 2

Genome Sequencing, Assembly and Annotation

The extracted genomic DNA samples were delivered to Beijing Genome Institute (BGI, Shenzhen, China) for genome sequencing using ILLUMINA® GA2 System (Illumina, Inc., San Diego, Calif., USA). The raw reads were assembled at BGI using SOAPdenovo (Li et al., 2010, *Genome Research* 20(2): 265-72). The assembled sequences were analyzed using standard bioinformatics methods for gene finding and functional prediction. Briefly, geneID (Parra et al., 2000, *Genome Research* 10(4): 511-515) was used for gene prediction. Blastall version 2.2.10 (Altschul et al., 1990, *J. Mol. Biol.* 215 (3): 403-410; National Center for Biotechnology Information (NCBI), Bethesda, Md., USA) and HMMER version 2.1.1 (National Center for Biotechnology Information (NCBI), Bethesda, Md., USA) were used to predict function based on structural homology. The family GH61 gene sequences were identified directly by analysis of the Blast results. The Agene program (Munch and Krogh, 2006, *BMC Bioinformatics* 7: 263) and SignalP program (Nielsen et al., 1997, *Protein Engineering* 10:1-6) were used to identify starting codons. SignalP program was further used to predict the signal peptides. Pepstats (Rice et al., 2000, *Trends Genet.* 16(6): 276-277) was used to estimate the molecular weights based on the deduced amino acid sequences.

Example 3

Construction of Expression Vector

Based on GH61 gene sequences as identified in Example 2, oligonucleotide primers were designed to amplify the GH61 genes from genomic DNA of *Humicola insolens* NN047338. Primers as shown in table 1 were synthesized by Invitrogen (Invitrogen, Beijing, China).

TABLE 1

| primers | | |
|---|---|---|
| Seq1_forward | ACACAACTGGGGATCC ACC atgaagctcagcgttgtcctcac | SEQ ID NO. 55 |
| seq1_reverse | GTCACCCTCTAGATCTtcagcacgtctcaaccggc | SEQ ID NO. 56 |
| seq2_forward | ACACAACTGGGGATCC ACC atgcgccccttcctcg | SEQ ID NO. 57 |
| seq2_reverse | GTCACCCTCTAGATCTttactcagactcggggcacgtc | SEQ ID NO. 58 |
| seq3_forward | ACACAACTGGGGATCC ACC atgagactctccctgacaaccctc | SEQ ID NO. 59 |
| seq3_reverse | GTCACCCTCTAGATCTcagcactgaatcggctcc | SEQ ID NO. 60 |
| seq4_forward | ACACAACTGGGGATCC ACC atgggaccgacctgggc | SEQ ID NO. 61 |
| seq4_reverse | GTCACCCTCTAGATCTcacccccgtccacaccg | SEQ ID NO. 62 |
| seq5_forward | ACACAACTGGGGATCC ACC atgaaggccctcaccctcctc | SEQ ID NO. 63 |
| seq5_reverse | GTCACCCTCTAGATCTttacaagcactgcgaataccacg | SEQ ID NO. 64 |
| seq6_forward | ACACAACTGGGGATCC ACC atggctcccaagacctcgac | SEQ ID NO. 65 |
| seq6_reverse | GTCACCCTCTAGATCTttagatgcactgcgagtaccagtcg | SEQ ID NO. 66 |
| seq7_forward | ACACAACTGGGGATCC ACC atgtatcttttacctatcgccgcg | SEQ ID NO. 67 |
| seq7_reverse | GTCACCCTCTAGATCTttatccgtgttggttcaccttgg | SEQ ID NO. 68 |
| seq8_forward | ACACAACTGGGGATCC ACC atgaagctcctcgctcctctgat | SEQ ID NO. 69 |
| seq8_reverse | GTCACCCTCTAGATCTttagcacttgaagacatcgggg | SEQ ID NO. 70 |
| seq9_forward | ACACAACTGGGGATCC ACC atgaagctcctctcaaccctcg | SEQ ID NO. 71 |
| seq9_reverse | GTCACCCTCTAGATCTttagttgccatcccacaccttg | SEQ ID NO. 72 |
| seq10_forward | ACACAACTGGGGATCC ACC atgctgggaagcgctcttct | SEQ ID NO. 73 |
| seq10_reverse | GTCACCCTCTAGATCTttagcactggaagaccgggg | SEQ ID NO. 74 |
| seq11_forward | ACACAACTGGGGATCC ACC atgaagctgcttcctgggttg | SEQ ID NO. 75 |
| seq11_reverse | GTCACCCTCTAGATCTcagccacgccacacgg | SEQ ID NO. 76 |
| seq12_forward | ACACAACTGGGGATCC ACC atgctcctgaactcggtcatcg | SEQ ID NO. 77 |
| seq12_reverse | GTCACCCTCTAGATCTttactcgccgcgccaga | SEQ ID NO. 78 |
| seq13_forward | ACACAACTGGGGATCC ACC atgaagctcaccacctccatcg | SEQ ID NO. 79 |
| seq13_reverse | GTCACCCTCTAGATCTcagcacttcaccggcgc | SEQ ID NO. 80 |
| seq14_forward | ACACAACTGGGGATCC ACC atgaagactctcgcatccgcc | SEQ ID NO. 81 |
| seq14_reverse | GTCACCCTCTAGATCTcagaaaaagctcccatcaatgaca | SEQ ID NO. 82 |
| seq15_forward | ACACAACTGGGGATCC ACC atgcctcgcttcaccaagtcc | SEQ ID NO. 83 |
| seq15_reverse | GTCACCCTCTAGATCTtcaagcaaccacctgcacac | SEQ ID NO. 84 |

TABLE 1-continued primers

| | | |
|---|---|---|
| seq16_forward | ACACAACTGGGGATCC ACC atgaagggacttctcagcatcgc | SEQ ID NO. 85 |
| seq16_reverse | GTCACCCTCTAGATCTttagatgcactgagaatagtaagcgttctg | SEQ ID NO. 86 |
| seq17_forward | ACACAACTGGGGATCC ACC atgaggcccttctcactcgtc | SEQ ID NO. 87 |
| seq17_reverse | GTCACCCTCTAGATCTctaaggcgtacactgcgagtaccagt | SEQ ID NO. 88 |
| seq18_forward | ACACAACTGGGGATCCACC atggtgttgcggtctctctctatcct | SEQ ID NO. 89 |
| seq18_reverse | GTCACCCTCTAGATCTtcataacgtcattatcgttgtttgcgt | SEQ ID NO. 90 |
| seq19_forward | ACACAACTGGGGATCC ACC atgaggaccgtcttcgccg | SEQ ID NO. 91 |
| seq19_reverse | GTCACCCTCTAGATCTttagaaagcaggctggcactgag | SEQ ID NO. 92 |
| seq20_forward | ACACAACTGGGGATCC ACC atgaggctcccccaagtgg | SEQ ID NO. 93 |
| seq20_reverse | GTCACCCTCTAGATCTttagccaccaatcgagtcaaagtactc | SEQ ID NO. 94 |
| seq21_forward | ACACAACTGGGGATCC ACC atgcacgtccagtctctccttg | SEQ ID NO. 95 |
| seq21_reverse | GTCACCCTCTAGATCTttacaggcactgcgagtaccagtc | SEQ ID NO. 96 |
| seq22_forward | ACACAACTGGGGATCC ACC atgccaccaccactactggcc | SEQ ID NO. 97 |
| seq22_reverse | GTCACCCTCTAGATCTcatggcctacccatctcaaatctt | SEQ ID NO. 98 |
| seq23_forward | ACACAACTGGGGATCC ACC atgaagtccctgacctacgccg | SEQ ID NO. 99 |
| seq23_reverse | GTCACCCTCTAGATCTttacacgcactgagagtaccactggtt | SEQ ID NO. 100 |
| seq24_forward | ACACAACTGGGGATCC ACC atgaagctcctcctccccg | SEQ ID NO. 101 |
| seq24_reverse | GTCACCCTCTAGATCTcacgaggttgatatggagttgctc | SEQ ID NO. 102 |
| seq25_forward | ACACAACTGGGGATCC ACC atgcgttctgtttcccttcttgc | SEQ ID NO. 103 |
| seq25_reverse | GTCACCCTCTAGATCTttaaaaatcgcgcgggtgttt | SEQ ID NO. 104 |
| seq26_forward | ACACAACTGGGGATCC ACC atgttcttccgcaacgccg | SEQ ID NO. 105 |
| seq26_reverse | GTCACCCTCTAGATCTcaagccttgggctcctcac | SEQ ID NO. 106 |
| seq27_forward | ACACAACTGGGGATCC ACC atggctcatccatgggcac | SEQ ID NO. 107 |
| seq27_reverse | GTCACCCTCTAGATCTcacttgtaccggtagagataagcacc | SEQ ID NO. 108 |

Lowercase characters represent the coding regions of the genes, while capitalized parts represents overhang to the pPFJO355 vector (US Patent Application 2010306879). Undigested pPFJO355 vector was shown in FIG. 2.

For each gene, 20 picomoles of each of the forward and reverse primer was used in a PCR reaction with *Humicola insolens* NN047338 genomic DNA, 10 μl of 5×GC Reaction Buffer (Finnzymes Oy, Espoo, Finland), 1.5 μl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 μl. The amplification was performed using a C1000 Thermal Cycler (Bio-Rad Laboratories, Hercules, Calif., USA) programmed for denaturing at 98° C. for 1 minutes; 7 cycles of denaturing at 98° C. for 15 seconds, annealing at 68° C. for 30 seconds, with 1° C. decrease per cycle and elongation at 72° C. for 60 seconds; and another 21 cycles each at 98° C. for 15 seconds, 62° C. for 30 seconds and 65° C. for 60 seconds; final extension at 72° C. for 5 minutes. The heat block then went to a 4° C. soak cycle.

The reaction products were isolated by 1.0% agarose gel electrophoresis using 90 mM Tris-borate and 1 mM EDTA (TBE) buffer. A single band was seen around the expected size for all sequences except sequence 2. For the remaining 26 sequences, each band was excised from the gel, and purified using an ILLUSTRA™ GFX™ PCR DNA and Gel Band Purification Kit (GE Healthcare, Buckinghamshire, UK) according to the manufacturer's instructions.

pPFJO355 vector was digested with BamH I and Bgl II, isolated by 1.0% agarose gel electrophoresis using TBE buffer, and purified using an ILLUSTRA™ GFX™ PCR DNA and Gel Band Purification Kit according to the manufacturer's instructions.

The gene fragments and the digested vector were ligated together using an IN-FUSION™ Dry Down PCR Cloning Kit (Clontech Laboratories, Mountain View, Calif., USA) resulting in plasmids pGH61seq1, pGH61seq3, pGH61seq4, pGH61seq5, pGH61seq6, pGH61seq7, pGH61seq8, pGH61seq9, pGH61seq10, pGH61seq11, pGH61seq12, pGH61seq13, pGH61seq14, pGH61seq15, pGH61seq16, pGH61seq17, pGH61seq18, pGH61seq19, pGH61seq20, pGH61seq21, pGH61seq22, pGH61seq23, pGH61seq24, pGH61seq25, pGH61seq26 and pGH61seq27 in which transcription of the cloned genes were under the control of a promoter from the gene for *Aspergillus oryzae* alpha-amylase. GH61 genes were inserted between the BamH I restriction site and the Bgl II restriction site of pPFJO355 vector as shown in FIG. 2. The cloning operation was conducted according to the instructions of the IN-FUSION™ Dry Down PCR Cloning Kit. In brief, 30 ng of pPFJO355 digested with BamH I and Bgl II, and 60 ng of the *Humicola Insolens* NN047338 purified PCR product were added to the reaction vial and resuspended in a final volume of 10 µl with addition of deionized water. The reactions were incubated at 37° C. for 15 minutes and then 50° C. for 15 minutes. Three µl of the products were used to transform *E. coli* TOP10 competent cells (TIANGEN Biotech (Beijing) Co. Ltd., Beijing, China). *E. coli* transformants containing plasmid vectors of the *Humicola insolens* GH61 genes were detected by colony PCR and verified by DNA sequencing at SinoGenoMax (SinoGenoMax Company Limited, Beijing, China). Colonies were grown overnight at 37° C., and plasmid DNA was prepared using a QIAprep Spin Miniprep Kit (QIAGEN Inc., Valencia, Calif., USA).

Example 4

Transformation of *Aspergillus oryzae*

*Aspergillus oryzae* HowB101 WO 95/35385 Example 1) protoplasts were prepared according to the method of Christensen et al., 1988, *Bio/Technology* 6: 1419-1422.

The transformation of *Aspergillus oryzae* HowB101 with pGH61seq1, pGH61seq3, pGH61seq4, pGH61seq5, pGH61seq6, pGH61seq7, pGH61seq8, pGH61seq9, pGH61seq10, pGH61seq11, pGH61seq12, pGH61seq13, pGH61seq14, pGH61seq15, pGH61seq16, pGH61seq17, pGH61seq18, pGH61seq19, pGH61seq20, pGH61seq21, pGH61seq22, pGH61seq23, pGH61seq24, pGH61seq25, pGH61seq26 and pGH61seq27, respectively, yielded various numbers of transformants. Eight transformants were isolated for each gene and transferred to individual Minimal medium in 24 well plates.

Four transformants for each gene were inoculated separately into 3 ml YPM medium in a 24-well plate and incubated at 30° C., 150 rpm. After 3 days of incubation, 20 µl of supernatant from each culture were analyzed on NuPAGE® Novex 4-12% Bis-Tris Gel with 50 mM 2-(N-morpholino)ethanesulfonic acid (MES) (Invitrogen Corporation, Carlsbad, Calif., USA) according to the manufacturer's instructions. The resulting gel was stained with INSTANTBLUE™ (Expedeon Ltd., Babraham Cambridge, UK). SDS-PAGE profiles of the cultures showed expression bands similar to what was expected from the molecular mass as calculated by PepStats for transformants from pGH61seq1, pGH61seq3, pGH61seq4, pGH61seq5, pGH61seq6, pGH61seq7, pGH61seq8, pGH61seq9, pGH61seq11, pGH61seq12, pGH61seq13, pGH61seq14, pGH61seq15, pGH61seq16, pGH61seq17, pGH61seq19, pGH61seq20, pGH61seq21, pGH61seq22, pGH61seq23, pGH61seq25 and pGH61seq26.

Example 5

Fermentation

A slant of one transformant from each of the remaining 22 genes was washed with 10 ml of YPM medium and inoculated into between 4 and 8 two-liter flasks (see table 2) containing 400 ml of YPM medium. The culture was grown at 30° C., 80 rpm and harvested on day 3.

TABLE 2 flasks and transformants

| | Flasks | Transformants |
|---|---|---|
| Sequence 1 | 8 | T1 |
| Sequence 3 | 6 | T3 |
| Sequence 4 | 4 | T4 |
| Sequence 5 | 8 | T5 |
| Sequence 6 | 4 | T6 |
| Sequence 7 | 6 | T7 |
| Sequence 8 | 4 | T8 |
| Sequence 9 | 6 | T9 |
| Sequence 11 | 4 | T11 |
| Sequence 12 | 4 | T12 |
| Sequence 13 | 6 | T13 |
| Sequence 14 | 4 | T14 |
| Sequence 15 | 6 | T15 |
| Sequence 16 | 6 | T16 |
| Sequence 17 | 4 | T17 |
| Sequence 19 | 8 | T19 |
| Sequence 20 | 6 | T20 |
| Sequence 21 | 4 | T21 |
| Sequence 22 | 8 | T22 |
| Sequence 23 | 4 | T23 |
| Sequence 25 | 4 | T25 |
| Sequence 26 | 6 | T26 |

Protein was precipitated by adding to the culture broth $(Na_4)_2SO_4$ to a concentration of 561 g/L. The protein was collected after centrifugation and filtered through a 0.45 µm DURAPORE® Membrane (Millipore, Bedford, Mass., USA). The resultant filtrate was used in the following protein purification.

Example 6

Protein Purification of GH61 Polypeptide

Protein purification was carried out using AKTA Purifier 100 systems (GE Healthcare, Waukesha, Wis., USA) with SP Sepharose™ Fast Flow (SPFF) columns (GE Healthcare, Waukesha, Wis., USA), Q Sepharose® Fast Flow (QFF) columns (GE Healthcare, Waukesha, Wis., USA) or Hydrophobic Interaction Chromatography (HIC) columns (GE Healthcare, Waukesha, Wis., USA). In all purifications, buffer A was always equivalent to dialysis buffer (specified below). Columns were washed with 2 column volumes (CV) buffer A after sample loading. Before the gradient was applied, elute from the column during sample loading and column washes was collected and denoted as flow-through (FT). While applying the gradient, elute was collected in volumes each of 10 ml, and denoted as fractions. Fraction 1 thus contained the first 10 ml collected during application of the gradient; fraction 2 contained the next 10 ml, etc. The purifications for each protein were specified as follows.

T7 filtrate was dialyzed against 20 mM Bis-Tris buffer pH 5.0 and a 90 ml sample was loaded onto an SPFF column. Buffer B was equivalent to buffer A with inclusion of 1 M NaCl. A gradient was applied with inclusion of buffer B from 0% to 50% spanning 13 CV, 50-80% spanning 3CV, and 80-100% spanning 2CV. Fractions 5-9 were dialyzed against 20 mM Bis-Tris pH 5.0 and loaded onto an SPFF column. Buffer B was equivalent to buffer A with inclusion of 1 M NaCl. A gradient was applied with inclusion of buffer B from 0-15% spanning 13 CV, 15-50% spanning 3 CV, and 50-100% spanning 5 CV, and fractions 7-11 were collected as target protein.

T8 filtrate was dialyzed against 20 mM Bis-Tris buffer pH 5.0 and a 75 ml sample was loaded onto a QFF column. Buffer B was equivalent to buffer A with inclusion of 1 M NaCl. FT from sample loading and column washes were collected as target protein.

T6 filtrate was dialyzed against 20 mM Bis-Tris buffer pH 5.0 and 75 ml sample was loaded onto an SPFF column. Buffer B was equivalent to buffer A with inclusion of 1 M NaCl. A gradient was applied with inclusion of buffer B from 0 to 20% spanning 13 CV, 20-50% spanning 4 CV, and 50-100% spanning 5 CV. Fractions 5-9 were collected as target protein. FT was dialyzed against 20 mM Bis-Tris pH 5.0 and loaded onto a QFF column. Buffer B was equivalent to buffer A with inclusion of 1 M NaCl. Flow-through was collected and batched with collected Fractions 5-9 from the previous purification, as target protein.

T1 filtrate was dialyzed against 20 mM Tris/HCl buffer pH 7.0 and a 90 ml sample was loaded onto a QFF column. Buffer B was equivalent to buffer A with inclusion of 1 M NaCl. Flow-through was collected as target protein.

T4 filtrate was dialyzed against 20 mM Bis-Tris buffer pH 6.0 and 50 ml sample was loaded onto a QFF column. Buffer B was equivalent to buffer A with inclusion of 1 M NaCl. A gradient was applied with inclusion of buffer B from 0 to 20% spanning 13 CV, 20-50% spanning 4 CV, and 50-100% spanning 5 CV. Fractions 35-44 were collected and then $(NH_4)_2SO_4$ was added to a final concentration of 1.2 M. A 100 ml sample was loaded onto an HIC column. Buffer B was equivalent to buffer A with inclusion of 1.2 M $(NH_4)_2SO_4$. Buffer A from 100 to 0% inclusion of buffer B was applied spanning 20 CV. Fractions 35-44 were collected as target protein.

T3 filtrate was dialyzed against 20 mM Bis-Tris buffer pH 6.0 and a 75 ml sample was loaded onto a QFF column. Buffer B was equivalent to buffer A with inclusion of 1 M NaCl. A gradient was applied with inclusion of buffer B from 0 to 20% spanning 13 CV, 20-50% spanning 4 CV, and 50-100% spanning 5 CV. Flow-through was collected as target protein. Due to heavy aggregation at low pH, the buffer was changed to glycine buffer pH 10 by dialysis.

T9 filtrate was dialyzed against 20 mM Bis-Tris buffer pH 6.0 and 80 ml sample was loaded onto a QFF column. Buffer B was equivalent to buffer A with inclusion of 1 M NaCl. A gradient was applied with inclusion of buffer B from 0 to 20% spanning 13 CV, 20-50% spanning 4 CV, and 50-100% spanning 5 CV. Flow-through and fractions 4-15 were batched and then $(NH_4)_2SO_4$ was added to a final concentration of 1.2 M. A 275 ml sample was loaded onto an HIC column. Buffer B was equivalent to buffer A with inclusion of 1.2 M $(NH_4)_2SO_4$. A gradient from 100 to 0% inclusion of buffer B was applied spanning 20 CV. Fractions 16-49 were collected as target protein.

T11 filtrate was dialyzed against 20 mM Tris/HCl buffer pH 7.5 and a 58 ml sample was loaded onto a QFF column. Buffer B was equivalent to buffer A with inclusion of 1 M NaCl. Flow-through was collected as target protein.

T5 filtrate was dialyzed against 20 mM Bis-Tris buffer pH 5.0 and a 90 ml sample was loaded onto a QFF column. Buffer B was equivalent to buffer A with inclusion of 1 M NaCl. Flow-through was collected as target protein.

T14 filtrate was dialyzed against 20 mM NaAc buffer pH 5.0 and a 75 ml sample was loaded onto a QFF column. Buffer B was equivalent to buffer A with inclusion of 1 M NaCl. Flow-through was collected as target protein.

T16 filtrate was dialyzed against 20 mM Bis-Tris buffer pH 5.5 and an 80 ml sample was loaded onto a QFF column. Buffer B was equivalent to buffer A with inclusion of 1 M NaCl. Flow-through was collected and then $(NH_4)_2SO_4$ was added to a final concentration of 1.2 M. A 155 ml sample was loaded onto an HIC column. Buffer B was equivalent to buffer A with inclusion of 1.2 M $(NH_4)_2SO_4$. A gradient from 100 to 0% inclusion of buffer B was applied spanning 20 CV. Fractions 32-60 were collected as target protein.

T25 filtrate was dialyzed against 20 mM Tris/HCl buffer pH 7.5 and a 110 ml sample was loaded onto a QFF column. Buffer B was equivalent to buffer A with inclusion of 1 M NaCl. A gradient was applied with inclusion of buffer B from 0-20% spanning 13 CV, 20-50% spanning 4 CV, and 50-100% spanning 5 CV. Fractions 10-16 were collected as target protein.

T20 filtrate was dialyzed against 20 mM Bis-Tris buffer pH 6.5 and a 105 ml sample was loaded onto a QFF column. Buffer B was equivalent to buffer A with inclusion of 1 M NaCl. A gradient was applied with inclusion of buffer B from 0 to 20% spanning 13 CV, 20-50% spanning 4 CV, and 50-100% spanning 5 CV. Fractions 27-39 were collected and then $(NH_4)_2SO_4$ was added to a final concentration of 1.2 M. A 125 ml sample was loaded onto an HIC column. Buffer B was equivalent to buffer A with inclusion of 1.2 M $(NH_4)_2SO_4$. A gradient from 100 to 0% inclusion of buffer B was applied spanning 20 CV. Column was subsequently washed with 10CV buffer A. Fractions 54-61 plus elute from washing were collected as target protein.

T26 filtrate was dialyzed against 20 mM Tris/HCl buffer pH 7.5 and a 50 ml sample was loaded onto a QFF column. Buffer B was equivalent to buffer A with inclusion of 1 M NaCl. A gradient was applied with inclusion of buffer B from 0 to 20% spanning 13 CV, 20-50% spanning 4 CV, and 50-100% spanning 5 CV. Fractions 8-16 were collected and then $(NH_4)_2SO_4$ was added to a final concentration of 1.2 M. An 85 ml sample was loaded onto an HIC column. Buffer B was equivalent to buffer A with inclusion of 1.2 M $(NH_4)_2SO_4$. A gradient from 100 to 0% inclusion of buffer B was applied spanning 20 CV. Fractions 9-27 were collected as target protein.

T17 filtrate was dialyzed against 20 mM Bis-Tris buffer pH 5.5 and a 50 ml sample was loaded onto a QFF column. Buffer B was equivalent to buffer A with inclusion of 1 M NaCl. Flow-through was collected as target protein.

T21 filtrate was dialyzed against 20 mM Bis-Tris buffer pH 5.5 and a 60 ml sample was loaded onto a QFF column. Buffer B was equivalent to buffer A with inclusion of 1 M NaCl. Flow-through was collected as target protein.

T23 filtrate was dialyzed against 20 mM Bis-Tris buffer pH 5.5 and a 55 ml sample was loaded onto a QFF column. Buffer B was equivalent to buffer A with inclusion of 1 M NaCl. Flow-through was collected as target protein.

T19 filtrate was dialyzed against 20 mM Tris/HCl buffer pH 7.0 and a 90 ml sample was loaded onto a QFF column. Buffer B was equivalent to buffer A with inclusion of 1 M NaCl. A gradient was applied with inclusion of buffer B from 0-20% spanning 13 CV, 20-50% spanning 4 CV, and 50-100% spanning 5 CV. Flow-through and fractions 5-16 were batched and then $(NH_4)_2SO_4$ was added to a final concentration of 1.2 M. 300 ml sample was loaded onto a HIC column. Buffer B was equivalent to buffer A with inclusion of 1.2 M $(NH_4)_2SO_4$. A gradient from 100 to 0% inclusion of buffer B was applied spanning 20 CV. Fractions 49-70 were batched and dialyzed against 20 mM Tris/HCL buffer pH 7.5. A 255 ml sample was loaded onto a QFF column. Buffer B was equivalent to buffer A with inclusion of 1 M NaCl. A gradient was applied with inclusion of buffer B from 0-12% spanning 10 CV, 12-50% spanning 4 CV, and 50-100% spanning 3 CV. Fractions 2-24 were collected as target protein.

T22 filtrate was dialyzed against 20 mM Bis-Tris buffer pH 5.5 and a 60 ml sample was loaded onto a QFF column. Buffer B was equivalent to buffer A with inclusion of 1 M NaCl. Flow-through was collected as target protein.

T13 filtrate was dialyzed against 20 mM Bis-Tris buffer pH 6.0 and a 40 ml sample was loaded onto a QFF column. Buffer B was equivalent to buffer A with inclusion of 1 M NaCl. Flow-through was collected as target protein.

T12 filtrate was dialyzed against 20 mM Bis-Tris buffer pH 6.0 and a 60 ml sample was loaded onto an SPFF column. Buffer B was equivalent to buffer A with inclusion of 1 M NaCl. Flow-through was loaded onto a QFF column with equivalent buffers. Flow-through was collected and $(NH_4)_2SO_4$ was added to a final concentration of 1.2 M before loaded onto an HIC column. Flow-through was collected as target protein.

T15 filtrate was dialyzed against 20 mM Tris-Cl buffer pH 7.5 and an 80 ml sample was loaded onto a QFF column. Buffer B was equivalent to buffer A with inclusion of 1 M NaCl. A gradient was applied with inclusion of buffer B from 0 to 20% spanning 13 CV, 20-50% spanning 7 CV, and 50-100% spanning 4 CV. Fractions 22-28 were dialyzed against 20 mM Tris-Cl buffer pH 7.5 and loaded onto a QFF column with equivalent buffers. A gradient was applied with inclusion of buffer B from 0 to 8% spanning 4 CV, 8-14% spanning 11 CV, and 50-100% spanning 8 CV. Fractions 32-50 were collected as target protein.

Example 7

Pretreatment of Corn Stover

Corn stover was pretreated at the U.S. Department of Energy National Renewable

Energy Laboratory (NREL) using 1.4% (w/v) sulfuric acid for 8 minutes at 165° C. and 107 psi. The water-insoluble solids in the pretreated corn stover contained 57.5% cellulose, 4.6% hemicelluloses, and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

The pretreated corn stover (PCS) was milled (dry weight 32.35%) in a Cosmos ICMG 40 et multi-utility grinder (EssEmm Corporation, Tamil Nadu, India), then adjusted to pH 5.0 by repeated addition of 10 N NaOH in aliquots of a few milliliters, followed by thorough mixing and incubation at room temperature for approximately 1 hour. The pH was confirmed after overnight incubation at 4° C., and the pH-adjusted corn stover was autoclaved for 20 minutes at approximately 120° C., and then stored at 4° C. to minimize the risk of microbial contamination. The dry weight of the pretreated corn stover was 33% TS (total solids), which was confirmed before each use.

Example 8

Preparation of Phosphoric Acid Swollen Cellulose (PASC)

A 1% phosphoric acid swollen cellulose (PASC) slurry was prepared from AVICEL® PH101 (Sigma-Aldrich, St. Louis, Mo., USA) using the prortocol described by Zhang et al., 2006, *Biomacromolecules* 7: 644-648.

Example 9

Hydrolysis Assay

The cellulolytic enhancing effect of the GH61 polypeptides was evaluated according to the procedures described below.

The hydrolysis of PASC was conducted using 2.0 ml deep-well plates (Thermo Scientific, Asheville, N.C., USA) in a total reaction volume of 1.0 ml. Each hydrolysis was performed with 5 mg of PASC per ml of 50 mM sodium acetate pH 5.0 buffer containing 2 mg of *Aspergillus oryzae* GH3A beta-glucosidase WO 2002/095014) per gram of cellulose, with or without 60 mg of GH61 polypeptide per gram of cellulose, or with or without 20 mg of GH61 polypeptide per gram of cellulose, with 10 mM pyrogallol (Fluka, Milwaukee, Wis., USA) plus 10 μM copper sulfate. The plates were mixed thoroughly, sealed, and incubated at 50° C. for 3 days 4 days in an Innova 40 incubator (New Brunswich Scientific, Enfield, Conn., USA). All experiments were performed in triplicate.

A blend of CELLUCLAST® 1.5L (Novozymes A/S, Bagsværd, Denmark) in the presence of 2-3% of total protein weight *Aspergillus fumigatus* beta-glucosidase WO 2005/047499) was used as the cellulase preparation. The cellulase preparation is designated herein in the Examples as the "cellulase composition".

The hydrolysis of PCS was conducted using 2.0 ml deep-well plates (Axygen Scientific, Union City, Calif., USA) in a total reaction volume of 1.0 ml. Each hydrolysis was performed with 50 mg of PCS (total insoluble solids; 27.0 mg of cellulose) per ml of 50 mM sodium acetate pH 5.0 buffer containing the cellulase composition at 2 mg protein per gram of cellulose, plus 10 μM copper sulfate and 10 mM pyrogallol, and with and without the GH61 protein having cellulolytic enhancing activity at 6 mg per g cellulose. The plates were mixed thoroughly, sealed, and incubated at 50° C. for 3 days in an Innova 40 incubator (New Brunswich Scientific, Enfield, Conn., USA). All experiments were performed in triplicate.

Following hydrolysis, samples were transferred to 96 well MultiScreen HTS™ Nucleic A filter plates (Millipore, Billerica, Mass., USA) and filtered by vacuum using a M2 2C diaphragm vacuum pump (Vacuubrand GMBH+ CO KG, Wertheim, Germany). Filtered sample was mixed in a 1:4 ratio with 5 mM $H_2SO_4$ and then analyzed for glucose content on HPLC 1200 Series systems (Agilent Technologies, Santa Clara, Calif., USA) using an AMINEX® HPX-87H Ion Exclusion Column (Bio-Rad, Hercules, Calif., USA) by elution with 5 mM $H_2SO_4$ at a flow rate of 0.6 ml per minute, and quantification by integration of the glucose signal from refractive index detection (CHEMSTATION®, AGILENT® 1100 HPLC, Agilent Technologies, Santa Clara, Calif., USA) calibrated by pure sugar samples. The resultant glucose and cellobiose equivalents were used to calculate the percentage of cellulose conversion for each reaction. Measured sugar concentrations were adjusted for the appropriate dilution factor. Data were processed using MICROSOFT EXCEL™ software (Microsoft, Richland, Wash., USA).

Percent conversion was calculated based on the mass ratio of solubilized glucosyl units to the initial mass of insoluble cellulose. Only glucose and cellobiose were measured for soluble sugars, as cellodextrins longer than cellobiose were present in negligible concentrations (due to enzymatic hydrolysis). The extent of total cellulose conversion was calculated using the Equation 1:

$$\% \text{ conversion} = \frac{(([\text{cellobiose}](mg/ml)/1.053) + ([\text{glucose}](mg/ml))/1.111)}{[\text{cellulose}](mg/ml)}$$ (Equation 1)

The 1.111 and 1.053 factors for glucose and cellobiose, respectively, take into account the increase in mass when the glucosyl units in cellulose (average molecular mass of 162 daltons) are converted to glucose (molecular mass of 180 daltons) or cellobiose glucosyl units (average molecular mass of 171 daltons).

Results

In a PASC experiment with 60 mg GH61 polypeptide per gram of cellulose, GH61 polypeptide from T23 was shown to convert 15.63% of the PASC to monomers in a 3 day hydrolysis assay at 50° C. at a loading of 60 mg GH61 polypeptide per gram cellulose/oligomer/monomer substrate in the presence of 2 mg beta-glucosidase per gram substrate, 10 mM pyrogallol, 100 µM copper sulfate. A control hydrolysis under the same conditions but without GH61 polypeptide did not show any detectable conversion. GH61 polypeptide from T22 was shown to convert 15.48% of the PASC to monomers under the same conditions. GH61 polypeptide from T6 was shown to convert 15.08% of the PASC to monomers under the same conditions. GH61 polypeptide from T11 was shown to convert 15.39% of the PASC to monomers under the same conditions. GH61 polypeptide from T1 was shown to convert 15.36% of the PASC to monomers under the same conditions. GH61 polypeptide from T12 was shown to convert 15.16% of the PASC to monomers under the same conditions. GH61 polypeptide from T21 was shown to convert 15.64% of the PASC to monomers under the same conditions. GH61 polypeptide from T19 was shown to convert 15.80% of the PASC to monomers under the same conditions. GH61 polypeptide from T17 was shown to convert 15.26% of the PASC to monomers under the same conditions. GH61 polypeptide from T14 was shown to convert 15.29% of the PASC to monomers under the same conditions. GH61 polypeptide from T13 was shown to convert 14.32% of the PASC to monomers under the same conditions. GH61 polypeptide from T16 was shown to convert 13.99% of the PASC to monomers under the same conditions. GH61 polypeptide from T3 was shown to convert 13.90% of the PASC to monomers under the same conditions. GH61 polypeptide from T5 was shown to convert 15.31% of the PASC to monomers under the same conditions. GH61 polypeptide from T25 was shown to convert 14.28% of the PASC to monomers under the same conditions.

In a similar PASC experiment with 60 mg GH61 polypeptide per gram of cellulose after 4 days hydrolysis, GH61 polypeptide from T23 was shown to convert 14.54% of the PASC to monomers. A control hydrolysis under the same conditions but without GH61 polypeptide did not show any detectable conversion. GH61 polypeptide from T22 was shown to convert 12.98% of the PASC to monomers under the same conditions. GH61 polypeptide from T6 was shown to convert 13.52% of the PASC to monomers under the same conditions. GH61 polypeptide from T11 was shown to convert 14.83% of the PASC to monomers under the same conditions. GH61 polypeptide from T1 was shown to convert 14.36% of the PASC to monomers under the same conditions. GH61 polypeptide from T12 was shown to convert 14.36% of the PASC to monomers under the same conditions. GH61 polypeptide from T21 was shown to convert 13.07% of the PASC to monomers under the same conditions. GH61 polypeptide from T19 was shown to convert 21.16% of the PASC to monomers under the same conditions. GH61 polypeptide from T17 was shown to convert 14.53% of the PASC to monomers under the same conditions. GH61 polypeptide from T14 was shown to convert 14.66% of the PASC to monomers under the same conditions. GH61 polypeptide from T13 was shown to convert 16.51% of the PASC to monomers under the same conditions. GH61 polypeptide from T16 was shown to convert 15.68% of the PASC to monomers under the same conditions. GH61 polypeptide from T3 was shown to convert 14.47% of the PASC to monomers under the same conditions. GH61 polypeptide from T5 was shown to convert 15.32% of the PASC to monomers under the same conditions. GH61 polypeptide from T25 was shown to convert 14.55% of the PASC to monomers under the same conditions.

In another similar PASC experiment with 20 mg GH61 polypeptide per gram of cellulose after 3 days hydrolysis, GH61 polypeptide from T9 was shown to convert 11.07% of the PASC to monomers. A control hydrolysis under the same conditions but without GH61 polypeptide did not show any detectable conversion. GH61 polypeptide from T15 was shown to convert 11.13% of the PASC to monomers under the same conditions. GH61 polypeptide from T26 was shown to convert 7.39% of the PASC to monomers under the same conditions. GH61 polypeptide from T7 was shown to convert 11.43% of the PASC to monomers under the same conditions. GH61 polypeptide from T4 was shown to convert 11.00% of the PASC to monomers under the same conditions. GH61 polypeptide from T20 was shown to convert 10.88% of the PASC to monomers under the same conditions. In second PASC experiment with 20 mg GH61 polypeptide per gram of cellulose after 3 days hydrolysis, GH61 polypeptide from T9 was shown to convert 12.57% of the PASC to monomers. A control hydrolysis under the same conditions but without GH61 polypeptide did not show any detectable conversion. GH61 polypeptide from T15 was shown to convert 12.46% of the PASC to monomers under the same conditions. GH61 polypeptide from T26 was shown to convert 8.59% of the PASC to monomers under the same conditions. GH61 polypeptide from T7 was shown to convert 12.40% of the PASC to monomers under the same conditions. GH61 polypeptide from T4 was shown to convert 12.74% of the PASC to monomers under the same conditions. GH61 polypeptide from T20 was shown to convert 12.90% of the PASC to monomers under the same conditions.

In the PCS experiment with the cellulase composition and 6 mg GH61 polypeptide per gram of cellulose after 3 days hydrolysis, GH61 polypeptide from T23 was shown to convert 16.10% of the PCS to glucose. A control hydrolysis under the same conditions but without GH61 polypeptide yielded a conversion of 9.79% of the PCS to glucose. GH61 polypeptide from T22 was shown to convert 14.00% of the PCS to glucose under the same conditions. GH61 polypeptide from T6 was shown to convert 13.84% of the PCS to glucose under the same conditions. GH61 polypeptide from T11 was shown to convert 14.08% of the PCS to glucose under the same conditions. GH61 polypeptide from T1 was shown to convert 14.92% PCS to glucose under the same conditions. GH61 polypeptide from T12 was shown to convert 18.78% of the PCS to glucose under the same conditions. GH61 polypeptide from T21 was shown to convert 13.63% of the PCS to glucose under the same conditions. GH61 polypeptide from T19 was shown to convert 15.03% of the PCS to glucose under the same conditions. GH61 polypeptide from T17 was shown to convert 13.59% of the PCS to glucose under the same conditions. GH61 polypeptide from T14 was shown to convert 13.84% of the PCS to glucose under the same conditions. GH61 polypeptide from T8 was shown to convert 14.18% of the PCS to glucose under the same conditions. GH61 polypeptide from T13 was shown to convert 14.66% of the PCS to glucose under the same conditions. GH61 polypeptide from T16 was shown to convert 14.50% of the PCS to glucose under the same conditions. GH61 polypeptide from T3 was shown to convert 16.06% of the PCS to glucose under the same conditions. GH61 polypeptide from T5 was shown to convert 14.83% of the PCS to glucose under the same conditions. GH61 polypeptide from T25 was shown to convert 13.35% of the PCS to glucose under the same conditions.

The present invention is further described by the following numbered paragraphs:

[1] An isolated polypeptide having cellulolytic enhancing activity, selected from the group consisting of:

(a) a polypeptide having at least 50%, e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 8, SEQ ID NO: 14, SEQ ID NO: 40, SEQ ID NO: 42, SEQ ID NO: 44, or SEQ ID NO: 54; at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4 or SEQ ID NO: 52; at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 36, SEQ ID NO: 38, or SEQ ID NO: 50; at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 10, SEQ ID NO: 18, or SEQ ID NO: 32; at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 30, or SEQ ID NO: 46; at least 80%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6, SEQ ID NO: 12, SEQ ID NO: 20, SEQ ID NO: 22, SEQ ID NO: 26, SEQ ID NO: 28 or SEQ ID NO: 48; at least 85%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2, SEQ ID NO: 16, or SEQ ID NO: 24; or at least 97%, e.g., at least 98%, at least 99%, or 100% sequence identity to the mature polypeptide of SEQ ID NO: 34;

(b) a polypeptide encoded by a polynucleotide that hybridizes under medium, medium-high, high, or very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, (ii) the cDNA sequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or (iii) the full-length complement of (i) or (ii);

(c) a polypeptide encoded by a polynucleotide having at least 50% e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7, SEQ ID NO: 13, SEQ ID NO: 39, SEQ ID NO: 41, SEQ ID NO: 43, or SEQ ID NO: 53, or the cDNA sequence thereof; at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or SEQ ID NO: 51, or the cDNA sequence thereof; at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 35, SEQ ID NO: 37, SEQ ID NO: 49, or the cDNA sequence thereof; at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 9, SEQ ID NO: 17, or SEQ ID NO: 31, or the cDNA sequence thereof; at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 29, or SEQ ID NO: 45, or the cDNA sequence thereof; at least 80%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5, SEQ ID NO: 11, SEQ ID NO: 19, SEQ ID NO: 21, SEQ ID NO: 25, SEQ ID NO: 27, or SEQ ID NO: 47, or the cDNA sequence thereof; at least 85%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, SEQ ID NO: 15, or SEQ ID NO: 23, or the cDNA sequence thereof; at least 97%, e.g., at least 98%, at least 99%, or 100% sequence identity to the mature polypeptide coding sequence of SEQ ID NO: 33, or the cDNA sequence thereof;

(d) a variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54 comprising a substitution, deletion, and/or insertion at one or more (e.g., several) positions; and (e) a fragment of the polypeptide of (a), (b), (c), or (d) that has cellulolytic enhancing activity.

[2] The polypeptide of paragraph 1, having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 8, SEQ ID NO: 14, SEQ ID NO: 40, SEQ ID NO: 42, SEQ ID NO: 44, or SEQ ID NO: 54; at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4 or SEQ ID NO: 52; at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 36, SEQ ID NO: 38, or SEQ ID NO: 50; at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 10, SEQ ID NO: 18, or SEQ ID NO: 32; at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 30, SEQ ID NO: 46; at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6, SEQ ID NO: 12, SEQ ID NO: 20, SEQ ID NO: 22, SEQ ID NO: 26, SEQ ID NO: 28 or SEQ ID NO: 48; at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2, SEQ ID NO: 16, or SEQ ID NO: 24; or at least 97%, at least 98%, at least 99%, or 100% sequence identity to the mature polypeptide of SEQ ID NO: 34.

[3] The polypeptide of paragraph 1 or 2, comprising or consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54.

[4] The polypeptide of paragraph 1 or 2, comprising or consisting of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54.

[5] The polypeptide of paragraph 1 or 2, wherein the mature polypeptide is amino acids 18 to 227 of SEQ ID NO: 2, amino acids 17 to 257 of SEQ ID NO: 4, amino acids 20 to 246 of SEQ ID NO: 6, amino acids 28 to 265 of SEQ ID NO: 8, amino acids 16 to 310 of SEQ ID NO: 10, amino acids 21 to 354 of SEQ ID NO: 12, amino acids 22 to 267 of SEQ ID NO: 14, amino acids 16 to 237 of SEQ ID NO: 16, amino acids 20 to 234 of SEQ ID NO: 18, amino acids 18 to 226 of SEQ ID NO: 20, amino acids 17 to 231 of SEQ ID NO: 22, amino acids 22 to 248 of SEQ ID NO: 24, amino acids 18 to 233 of SEQ ID NO: 26, amino acids 21 to 243 of SEQ ID NO: 28, amino acids 21 to 363 of SEQ ID NO: 30, amino acids 20 to 296 of SEQ ID NO: 32, amino acids 16 to 318 of SEQ ID NO: 34, amino acids 19 to 259 of SEQ ID NO: 36, amino acids 20 to 325 of SEQ ID NO: 38, amino acids 19 to 298 of SEQ ID NO: 40, amino acids 20 to 298 of SEQ ID NO: 42, amino acids 22 to 344 of SEQ ID NO: 44, amino acids 20 to 330 of SEQ ID NO: 46, amino acids 19 to 216 of SEQ ID NO: 48, amino acids 18 to 490 of SEQ ID NO: 50, amino acids 21 to 306 of SEQ ID NO: 52, or amino acids 22 to 339 of SEQ ID NO: 54.

[6] The polypeptide of paragraph 1, which is encoded by a polynucleotide that hybridizes under medium, medium-high, high, or very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, (ii) the cDNA sequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or (iii) the full-length complement of (i) or (ii).

[7] The polypeptide of paragraph 1, which is encoded by a polynucleotide at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7, SEQ ID NO: 13, SEQ ID NO: 39, SEQ ID NO: 41, SEQ ID NO: 43, or SEQ ID NO: 53, or the cDNA sequence thereof; at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or SEQ ID NO: 51, or the cDNA sequence thereof; at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 35, SEQ ID NO: 37, SEQ ID NO: 49, or the cDNA sequence thereof; at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 9, SEQ ID NO: 17, or SEQ ID NO: 31, or the cDNA sequence thereof; at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 29, or SEQ ID NO: 45, or the cDNA sequence thereof; at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5, SEQ ID NO: 11, SEQ ID NO: 19, SEQ ID NO: 21, SEQ ID NO: 25, SEQ ID NO: 27, or SEQ ID NO: 47, or the cDNA sequence thereof; at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, SEQ ID NO: 15, or SEQ ID NO: 23, or the cDNA sequence thereof; at least 97%, at least 98%, at least 99%, or 100% sequence identity to the mature polypeptide coding sequence of SEQ ID NO: 33, or the cDNA sequence thereof.

[8] The polypeptide of paragraph 1, which is encoded by a polynucleotide comprising or consisting of (i) the polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, (ii) the cDNA sequence of the polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or (iii) a subsequence thereof encoding a fragment having cellulolytic enhancing activity.

[9] The polypeptide of paragraph 1, which is encoded by a polynucleotide comprising or consisting of (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or (ii) the cDNA sequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53.

[10] The polypeptide of paragraph 1, which is encoded by a polynucleotide comprising or consisting of nucleotides 52 to 818 of SEQ ID NO: 1 or the cDNA sequence thereof, nucleotides 49 to 1117 of SEQ ID NO: 3 or the cDNA sequence thereof, nucleotides 58 to 875 of SEQ ID NO: 5 or the cDNA sequence thereof, nucleotides 82 to 1064 of SEQ ID NO: 7 or the cDNA sequence thereof, nucleotides 46 to 1032 of SEQ ID NO: 9 or the cDNA sequence thereof, nucleotides 61 to 1062 of SEQ ID NO: 11 or the cDNA sequence thereof, nucleotides 64 to 801 of SEQ ID NO: 13 or the cDNA sequence thereof, nucleotides 46 to 840 of SEQ ID NO: 15 or the cDNA sequence thereof, nucleotides 58 to 702 of SEQ ID NO: 17 or the cDNA sequence thereof, nucleotides 52 to 750 of SEQ ID NO: 19 or the cDNA sequence thereof, nucleotides 49 to 851 of SEQ ID NO: 21 or the cDNA sequence thereof, nucleotides 64 to 860 of SEQ ID NO: 23 or the cDNA sequence thereof, nucleotides 52 to 830 of SEQ ID NO: 25 or the cDNA sequence thereof, nucleotides 61 to 925 of SEQ ID NO: 27 or the cDNA sequence thereof, nucleotides 61 to 1089 of SEQ ID NO: 29 or the cDNA sequence thereof, nucleotides 58 to 1083 of SEQ ID NO: 31 or the cDNA sequence thereof, nucleotides 46 to 1029 of SEQ ID NO: 33 or the cDNA sequence thereof, nucleotides 55 to 1110 of SEQ ID NO: 35 or the cDNA sequence thereof, nucleotides 58 to 1100 of SEQ ID NO: 37 or the cDNA sequence thereof, nucleotides 55 to 1036 of SEQ ID NO: 39 or the cDNA sequence thereof, nucleotides 58 to 1022 of SEQ ID NO: 41 or the cDNA sequence thereof, nucleotides 64 to 1032 of SEQ ID NO: 43 or the cDNA sequence thereof, nucleotides 58 to 1054 of SEQ ID NO: 45 or the cDNA sequence thereof, nucleotides 55 to 769 of SEQ ID NO: 47 or the cDNA sequence thereof, nucleotides 52 to 1533 of SEQ ID NO: 49 or the cDNA sequence thereof, nucleotides 61 to 918 of SEQ ID NO: 51 or the cDNA sequence thereof, nucleotides 64 to 1089 of SEQ ID NO: 53 or the cDNA sequence thereof.

[11] The polypeptide of paragraph 1, wherein the variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54 comprises a substitution, deletion, and/or insertion at one or more (e.g., several) positions.

[12] The polypeptide of paragraph 11, wherein the variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54 comprises a substitution, deletion, and/or insertion of one or more (e.g., several) amino acids.

[13] The polypeptide of paragraph 1, which is a fragment of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54, wherein the fragment has cellulolytic enhancing activity.

[14] An isolated polynucleotide encoding the polypeptide of any of paragraphs 1-13.

[15] The polynucleotide of paragraph 14, obtained by (a) hybridizing a population of DNA under at least medium, at least medium-high, at least high, or at least very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, (ii) the cDNA sequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or (iii) a full-length complementary strand of (i) or (ii); and (b) isolating the hybridizing polynucleotide, which encodes a polypeptide having cellulolytic enhancing activity.

[16] The polynucleotide of paragraph 14, which is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7, SEQ ID NO: 13, SEQ ID NO: 39, SEQ ID NO: 41, SEQ ID NO: 43, or SEQ ID NO: 53, or the cDNA sequence thereof; at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or SEQ ID NO: 51, or the cDNA sequence thereof; at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 35, SEQ ID NO: 37, SEQ ID NO: 49, or the cDNA sequence thereof; at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 9, SEQ ID NO: 17, or SEQ ID NO: 31, or the cDNA sequence thereof; at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 29, or SEQ ID NO: 45, or the cDNA sequence thereof; at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5, SEQ ID NO: 11, SEQ ID NO: 19, SEQ ID NO: 21, SEQ ID NO: 25, SEQ ID NO: 27, or SEQ ID NO: 47, or the cDNA sequence thereof; at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, SEQ ID NO: 15, or SEQ ID NO: 23, or the cDNA sequence thereof; at least 97%, at least 98%, at least 99%, or 100% sequence identity to the mature polypeptide coding sequence of SEQ ID NO: 33, or the cDNA sequence thereof.

[17] The polynucleotide of paragraph 14, comprising or consisting of (i) the polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, (ii) the cDNA sequence of the polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or (iii) a subsequence thereof encoding a fragment having cellulolytic enhancing activity.

[18] The polynucleotide of paragraph 14, comprising or consisting of (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53, or (ii) the cDNA sequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53.

[19] The polynucleotide of paragraph 17, comprising or consisting of nucleotides 52 to 818 of SEQ ID NO: 1 or the cDNA sequence thereof, nucleotides 49 to 1117 of SEQ ID NO: 3 or the cDNA sequence thereof, nucleotides 58 to 875 of SEQ ID NO: 5 or the cDNA sequence thereof, nucleotides 82 to 1064 of SEQ ID NO: 7 or the cDNA sequence thereof, nucleotides 46 to 1032 of SEQ ID NO: 9 or the cDNA sequence thereof, nucleotides 61 to 1062 of SEQ ID NO: 11 or the cDNA sequence thereof, nucleotides 64 to 801 of SEQ ID NO: 13 or the cDNA sequence thereof, nucleotides 46 to 840 of SEQ ID NO: 15 or the cDNA sequence thereof, nucleotides 58 to 702 of SEQ ID NO: 17 or the cDNA sequence thereof, nucleotides 52 to 750 of SEQ ID NO: 19 or the cDNA sequence thereof, nucleotides 49 to 851 of SEQ ID NO: 21 or the cDNA sequence thereof, nucleotides 64 to 860 of SEQ ID NO: 23 or the cDNA sequence thereof, nucleotides 52 to 830 of SEQ ID NO: 25 or the cDNA sequence thereof, nucleotides 61 to 925 of SEQ ID NO: 27 or the cDNA sequence thereof, nucleotides 61 to 1089 of SEQ ID NO: 29 or the cDNA sequence thereof, nucleotides 58 to 1083 of SEQ ID NO: 31 or the cDNA sequence thereof, nucleotides 46 to 1029 of SEQ ID NO: 33 or the cDNA sequence thereof, nucleotides 55 to 1110 of SEQ ID NO: 35 or the cDNA sequence thereof, nucleotides 58 to 1100 of SEQ ID NO: 37 or the cDNA sequence thereof, nucleotides 55 to 1036 of SEQ ID NO: 39 or the cDNA sequence thereof, nucleotides 58 to 1022 of SEQ ID NO: 41 or the cDNA sequence thereof, nucleotides 64 to 1032 of SEQ ID NO: 43 or the cDNA sequence thereof, nucleotides 58 to 1054 of SEQ ID NO: 45 or the cDNA sequence thereof, nucleotides 55 to 769 of SEQ ID NO: 47 or the cDNA sequence thereof, nucleotides 52 to 1533 of SEQ ID NO: 49 or the cDNA sequence thereof, nucleotides 61 to 918 of SEQ ID NO: 51 or the cDNA sequence thereof, nucleotides 64 to 1089 of SEQ ID NO: 53 or the cDNA sequence thereof.

[20] A nucleic acid construct, comprising the polynucleotide of any of paragraphs 14-19 operably linked to one or more control sequences that direct the production of the polypeptide in an expression host.

[21] A recombinant expression vector comprising the nucleic acid construct of paragraph 20.

[22] A recombinant host cell comprising the polynucleotide of any of paragraphs 14-19 operably linked to one or more control sequences that direct the production of the polypeptide.

[23] A method of producing the polypeptide of any of paragraphs 1-13, comprising:
(a) cultivating a cell, which in its wild-type form produces the polypeptide, under conditions conducive for production of the polypeptide; and
(b) recovering the polypeptide.

[24] A method of producing a polypeptide having cellulolytic enhancing activity of any of paragraphs 1-13, comprising:
(a) cultivating the host cell of paragraph 22 under conditions conducive for production of the polypeptide; and
(b) recovering the polypeptide.

[25] A transgenic plant, plant part or plant cell transformed with a polynucleotide encoding the polypeptide of any of paragraphs 1-13.

[26] A method of producing a polypeptide having cellulolytic enhancing activity of any of paragraphs 1-13, comprising:
(a) cultivating the transgenic plant, plant part or plant cell of paragraph 25 under conditions conducive for production of the polypeptide; and
(b) recovering the polypeptide.

[27] A method of producing a mutant of a parent cell, comprising inactivating a polynucleotide encoding the polypeptide of any of paragraphs 1-13, which results in the mutant producing less of the polypeptide than the parent cell.

[28] A mutant cell produced by the method of paragraph 27.

[29] The mutant cell of paragraph 28, further comprising a gene encoding a native or heterologous protein.

[30] A method of producing a protein, comprising:
(a) cultivating the mutant cell of paragraph 28 or 29 under conditions conducive for production of the protein; and
(b) recovering the protein.

[31] A double-stranded inhibitory RNA (dsRNA) molecule comprising a subsequence of the polynucleotide of any of paragraphs 14-19, wherein optionally the dsRNA is an siRNA or an miRNA molecule.

[32] The double-stranded inhibitory RNA (dsRNA) molecule of paragraph 31, which is about 15, 16, 17, 18, 19, 20, 21, 22, 23, 24, 25 or more duplex nucleotides in length.

[33] A method of inhibiting the expression of a polypeptide having cellulolytic enhancing activity in a cell, comprising administering to the cell or expressing in the cell the double-stranded inhibitory RNA (dsRNA) molecule of paragraph 31 or 32.

[34] The method of paragraph 33, wherein the dsRNA is about 15, 16, 17, 18, 19, 20, 21, 22, 23, 24, 25 or more duplex nucleotides in length.

[35] An isolated polynucleotide encoding a signal peptide comprising or consisting of amino acids 1 to 17 of SEQ ID NO: 2, amino acids 1 to 16 of SEQ ID NO: 4, amino acids 1 to 19 of SEQ ID NO: 6, amino acids 1 to 27 of SEQ ID NO: 8, amino acids 1 to 15 of SEQ ID NO: 10, amino acids 1 to 20 of SEQ ID NO: 12, amino acids 1 to 21 of SEQ ID NO: 14, amino acids 1 to 15 of SEQ ID NO: 16, amino acids 1 to 19 of SEQ ID NO: 18, or amino acids 1 to 17 of SEQ ID NO: 20, amino acids 1 to 16 of SEQ ID NO: 22, amino acids 1 to 21 of SEQ ID NO: 24, amino acids 1 to 17 of SEQ ID NO: 26, amino acids 1 to 20 of SEQ ID NO: 28, or amino acids 1 to 20 of SEQ ID NO: 30, amino acids 1 to 19 of SEQ ID NO: 32, amino acids 1 to 15 of SEQ ID NO: 34, amino acids 1 to 18 of SEQ ID NO: 36, amino acids 1 to 19 of SEQ ID NO: 38, or amino acids 1 to 18 of SEQ ID NO: 40, amino acids 1 to 19 of SEQ ID NO: 42, amino acids 1 to 21 of SEQ ID NO: 44, amino acids 1 to 19 of SEQ ID NO: 46, amino acids 1 to 18 of SEQ ID NO: 48, or amino acids 1 to 17 of SEQ ID NO: 50, amino acids 1 to 20 of SEQ ID NO: 52, or amino acids 1 to 21 of SEQ ID NO: 54.

[36] A nucleic acid construct or expression vector comprising a gene encoding a protein operably linked to the polynucleotide of paragraph 35, wherein the gene is foreign to the polynucleotide encoding the signal peptide.

[37] A recombinant expression vector comprising the nucleic acid construct of paragraph 36.

[38] A recombinant host cell comprising a gene encoding a protein operably linked to the polynucleotide of paragraph 35, wherein the gene is foreign to the polynucleotide encoding the signal peptide.

[39] A method of producing a protein, comprising:
(a) cultivating a recombinant host cell comprising a gene encoding a protein operably linked to the polynucleotide of paragraph 35, wherein the gene is foreign to the polynucleotide encoding the signal peptide, under conditions conducive for production of the protein; and
(b) recovering the protein.

[40] A whole broth formulation or cell culture composition comprising the polypeptide of any of paragraphs 1-13.

[41] A composition comprising the polypeptide of any of paragraphs 1-13.

[42] The composition, which is a cellulolytic enhancing composition or a detergent composition.

[43] The composition of any of paragraphs 40-42, further comprising the enzyme composition comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[44] The composition of paragraph 43, wherein the cellulase is one or more (several) enzymes selected from the group consisting of an endoglucanase, a cellobiohydrolase, and a beta-glucosidase.

[45] The composition of paragraph 43, wherein the hemicellulase is one or more (several) enzymes selected from the group consisting of a xylanase, an acetylxylan esterase, a feruloyl esterase, an arabinofuranosidase, a xylosidase, and a glucuronidase.

[46] The composition of any of paragraphs 40-45, further comprising one or more of a cellulase, a protease, a lipase, a cutinase, an amylase, a carbohydrase, a pectinase, a mannanase, an arabinase, a galactanase, a xylanase, an oxidase.

[47] The composition of paragraph 46, which is formulated as a bar, a tablet, a powder, a granule, a paste or a liquid.

[48] A method for cleaning or washing a hard surface or laundry, the method comprising contacting the hard surface or the laundry with the composition of any of paragraphs 40-47.

[49] A method for degrading or converting a cellulosic material, comprising: treating the cellulosic material with an enzyme composition in the presence of the polypeptide having cellulolytic enhancing activity of any of paragraphs 1-13.

[50] The method of paragraph 49, wherein the cellulosic material is pretreated.

[51] The method of paragraph 50, wherein the pretreatment is selected from chemical pretreatment, physical pretreatment, and biological pretreatment.

[52] The method of any of paragraphs 49-51, wherein the cellulosic material is selected from the stems, leaves, hulls, husks, cobs of plants; or leaves, branches, and wood of trees; or agricultural residue, herbaceous material, municipal solid waste, pulp mill residue, paper mill residue, waste paper, and wood.

[53] The method of paragraph 52, wherein the cellulosic material is selected from arundo. Bagasse, bamboo, corn cob, corn fiber, corn stover, miscanthus, orange peel, rice straw, switchgrass, wheat straw, aspen, eucalyptus, fir, pine, poplar, spruce, willow, algal cellulose, bacterial cellulose, cotton linter, filter paper, microcrystalline cellulose, and phosphoric-acid treated cellulose.

[54] The method of any of paragraphs 49-53, wherein the enzyme composition comprises one or more (several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[55] The method of paragraph 54, wherein the cellulase is one or more (several) enzymes selected from the group consisting of an endoglucanase, a cellobiohydrolase, and a beta-glucosidase.

[56] The method of paragraph 54, wherein the hemicellulase is one or more (several) enzymes selected from the group consisting of a xylanase, an acetylxylan esterase, a feruloyl esterase, an arabinofuranosidase, a xylosidase, and a glucuronidase.

[57] The method of any of paragraphs 49-56, further comprising recovering the degraded cellulosic material.

[58] The method of paragraph 49, wherein the degraded cellulosic material is a sugar.

[59] The method of paragraph 58, wherein the sugar is selected from the group consisting of glucose, xylose, mannose, galactose, and arabinose.

[60] A method for producing a fermentation product, comprising:
(a) saccharifying a cellulosic material with an enzyme composition in the presence of the polypeptide having cellulolytic enhancing activity of any of paragraphs 1-13;
(b) fermenting the saccharified cellulosic material with one or more fermenting microorganisms to produce the fermentation product; and
(c) recovering the fermentation product from the fermentation.

[61] The method of paragraph 60, wherein the cellulosic material is pretreated.

[62] The method of paragraph 61, wherein the pretreatment is selected from chemical pretreatment, physical pretreatment, and biological pretreatment.

[63] The method of any of paragraphs 60-62, wherein the cellulosic material is selected from the stems, leaves, hulls, husks, cobs of plants; or leaves, branches, and wood of trees; or agricultural residue, herbaceous material, municipal solid waste, pulp mill residue, paper mill residue, waste paper, and wood.

[64] The method of paragraph 63, wherein the cellulosic material is selected from arundo. Bagasse, bamboo, corn cob, corn fiber, corn stover, miscanthus, orange peel, rice straw, switchgrass, wheat straw, aspen, eucalyptus, fir, pine, poplar, spruce, willow, algal cellulose, bacterial cellulose, cotton linter, filter paper, microcrystalline cellulose, and phosphoric-acid treated cellulose.

[65] The method of any of paragraphs 60-64, wherein the enzyme composition comprises the enzyme composition comprises one or more (several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[66] The method of paragraph 65, wherein the cellulase is one or more (several) enzymes selected from the group consisting of an endoglucanase, a cellobiohydrolase, and a beta-glucosidase.

[67] The method of paragraph 65, wherein the hemicellulase is one or more (several) enzymes selected from the group consisting of a xylanase, an acetylxylan esterase, a feruloyl esterase, an arabinofuranosidase, a xylosidase, and a glucuronidase.

[68] The method of any of paragraphs 60-67, wherein steps (a) and (b) are performed simultaneously in a simultaneous saccharification and fermentation.

[69] The method of any of paragraphs 60-68, wherein the fermentation product is an alcohol, an organic acid, a ketone, an amino acid, an alkane, a cycloalkane, an alkene, isoprene, polyketide, or a gas.

[70] A method of fermenting a cellulosic material, comprising: fermenting the cellulosic material with one or more fermenting microorganisms, wherein the cellulosic material is saccharified with an enzyme composition in the presence of the polypeptide having cellulolytic enhancing activity of any of paragraphs 1-13.

[71] The method of paragraph 70, wherein the fermenting of the cellulosic material produces a fermentation product.

[72] The method of paragraph 71, further comprising recovering the fermentation product from the fermentation.

[73] The method of any of paragraphs 70-72, wherein the cellulosic material is pretreated before saccharification.

[74] The method of any of paragraphs 70-73, wherein the enzyme composition comprises one or more enzymes selected from the group consisting of a cellulase, a GH61 polypeptide having cellulolytic enhancing activity, a hemicellulase, an expansin, an esterase, a laccase, a ligninolytic enzyme, a pectinase, a peroxidase, a protease, and a swollenin.

[75] The method of paragraph 74, wherein the cellulase is one or more (several) enzymes selected from the group consisting of an endoglucanase, a cellobiohydrolase, and a beta-glucosidase.

[76] The method of paragraph 74, wherein the hemicellulase is one or more (several) enzymes selected from the group consisting of a xylanase, an acetylxylan esterase, a feruloyl esterase, an arabinofuranosidase, a xylosidase, and a glucuronidase.

[77] The method of any of paragraphs 70-76, wherein the fermentation product is an alcohol, an alkane, a cycloalkane, an alkene, an amino acid, a gas, isoprene, a ketone, an organic acid, or polyketide.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method for degrading or converting a cellulosic material, said method comprising: treating the cellulosic material with an enzyme composition comprising a GH61 polypeptide having cellulolytic enhancing activity, wherein the GH61 polypeptide is selected from the group consisting of:
   (a) a GH61 polypeptide having at least 90% sequence identity to amino acids 21 to 354 of SEQ ID NO: 12;
   (b) a GH61 polypeptide encoded by a polynucleotide that hybridizes under at least high stringency conditions with (i) nucleotides 61 to 1062 of SEQ ID NO: 11 or the cDNA of nucleotides 61 to 1062 of SEQ ID NO: 11, or (ii) the full-length complement of (i), wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.;
   (c) a GH61 polypeptide encoded by a polynucleotide having at least 90% sequence identity to nucleotides 61 to 1062 of SEQ ID NO: 11 or the cDNA of nucleotides 61 to 1062 of SEQ ID NO: 11;
   (d) a GH61 polypeptide comprising amino acids 21 to 354 of SEQ ID NO: 12; and
   (e) a fragment of the GH61 polypeptide of (a), (b), (c), or (d) that has cellulolytic enhancing activity.

2. The method of claim 1, wherein the cellulosic material is pretreated.

3. The method of claim 1, further comprising recovering the degraded or converted cellulosic material.

4. The method of claim 3, wherein the degraded or converted cellulosic material is a sugar.

5. The method of claim 4, wherein the sugar is selected from the group consisting of glucose, xylose, mannose, galactose, and arabinose.

6. The method of claim 1, wherein the enzyme composition further comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

7. The method of claim 1, wherein the GH61 polypeptide has at least 91% sequence identity to amino acids 21 to 354 of SEQ ID NO: 12.

8. The method of claim 1, wherein the GH61 polypeptide has at least 92% sequence identity to amino acids 21 to 354 of SEQ ID NO: 12.

9. The method of claim 1, wherein the GH61 polypeptide has at least 93% sequence identity to amino acids 21 to 354 of SEQ ID NO: 12.

10. The method of claim 1, wherein the GH61 polypeptide has at least 94% sequence identity to amino acids 21 to 354 of SEQ ID NO: 12.

11. The method of claim 1, wherein the GH61 polypeptide has at least 95% sequence identity to amino acids 21 to 354 of SEQ ID NO: 12.

12. The method of claim 1, wherein the GH61 polypeptide has at least 96% sequence identity to amino acids 21 to 354 of SEQ ID NO: 12.

13. The method of claim 1, wherein the GH61 polypeptide has at least 97% sequence identity to amino acids 21 to 354 of SEQ ID NO: 12.

14. The method of claim 1, wherein the GH61 polypeptide has at least 98% sequence identity to amino acids 21 to 354 of SEQ ID NO: 12.

15. The method of claim 1, wherein the GH61 polypeptide has at least 99% sequence identity to amino acids 21 to 354 of SEQ ID NO: 12.

16. The method of claim 1, wherein the GH61 polypeptide comprises amino acids 21 to 354 of SEQ ID NO: 12.

17. A method for producing a fermentation product, said method comprising:
   (a) saccharifying a cellulosic material with an enzyme composition comprising a GH61 polypeptide having cellulolytic enhancing activity, wherein the GH61 polypeptide is selected from the group consisting of: (1) a GH61 polypeptide having at least 90% sequence identity to amino acids 21 to 354 of SEQ ID NO: 12; (2) a GH61 polypeptide encoded by a polynucleotide that hybridizes under at least high stringency conditions with (i) nucleotides 61 to 1062 of SEQ ID NO: 11 or the cDNA of nucleotides 61 to 1062 of SEQ ID NO: 11, or (ii) the full-length complement of (i), wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.; (3) a GH61 polypeptide encoded by a polynucleotide having at least 90% sequence identity to nucleotides 61 to 1062 of SEQ ID NO: 11 or the cDNA of nucleotides 61 to 1062 of SEQ ID NO: 11; (4) a GH61 polypeptide comprising amino acids 21 to 354 of SEQ ID NO: 12; and (5) a fragment of the GH61 polypeptide of (1), (2), (3), or (4) that has cellulolytic enhancing activity;
   (b) fermenting the saccharified cellulosic material with one or more fermenting microorganisms to produce the fermentation product; and
   (c) recovering the fermentation product from the fermentation.

18. The method of claim 17, wherein the cellulosic material is pretreated.

19. The method of claim 17, wherein steps (a) and (b) are performed simultaneously in a simultaneous saccharification and fermentation.

20. The method of claim 17, wherein the enzyme composition further comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

21. The method of claim 17, wherein the fermentation product is an alcohol, an organic acid, a ketone, an amino acid, an alkane, a cycloalkane, an alkene, isoprene, polyketide, or a gas.

22. The method of claim 17, wherein the GH61 polypeptide has at least 91% sequence identity to amino acids 21 to 354 of SEQ ID NO: 12.

23. The method of claim 17, wherein the GH61 polypeptide has at least 92% sequence identity to amino acids 21 to 354 of SEQ ID NO: 12.

24. The method of claim 17, wherein the GH61 polypeptide has at least 93% sequence identity to amino acids 21 to 354 of SEQ ID NO: 12.

25. The method of claim 17, wherein the GH61 polypeptide has at least 94% sequence identity to amino acids 21 to 354 of SEQ ID NO: 12.

26. The method of claim 17, wherein the GH61 polypeptide has at least 95% sequence identity to amino acids 21 to 354 of SEQ ID NO: 12.

27. The method of claim 17, wherein the GH61 polypeptide has at least 96% sequence identity to amino acids 21 to 354 of SEQ ID NO: 12.

28. The method of claim 17, wherein the GH61 polypeptide has at least 97% sequence identity to amino acids 21 to 354 of SEQ ID NO: 12.

29. The method of claim 17, wherein the GH61 polypeptide has at least 98% sequence identity to amino acids 21 to 354 of SEQ ID NO: 12.

30. The method of claim 17, wherein the GH61 polypeptide has at least 99% sequence identity to amino acids 21 to 354 of SEQ ID NO: 12.

31. The method of claim 17, wherein the GH61 polypeptide comprises amino acids 21 to 354 of SEQ ID NO: 12.

32. A method of fermenting a cellulosic material, said method comprising: fermenting the cellulosic material with one or more fermenting microorganisms, wherein the cellulosic material is saccharified with an enzyme composition comprising a GH61 polypeptide having cellulolytic enhancing activity, wherein the fermenting of the cellulosic material produces a fermentation product, and recovering the fermentation product from the fermentation, and wherein the GH61 polypeptide is selected from the group consisting of:
  (a) a GH61 polypeptide having at least 90% sequence identity to amino acids 21 to 354 of SEQ ID NO: 12;
  (b) a GH61 polypeptide encoded by a polynucleotide that hybridizes under at least high stringency conditions with
    (i) nucleotides 61 to 1062 of SEQ ID NO: 11 or the cDNA of nucleotides 61 to 1062 of SEQ ID NO: 11, or
    (ii) the full-length complement of (i), wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.;
  (c) a GH61 polypeptide encoded by a polynucleotide having at least 90% sequence identity to nucleotides 61 to 1062 of SEQ ID NO: 11 or the cDNA of nucleotides 61 to 1062 of SEQ ID NO: 11;
  (d) a GH61 polypeptide comprising amino acids 21 to 354 of SEQ ID NO: 12; and
  (e) a fragment of the GH61 polypeptide of (a), (b), (c), or (d) that has cellulolytic enhancing activity.

33. The method of claim 32, wherein the cellulosic material is pretreated.

34. The method of claim 32, wherein the enzyme composition further comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

35. The method of claim 32, wherein the fermenting of the cellulosic material produces a fermentation product.

36. The method of claim 35, further comprising recovering the fermentation product from the fermentation.

37. The method of claim 35, wherein the fermentation product is an alcohol, an organic acid, a ketone, an amino acid, an alkane, a cycloalkane, an alkene, isoprene, polyketide, or a gas.

38. The method of claim 32, wherein the GH61 polypeptide has at least 91% sequence identity to amino acids 21 to 354 of SEQ ID NO: 12.

39. The method of claim 32, wherein the GH61 polypeptide has at least 92% sequence identity to amino acids 21 to 354 of SEQ ID NO: 12.

40. The method of claim 32, wherein the GH61 polypeptide has at least 93% sequence identity to amino acids 21 to 354 of SEQ ID NO: 12.

41. The method of claim 32, wherein the GH61 polypeptide has at least 94% sequence identity to amino acids 21 to 354 of SEQ ID NO: 12.

42. The method of claim 32, wherein the GH61 polypeptide has at least 95% sequence identity to amino acids 21 to 354 of SEQ ID NO: 12.

43. The method of claim 32, wherein the GH61 polypeptide has at least 96% sequence identity to amino acids 21 to 354 of SEQ ID NO: 12.

44. The method of claim 32, wherein the GH61 polypeptide has at least 97% sequence identity to amino acids 21 to 354 of SEQ ID NO: 12.

45. The method of claim 32, wherein the GH61 polypeptide has at least 98% sequence identity to amino acids 21 to 354 of SEQ ID NO: 12.

46. The method of claim 32, wherein the GH61 polypeptide has at least 99% sequence identity to amino acids 21 to 354 of SEQ ID NO: 12.

47. The method of claim 32, wherein the GH61 polypeptide comprises amino acids 21 to 354 of SEQ ID NO: 12.

48. A nucleic acid construct comprising a polynucleotide encoding a GH61 polypeptide having cellulolytic enhancing activity, wherein the polynucleotide is operably linked to one or more heterologous control sequences that direct the production of the polypeptide, and wherein the GH61 polypeptide is selected from the group consisting of:
  (a) a GH61 polypeptide having at least 90% sequence identity to amino acids 21 to 354 of SEQ ID NO: 12;
  (b) a GH61 polypeptide encoded by a polynucleotide that hybridizes under at least high stringency conditions with
    (i) nucleotides 61 to 1062 of SEQ ID NO: 11 or the cDNA of nucleotides 61 to 1062 of SEQ ID NO: 11, or
    (ii) the full-length complement of (i), wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.;
(c) a GH61 polypeptide encoded by a polynucleotide having at least 90% sequence identity to nucleotides 61 to 1062 of SEQ ID NO: 11 or the cDNA of nucleotides 61 to 1062 of SEQ ID NO: 11;
(d) a GH61 polypeptide comprising amino acids 21 to 354 of SEQ ID NO: 12; and
(e) a fragment of the GH61 polypeptide of (a), (b), (c), or (d) that has cellulolytic enhancing activity.

49. An isolated recombinant host cell comprising the nucleic acid construct of claim 48.

50. A method of producing a GH61 polypeptide having cellulolytic enhancing activity, said method comprising:
(a) cultivating the recombinant host cell of claim 49 under conditions conducive for production of the GH61 polypeptide; and
(b) recovering the GH61 polypeptide.

51. A transgenic plant, plant part or plant cell transformed with the nucleic acid construct of claim 48.

52. A method of producing a GH61 polypeptide having cellulolytic enhancing activity, comprising:
(a) cultivating the transgenic plant, plant part or plant cell of claim 29 under conditions conducive for production of the polypeptide; and
(b) recovering the GH61 polypeptide.

53. The nucleic acid construct of claim 48, wherein the GH61 polypeptide has at least 91% sequence identity to amino acids 21 to 354 of SEQ ID NO: 12.

54. The nucleic acid construct of claim 48, wherein the GH61 polypeptide has at least 92% sequence identity to amino acids 21 to 354 of SEQ ID NO: 12.

55. The nucleic acid construct of claim 48, wherein the GH61 polypeptide has at least 93% sequence identity to amino acids 21 to 354 of SEQ ID NO: 12.

56. The nucleic acid construct of claim 48, wherein the GH61 polypeptide has at least 94% sequence identity to amino acids 21 to 354 of SEQ ID NO: 12.

57. The nucleic acid construct of claim 48, wherein the GH61 polypeptide has at least 95% sequence identity to amino acids 21 to 354 of SEQ ID NO: 12.

58. The nucleic acid construct of claim 48, wherein the GH61 polypeptide has at least 96% sequence identity to amino acids 21 to 354 of SEQ ID NO: 12.

59. The nucleic acid construct of claim 48, wherein the GH61 polypeptide has at least 97% sequence identity to amino acids 21 to 354 of SEQ ID NO: 12.

60. The nucleic acid construct of claim 48, wherein the GH61 polypeptide has at least 98% sequence identity to amino acids 21 to 354 of SEQ ID NO: 12.

61. The nucleic acid construct of claim 48, wherein the GH61 polypeptide has at least 99% sequence identity to amino acids 21 to 354 of SEQ ID NO: 12.

62. The nucleic acid construct of claim 48, wherein the GH61 polypeptide comprises amino acids 21 to 354 of SEQ ID NO: 12.

* * * * *

SEQUENCE LISTING

<160> NUMBER OF SEQ ID NOS: 108

<210> SEQ ID NO 1
<211> LENGTH: 821
<212> TYPE: DNA
<213> ORGANISM: Humicola insolens

<400> SEQUENCE: 1

```
atgaagctca gcgttgtcct cacaggcctg gcggcagccc tcgccgaggc tcattgtcag      60
tccatacgac agcgaaaccc ctggatgatc acgagactaa ccagtcctac cagacaccct     120
ccccagcgtc ggcaacaccg ccgactggca ggtcgtgcgc cagacgacca acttccagag     180
caacggcccc gtgacggacg tcaactcgga ccagatccgg tgctacgagc gcttccccgg     240 ccaggggggcg cccggcatct acaacgtcac cgccggccag accatctcgt acaacgccaa     300
ggcctctatc tcccacccgg gccccatggc cttctacatc gccaaggtcc ctgccggcta     360
caccgccgcc aactgggatg gcaggggcgc cgtgtggtcc aagatctacc aggacatgcc     420
gcgcattgcg gggagtctga cctggcctac caatggtacg aaatcctctt ctatccttca     480
tacttgctat tcctccaact gcctggcagc tcacactaac ttccacacac ccaggcgccc     540
gttccgtctc ggtaaccatc ccccgctgcc tgcaagacgg ccactacctg ttgcgcgccg     600
agcacatcgg cctgcacagc gcgagcgcg tgggcggcgc gcagttctac atctcgtgtg     660
cccagctcta cgtcagcggc ggcaccggca cttggaaccc gcgcaacaag gtcgcgttcc     720
ccggcgccta cagcccgacg cacccgggca tcatgatcaa catctactgg ccggtgccga     780
cgagctacac gccgccgggg ccgccggttg agacgtgctg a                         821
```

<210> SEQ ID NO 2
<211> LENGTH: 227
<212> TYPE: PRT
<213> ORGANISM: Humicola insolens

<400> SEQUENCE: 2

```
Met Lys Leu Ser Val Val Leu Thr Gly Leu Ala Ala Ala Leu Ala Glu
1               5                  10                  15

Ala His Tyr Thr Phe Pro Ser Val Gly Asn Thr Ala Asp Trp Gln Val
                20                  25                  30

Val Arg Gln Thr Thr Asn Phe Gln Ser Asn Gly Pro Val Thr Asp Val
            35                  40                  45

Asn Ser Asp Gln Ile Arg Cys Tyr Glu Arg Phe Pro Gly Gln Gly Ala
50                  55                  60

Pro Gly Ile Tyr Asn Val Thr Ala Gly Gln Thr Ile Ser Tyr Asn Ala
65                  70                  75                  80

Lys Ala Ser Ile Ser His Pro Gly Pro Met Ala Phe Tyr Ile Ala Lys
                85                  90                  95

Val Pro Ala Gly Tyr Thr Ala Ala Asn Trp Asp Gly Arg Gly Ala Val
            100                 105                 110

Trp Ser Lys Ile Tyr Gln Asp Met Pro Arg Ile Ala Gly Ser Leu Thr
        115                 120                 125

Trp Pro Thr Asn Gly Ala Arg Ser Val Ser Val Thr Ile Pro Arg Cys
    130                 135                 140

Leu Gln Asp Gly His Tyr Leu Leu Arg Ala Glu His Ile Gly Leu His
145                 150                 155                 160

Ser Ala Ser Gly Val Gly Gly Ala Gln Phe Tyr Ile Ser Cys Ala Gln
                165                 170                 175
```

```
Leu Tyr Val Ser Gly Gly Thr Gly Thr Trp Asn Pro Arg Asn Lys Val
            180                 185                 190

Ala Phe Pro Gly Ala Tyr Ser Pro Thr His Pro Gly Ile Met Ile Asn
        195                 200                 205

Ile Tyr Trp Pro Val Pro Thr Ser Tyr Thr Pro Gly Pro Pro Val
    210                 215                 220

Glu Thr Cys
225

<210> SEQ ID NO 3
<211> LENGTH: 1120
<212> TYPE: DNA
<213> ORGANISM: Humicola insolens

<400> SEQUENCE: 3
atgcgcccct tcctcgccgc cctcgccgcg gccaccacgg tccacgccca cggctgggtc      60
gacaacgcca ccatcgacgg cgtcttctac cagctctacc acccgtacat ggacccgtac     120
atgggcgagt tcgccccgcc tcgcatctcg cgcaagctgg tgtggaacgg ctacgtgaac     180
gacgtgacgt ccatcgacct gcaatgcggc ggacacacgg ccgaagggca aatcggcacg     240
gaacccgcgc cgctgcacgc ccccgccacg gccgggtcga cggtcaacct ccgctggacg     300
ctgtggccgg actcgcacat ggggcccatc atgacgtaca tggcgcggtg tccggacgag     360
ggttgtgata agtggttgcc gggggaggag taagtgtttc ctggcgggaa tggctgtgta     420
tttgagaagg agatattatg agtgaaactg ggagaggcga agaagagaga tgctgacgcg     480
ggttttgctc tcctcagacc agtctggttc aaaatccacg aagccggccg gtacaccacc     540
gacaagtctt accccgacga catctgggaa gttgtaagtg ccctgcctac ctatccatcc     600
ctaattccct ccctccccct ccacctcctc cttccgcgcc cccctccccc cccttatt      660 gctaaccaac cccctccctt acagacccgc ctcatgtacc cgccaacga aggctacaac      720 tacaccatcc ccgcctgcct cgcatccggc cactactgg tccggcacga gatcatcgcc      780
ttacactcgg cctgggccaa aggcgaagcg cagttctatc cctcgtgcca ccagctgacc     840
gtcacctcca tcggcggtaa cgtgcgcgaa gcgccggccg agtaccgcgt cagtttcccc     900
ggcgcgtaca aggacgatga tccgggtatt ttcatcaacg tttggaaccg taagttcttt     960 tttttgttccc cttcctccca acctacctag gtgtcgtaat gtggtccgta agggtttgtt    1020
tgttgttgag ggatatagct gacaatggat gtgtgataac acagctggcc cctacaccat    1080
tcccggaccg ccggtctgga cgtgccccga gtctgagtaa                          1120

<210> SEQ ID NO 4
<211> LENGTH: 257
<212> TYPE: PRT
<213> ORGANISM: Humicola insolens

<400> SEQUENCE: 4

Met Arg Pro Phe Leu Ala Ala Leu Ala Ala Ala Thr Thr Val His Ala
1               5                   10                  15

His Gly Trp Val Asp Asn Ala Thr Ile Asp Gly Val Phe Tyr Gln Leu
            20                  25                  30

Tyr His Pro Tyr Met Asp Pro Tyr Met Gly Glu Phe Ala Pro Pro Arg
        35                  40                  45

Ile Ser Arg Lys Leu Val Trp Asn Gly Tyr Val Asn Asp Val Thr Ser
    50                  55                  60

Ile Asp Leu Gln Cys Gly Gly His Thr Ala Glu Gly Gln Ile Gly Thr
```

```
                 65                  70                  75                  80
Glu Pro Ala Pro Leu His Ala Pro Ala Thr Ala Gly Ser Thr Val Asn
                            85                  90                  95
Leu Arg Trp Thr Leu Trp Pro Asp Ser His Met Gly Pro Ile Met Thr
                100                 105                 110
Tyr Met Ala Arg Cys Pro Asp Glu Gly Cys Asp Lys Trp Leu Pro Val
            115                 120                 125
Trp Phe Lys Ile His Glu Ala Gly Arg Tyr Thr Thr Asp Lys Ser Tyr
        130                 135                 140
Pro Asp Asp Ile Trp Glu Val Thr Arg Leu Met Tyr Pro Ala Asn Glu
145                 150                 155                 160
Gly Tyr Asn Tyr Thr Ile Pro Ala Cys Leu Ala Ser Gly His Tyr Leu
                165                 170                 175
Val Arg His Glu Ile Ile Ala Leu His Ser Ala Trp Ala Lys Gly Glu
            180                 185                 190
Ala Gln Phe Tyr Pro Ser Cys His Gln Leu Thr Val Thr Ser Ile Gly
        195                 200                 205
Gly Asn Val Arg Glu Ala Pro Ala Glu Tyr Arg Val Ser Phe Pro Gly
    210                 215                 220
Ala Tyr Lys Asp Asp Pro Gly Ile Phe Ile Asn Val Trp Asn Pro
225                 230                 235                 240
Gly Pro Tyr Thr Ile Pro Gly Pro Val Trp Thr Cys Pro Glu Ser
                245                 250                 255
Glu

<210> SEQ ID NO 5
<211> LENGTH: 878
<212> TYPE: DNA
<213> ORGANISM: Humicola insolens

<400> SEQUENCE: 5
atgagactct ccctgacaac cctcctggcc tctgccctgt ccgtccaggg tcacgccatc      60
ttccaggtgc gttcctttca ccacccacat catcatgatg aacctcaaag ttgctaaccc     120
ccgctgggca gagagttacc gtcaacggcc aggaccaagg ctcgttgact ggtctccggg     180
ccccgaataa caacaacccc gtgcagaacg tcaacagcca ggacatcatc tgtggcgctc     240
ccgggtcgcg gtcacagtcc gtcatcaacg tcaatgccgg cgaccgcatc ggtgcctggt     300
accagcatgt catcggcggc gcccagttcc ccggcgaccc ggacaacccg atcgccaggt     360
cccacaaggg cccatctcc gtctatctgg ccaaggtgga caacgctgcc acggcgaacc     420
accagggtct gcaatggtaa acatacctcg ggtcaagtca gaacctctgt gatcgccgag     480
acgactaacc cctctttccc ataaacaggt tcaagatctg gcacgacggc ttcaaccct     540
ccacccggca atgggccgtc gacaccatga tcaacaacaa cggctgggtc tatttcaacc     600
tcccgcagtg catcgctccc ggccactatc tcatgcgcgt cgagctgctc gctctccact     660
cggccaccta ccaaggccag gcgcagttct acatctcgtg cgcccagatc aacgtccagt     720
cgggcggcaa ctttactccc tggcagacgg ttagcttccc cggcgcctac caggccaacc     780
accccggcat tcaggtcaac atttacgcgc ccatgggcca gccggataac ggcggcaggc     840
cctaccagat tccgggcccg gagccgattc agtgctga                            878

<210> SEQ ID NO 6
<211> LENGTH: 246
<212> TYPE: PRT
```

<213> ORGANISM: Humicola insolens

<400> SEQUENCE: 6

Met Arg Leu Ser Leu Thr Thr Leu Leu Ala Ser Ala Leu Ser Val Gln
1               5                   10                  15

Gly His Ala Ile Phe Gln Arg Val Thr Val Asn Gly Gln Asp Gln Gly
            20                  25                  30

Ser Leu Thr Gly Leu Arg Ala Pro Asn Asn Asn Pro Val Gln Asn
        35                  40                  45

Val Asn Ser Gln Asp Ile Ile Cys Gly Ala Pro Gly Ser Arg Ser Gln
    50                  55                  60

Ser Val Ile Asn Val Asn Ala Gly Asp Arg Ile Gly Ala Trp Tyr Gln
65                  70                  75                  80

His Val Ile Gly Gly Ala Gln Phe Pro Gly Asp Pro Asp Asn Pro Ile
                85                  90                  95

Ala Arg Ser His Lys Gly Pro Ile Ser Val Tyr Leu Ala Lys Val Asp
            100                 105                 110

Asn Ala Ala Thr Ala Asn His Gln Gly Leu Gln Trp Phe Lys Ile Trp
        115                 120                 125

His Asp Gly Phe Asn Pro Ser Thr Arg Gln Trp Ala Val Asp Thr Met
130                 135                 140

Ile Asn Asn Asn Gly Trp Val Tyr Phe Asn Leu Pro Gln Cys Ile Ala
145                 150                 155                 160

Pro Gly His Tyr Leu Met Arg Val Glu Leu Leu Ala Leu His Ser Ala
                165                 170                 175

Thr Tyr Gln Gly Gln Ala Gln Phe Tyr Ile Ser Cys Ala Gln Ile Asn
            180                 185                 190

Val Gln Ser Gly Gly Asn Phe Thr Pro Trp Gln Thr Val Ser Phe Pro
        195                 200                 205

Gly Ala Tyr Gln Ala Asn His Pro Gly Ile Gln Val Asn Ile Tyr Gly
    210                 215                 220

Ala Met Gly Gln Pro Asp Asn Gly Gly Arg Pro Tyr Gln Ile Pro Gly
225                 230                 235                 240

Pro Glu Pro Ile Gln Cys
                245

<210> SEQ ID NO 7
<211> LENGTH: 1067
<212> TYPE: DNA
<213> ORGANISM: Humicola insolens

<400> SEQUENCE: 7

```
atgggaccga cctgggcagt gattctgggg ctgattgctc cttctgtgct cagtcacagt    60
tgcgtctccc aacagacctc tcgacttta tcaagctggt actgactcat aacccaactc   120
acctagatat ccatgggatc ctcctggtca atggcacaga gacaccagag tggaaatacg   180
tcctgtatgt ttcctcatat cctagcccca ttgtacgagt tgttgacgtg atacagcgat   240
gttgcgccgg cggttccaat ttcaaaccca gactctctcc ccctggata ccaaggctat   300
aaggttgatc ccatcatcgg atccgggaac cccaacatca cttgtggccg gctagcattt   360
gactcggcac ccaagacgca aatcgccgat gtgctagccg gctccgaggt aggattccga   420
gtctcggctg atggcttggg aaatcgggat ctggagaagg gctacatccc gacgttctgg   480
cacccaggtc cggcccaggc atacttgtca cgtgccccga cgacgacct gtacagctac   540
aaaggcgacg gggactggtt caagattgcc tacgctggcc cggtggacga cctgacgtgg   600
```

```
tcccctttggc cgggagtttc agatgtatgt tcatcctcca tagtcctgtt tttgccctct    660
ccaggaccaa attattaata tcgagtcgca gttcaacttc accattccgt tgtcgacacc    720
ccctggcaag tatttgctcc gaatcgagaa cttcatgcca acggcctcga caggatatct    780
tcagttctac gtcaattgtg catttgtcaa catcattgga ccaggaggtg ggaccccgac    840
cgagttcatt cgaattcccg gggattacac cgacgaggat ccaggtgagt tgtgttatg    900 agacatgttc aactcgcacc gacgaatgct gtttcctga cagagatttg taaaaactag    960
gctttctcgt tcccccggag caaagctcct tggatggcag agtcccaagg gaccagttga   1020
aactgatgag ctacacgcca ccaggtcctg cggtgtggac ggggtga                 1067
```

<210> SEQ ID NO 8
<211> LENGTH: 265
<212> TYPE: PRT
<213> ORGANISM: Humicola insolens

<400> SEQUENCE: 8

```
Met Gly Pro Thr Trp Ala Val Ile Leu Gly Leu Ile Ala Pro Ser Val
1               5                   10                  15

Leu Asn Ile His Gly Ile Leu Leu Val Asn Gly Thr Glu Thr Pro Glu
                20                  25                  30

Trp Lys Tyr Val Leu Asp Val Ala Pro Ala Val Pro Ile Ser Asn Pro
            35                  40                  45

Asp Ser Leu Pro Pro Gly Tyr Gln Gly Tyr Lys Val Asp Pro Ile Ile
        50                  55                  60

Gly Ser Gly Asn Pro Asn Ile Thr Cys Gly Arg Leu Ala Phe Asp Ser
65                  70                  75                  80

Ala Pro Lys Thr Gln Ile Ala Asp Val Leu Ala Gly Ser Glu Val Gly
                85                  90                  95

Phe Arg Val Ser Ala Asp Gly Leu Gly Asn Arg Asp Leu Glu Lys Gly
            100                 105                 110

Tyr Ile Pro Thr Phe Trp His Pro Gly Pro Ala Gln Ala Tyr Leu Ser
        115                 120                 125

Arg Ala Pro Asn Asp Asp Leu Tyr Ser Tyr Lys Gly Asp Gly Asp Trp
130                 135                 140

Phe Lys Ile Ala Tyr Ala Gly Pro Val Asp Asp Leu Thr Trp Ser Leu
145                 150                 155                 160

Trp Pro Gly Val Ser Asp Phe Asn Phe Thr Ile Pro Leu Ser Thr Pro
                165                 170                 175

Pro Gly Lys Tyr Leu Leu Arg Ile Glu Asn Phe Met Pro Thr Ala Ser
            180                 185                 190

Thr Gly Tyr Leu Gln Phe Tyr Val Asn Cys Ala Phe Val Asn Ile Ile
        195                 200                 205

Gly Pro Gly Gly Gly Thr Pro Thr Glu Phe Ile Arg Ile Pro Gly Asp
    210                 215                 220

Tyr Thr Asp Glu Asp Pro Gly Phe Leu Val Pro Glu Gln Ser Ser
225                 230                 235                 240

Leu Asp Gly Arg Val Pro Arg Asp Gln Leu Lys Leu Met Ser Tyr Thr
                245                 250                 255

Pro Pro Gly Pro Ala Val Trp Thr Gly
            260                 265
```

<210> SEQ ID NO 9
<211> LENGTH: 1035

```
<212> TYPE: DNA
<213> ORGANISM: Humicola insolens

<400> SEQUENCE: 9
atgaaggccc tcaccctcct cgccgccgcg accgcggcct cggcgcacac catcttcgtg      60
cagctcgagg ccgacggcac gcgctacccc gtctcgcacg gcgtgcgcac cccgcagtac     120
gacggcccca tcaccgacgt ctcgtccaac gacctggcct gcaacggcgg cccaacccg      180
accatgaaga cggacaagat catcaccgtg acggcgggca gcaccgtcaa ggccatctgg     240
cggcacacgc tgcagtcggg ccccaacgac gtcatggacc cagccacaa gggcccgacg      300
ctggcgtacc tgaagaaggt ggacaacgcg ctgacggatt cggcgtgg cggcggctgg       360
ttcaagatcc aggaggacgg gcacagcaat gggaattggg gcacgctcaa ggtaatcaac     420
aaccagggca ttcactatat cgatatcccc gactgcatcg acagcgggca gtatttgttg     480
cgggccgaga tgatcgctct gcacgctgcc gggtcgccgg gcggtgcgca gctttatgtg     540
agtttcttcc ttcttttctt cttctctccc tttgtgataa gaataaagat ccacaccaca    600
gtcaaaccaa agcatcctaa cctcggcatc tactcacaga tggaatgcgc ccaaatcgaa    660
atcgtcggcg gcaagggcac cgtcaagccc cagacctact ccatcccggg catctacaag    720
tccaacgacc cgggcatcct catcaacatc tactccatgt cgccctcgag ccagtacatc    780
atccccggcc cgcccctctt cacctgcaac ggcggcggcg gcagcaacaa cggcggcggc    840
aacaacggcg gcagcaaccc ccccgtccag cagccccccg ccaccaccct caccaccgcc    900
atcgcccagc ccacgcccat ctgctccgtc agcagtgggg gtcagtgcgg cggccagggc    960
tatagcggct gcaccacctg cgcgtcgccg tataggtgta acgagatcaa cgcgtggtat   1020
tcgcagtgct tgtaa                                                    1035

<210> SEQ ID NO 10
<211> LENGTH: 310
<212> TYPE: PRT
<213> ORGANISM: Humicola insolens

<400> SEQUENCE: 10

Met Lys Ala Leu Thr Leu Leu Ala Ala Ala Thr Ala Ala Ser Ala His
1               5                   10                  15

Thr Ile Phe Val Gln Leu Glu Ala Asp Gly Thr Arg Tyr Pro Val Ser
                20                  25                  30

His Gly Val Arg Thr Pro Gln Tyr Asp Gly Pro Ile Thr Asp Val Ser
            35                  40                  45

Ser Asn Asp Leu Ala Cys Asn Gly Gly Pro Asn Pro Thr Met Lys Thr
        50                  55                  60

Asp Lys Ile Ile Thr Val Thr Ala Gly Ser Thr Val Lys Ala Ile Trp
65                  70                  75                  80

Arg His Thr Leu Gln Ser Gly Pro Asn Asp Val Met Asp Pro Ser His
                85                  90                  95

Lys Gly Pro Thr Leu Ala Tyr Leu Lys Lys Val Asp Asn Ala Leu Thr
            100                 105                 110

Asp Ser Gly Val Gly Gly Gly Trp Phe Lys Ile Gln Glu Asp Gly His
        115                 120                 125

Ser Asn Gly Asn Trp Gly Thr Leu Lys Val Ile Asn Asn Gln Gly Ile
    130                 135                 140

His Tyr Ile Asp Ile Pro Asp Cys Ile Asp Ser Gly Gln Tyr Leu Leu
145                 150                 155                 160
```

```
Arg Ala Glu Met Ile Ala Leu His Ala Ala Gly Ser Pro Gly Gly Ala
                165                 170                 175
Gln Leu Tyr Met Glu Cys Ala Gln Ile Glu Ile Val Gly Gly Lys Gly
            180                 185                 190
Thr Val Lys Pro Gln Thr Tyr Ser Ile Pro Gly Ile Tyr Lys Ser Asn
        195                 200                 205
Asp Pro Gly Ile Leu Ile Asn Ile Tyr Ser Met Ser Pro Ser Ser Gln
    210                 215                 220
Tyr Ile Ile Pro Gly Pro Leu Phe Thr Cys Asn Gly Gly Gly
225                 230                 235                 240
Ser Asn Asn Gly Gly Asn Asn Gly Gly Ser Asn Pro Val Gln
                245                 250                 255
Gln Pro Pro Ala Thr Thr Leu Thr Thr Ala Ile Ala Gln Pro Thr Pro
            260                 265                 270
Ile Cys Ser Val Gln Gln Trp Gly Gln Cys Gly Gly Gln Gly Tyr Ser
        275                 280                 285
Gly Cys Thr Thr Cys Ala Ser Pro Tyr Arg Cys Asn Glu Ile Asn Ala
    290                 295                 300
Trp Tyr Ser Gln Cys Leu
305                 310

<210> SEQ ID NO 11
<211> LENGTH: 1065
<212> TYPE: DNA
<213> ORGANISM: Humicola insolens

<400> SEQUENCE: 11
atggctccca agacctcgac gttccttgcc tccctcacgg gcgccgccct cgtggctgcc      60
cacggccatg tcagccacat cattgtcaat ggcgtccagt accggaacta cgaccccacc     120
accgacttct acagcggcaa ccctccgacc gtgatcggct ggtcggccct caaccaggac     180
aacggcttca tcgagcccaa caacttcggc accccccgaca tcatctgcca taagtcggcc     240
aagcccggcg gcggccacgt cacggtgagg gccggtgaca agatcagcat cgtctggacc     300
cccgagtggc ccgagtcgca cgtcggcccc gtcatcgact accttgccgc gtgcaacggc     360
gactgcgaga cggtcgacaa gacctccctc cgcttcttca agatcgacgg cgccggctac     420
gacgccgcgg ccggccgctg ggcgccgac gctctgcgcg ccaacggcaa ctcgtggctt     480
gtgcagatcc ccgccgacct caaggccggc aactacgtgc ttcggcacga gatcatcgcc     540
ctgcacggcg ccgccaaccc caacggcgcc caggcctacc gcagtgcat caacatccgc     600 gtcaccggcg gcggcaacaa ccagccctcg ggcgtccccg gcacccagct ctacaaggcc     660
tcggacccgg gcatcctctt caaccccctgg gtcgccaacc ctcagtaccc cgtcccgggc     720
ccggccctca tccccggcgc cgtgagctcc atccctcaga gccgctcgac cgccaccgcc     780
acgggcaccg ccaccgccc cggcgccgac acggacccga cgggcgtccc tcccgtcgtc     840
accaccactt ctgcccccggc tcaggtgacc accaccacca gcagccgcac cacctccctc     900
cctcagatca ccaccacctt cgcgaccagc accaccccgc cgccccggc cgctacccag     960 agcaagtggg gccagtgcgg cggcaacggc tggaccggcc cgaccgtctg cgcgccgggc    1020
tcgagctgca acaagctcaa cgactggtac tcgcagtgca tctaa                   1065

<210> SEQ ID NO 12
<211> LENGTH: 354
<212> TYPE: PRT
<213> ORGANISM: Humicola insolens
```

<400> SEQUENCE: 12

```
Met Ala Pro Lys Thr Ser Thr Phe Leu Ala Ser Leu Thr Gly Ala Ala
1               5                   10                  15

Leu Val Ala Ala His Gly His Val Ser His Ile Ile Val Asn Gly Val
            20                  25                  30

Gln Tyr Arg Asn Tyr Asp Pro Thr Asp Phe Tyr Ser Gly Asn Pro
        35                  40                  45

Pro Thr Val Ile Gly Trp Ser Ala Leu Asn Gln Asp Asn Gly Phe Ile
    50                  55                  60

Glu Pro Asn Asn Phe Gly Thr Pro Asp Ile Ile Cys His Lys Ser Ala
65                  70                  75                  80

Lys Pro Gly Gly Gly His Val Thr Val Arg Ala Gly Asp Lys Ile Ser
                85                  90                  95

Ile Val Trp Thr Pro Glu Trp Pro Glu Ser His Val Gly Pro Val Ile
            100                 105                 110

Asp Tyr Leu Ala Ala Cys Asn Gly Asp Cys Glu Thr Val Asp Lys Thr
        115                 120                 125

Ser Leu Arg Phe Phe Lys Ile Asp Gly Ala Gly Tyr Asp Ala Ala Ala
    130                 135                 140

Gly Arg Trp Ala Ala Asp Ala Leu Arg Ala Asn Gly Asn Ser Trp Leu
145                 150                 155                 160

Val Gln Ile Pro Ala Asp Leu Lys Ala Gly Asn Tyr Val Leu Arg His
                165                 170                 175

Glu Ile Ile Ala Leu His Gly Ala Ala Asn Pro Asn Gly Ala Gln Ala
            180                 185                 190

Tyr Pro Gln Cys Ile Asn Ile Arg Val Thr Gly Gly Gly Asn Asn Gln
        195                 200                 205

Pro Ser Gly Val Pro Gly Thr Gln Leu Tyr Lys Ala Ser Asp Pro Gly
    210                 215                 220

Ile Leu Phe Asn Pro Trp Val Ala Asn Pro Gln Tyr Pro Val Pro Gly
225                 230                 235                 240

Pro Ala Leu Ile Pro Gly Ala Val Ser Ser Ile Pro Gln Ser Arg Ser
                245                 250                 255

Thr Ala Thr Ala Thr Gly Thr Ala Thr Arg Pro Gly Ala Asp Thr Asp
            260                 265                 270

Pro Thr Gly Val Pro Pro Val Val Thr Thr Ser Ala Pro Ala Gln
    275                 280                 285

Val Thr Thr Thr Ser Ser Arg Thr Ser Leu Pro Gln Ile Thr
290                 295                 300

Thr Thr Phe Ala Thr Ser Thr Pro Pro Pro Ala Ala Thr Gln
305                 310                 315                 320

Ser Lys Trp Gly Gln Cys Gly Gly Asn Gly Trp Thr Gly Pro Thr Val
                325                 330                 335

Cys Ala Pro Gly Ser Ser Cys Asn Lys Leu Asn Asp Trp Tyr Ser Gln
            340                 345                 350

Cys Ile
```

<210> SEQ ID NO 13
<211> LENGTH: 804
<212> TYPE: DNA
<213> ORGANISM: Humicola insolens

<400> SEQUENCE: 13

-continued

```
atgtatcttt tacctatcgc cgcggccgcc ctagcgttca ccaccaccgc atacgcccac    60
gcccaagtct acggcttgcg tgtcaacgac caacaccaag gcgatgggcg caacaaatac   120
atccgctcgc ccagcagcaa ttcccccatc cggtgggacc acgtaaccca cccattcctc   180
atctgcaaca tccgcgacga caaccaaccc ccgggtcccg cgcctgactt tgtccgcgcc   240
ttcgccggcg accgcgtggc gttccaatgg taccacgccc gccccaacga cccgacggat   300
tacgtcctcg acagctccca cctcggcgtc ctcgttacct ggatcgcgcc gtacacggac   360
gggcccggga ccggccccat ttggaccaag atccaccagg acgggtggaa cggcacgcac   420
tgggccacga ccggctcat cagcaacggc gggttcgtcg agttccggct gcccggctcg   480
ctaaagcccg gaagtacct ggtgcggcag agattatcg ctctgcacca ggccgacatg   540
cccggtccga accgcgggcc tgagttctac cccagctgcg cgcaattgga ggttttggg   600 tctggtgagg cggcgccgcc gcaggggtat gatatcaaca aggggtatgc ggagagcggg   660
gataagttgt ggttcaacat ttacatcaac aagaatgatg agttcaaaat gcctggaccg   720
gaggtttggg atggtgggtg tcggtttgga gagcgatggg caaccgagga ccaggcaag   780 cccaaggtga accaacacgg ataa                                          804
```

<210> SEQ ID NO 14
<211> LENGTH: 267
<212> TYPE: PRT
<213> ORGANISM: Humicola insolens

<400> SEQUENCE: 14

```
Met Tyr Leu Leu Pro Ile Ala Ala Ala Leu Ala Phe Thr Thr Thr
1               5                  10                  15

Ala Tyr Ala His Ala Gln Val Tyr Gly Leu Arg Val Asn Asp Gln His
                20                  25                  30

Gln Gly Asp Gly Arg Asn Lys Tyr Ile Arg Ser Pro Ser Ser Asn Ser
            35                  40                  45

Pro Ile Arg Trp Asp His Val Thr His Pro Phe Leu Ile Cys Asn Ile
        50                  55                  60

Arg Asp Asp Asn Gln Pro Pro Gly Pro Ala Pro Asp Phe Val Arg Ala
65                  70                  75                  80

Phe Ala Gly Asp Arg Val Ala Phe Gln Trp Tyr His Ala Arg Pro Asn
                85                  90                  95

Asp Pro Thr Asp Tyr Val Leu Asp Ser Ser His Leu Gly Val Leu Val
            100                 105                 110

Thr Trp Ile Ala Pro Tyr Thr Asp Gly Pro Gly Thr Gly Pro Ile Trp
        115                 120                 125

Thr Lys Ile His Gln Asp Gly Trp Asn Gly Thr His Trp Ala Thr Ser
    130                 135                 140

Arg Leu Ile Ser Asn Gly Gly Phe Val Glu Phe Arg Leu Pro Gly Ser
145                 150                 155                 160

Leu Lys Pro Gly Lys Tyr Leu Val Arg Gln Glu Ile Ile Ala Leu His
                165                 170                 175

Gln Ala Asp Met Pro Gly Pro Asn Arg Gly Pro Glu Phe Tyr Pro Ser
            180                 185                 190

Cys Ala Gln Leu Glu Val Phe Gly Ser Gly Glu Ala Ala Pro Pro Gln
        195                 200                 205

Gly Tyr Asp Ile Asn Lys Gly Tyr Ala Glu Ser Gly Asp Lys Leu Trp
    210                 215                 220

Phe Asn Ile Tyr Ile Asn Lys Asn Asp Glu Phe Lys Met Pro Gly Pro
```

```
                225                 230                 235                 240
Glu Val Trp Asp Gly Gly Cys Arg Phe Gly Glu Arg Trp Ala Thr Glu
                245                 250                 255
Glu Pro Gly Lys Pro Lys Val Asn Gln His Gly
            260                 265
```

<210> SEQ ID NO 15
<211> LENGTH: 843
<212> TYPE: DNA
<213> ORGANISM: Humicola insolens

<400> SEQUENCE: 15

```
atgaagctcc tcgctcctct gatgctggct ggcgccgcca gcgcccgtga gtaacccctg      60
gctggatctc atgctggtgc cagtgttcca tgactgacaa ccaccctcag acaccatctt     120
cacctccctc gaggttgatg gccgcaacta cggcacgggc aacggcgtcc gcgtcccctc     180
ctacaacggc cccgtcgagg atgtcacgtc caactcgatc gcctgcaacg gcccgccgaa     240
cccgaccagc ccgaccgaca cggtcatcac cgtccaggct ggccagaacg tgactgccat     300
ctggcggtac atgctcaaca cccagggcac ctcgcccaac gacatcatgg acagcagcca     360
caagggtcct actctcgcct acctcaagaa ggtcaacgat gccgggactg actcgggcgt     420
cggcgatggc tggttcaaga tccagcacga cggcttcgac ggcaccacct ggggcaccga     480
gcgcgtcatc ttcggccagg ccgtcacac catcaagatc cccgagtgca tcgagcccgg     540
ccagtacctg ctgcgtgctg agatgatcgc cctccacggc gcccagaact acccgggtgc     600
tcagttctac atggagtgcg cccagctcaa cattgtcggt ggcaccggca ccaagaaacc     660
cagcaccgtc agcttccctg cgcttacaa ggtatgtccg agtttggtac cgagataact     720
ggagatgaga aaagtgatgc taacaaacca tgacagggca ccgaccccgg cgtcaagctc     780
agcatctggt ggccgcccgt caccaactac gtcattcccg gccccgatgt cttcaagtgc     840
taa                                                                    843
```

<210> SEQ ID NO 16
<211> LENGTH: 237
<212> TYPE: PRT
<213> ORGANISM: Humicola insolens

<400> SEQUENCE: 16

```
Met Lys Leu Leu Ala Pro Leu Met Leu Ala Gly Ala Ala Ser Ala His
1               5                   10                  15
Thr Ile Phe Thr Ser Leu Glu Val Asp Gly Arg Asn Tyr Gly Thr Gly
                20                  25                  30
Asn Gly Val Arg Val Pro Ser Tyr Asn Gly Pro Val Glu Asp Val Thr
            35                  40                  45
Ser Asn Ser Ile Ala Cys Asn Gly Pro Pro Asn Pro Thr Ser Pro Thr
        50                  55                  60
Asp Thr Val Ile Thr Val Gln Ala Gly Gln Asn Val Thr Ala Ile Trp
65                  70                  75                  80
Arg Tyr Met Leu Asn Thr Gln Gly Thr Ser Pro Asn Asp Ile Met Asp
                85                  90                  95
Ser Ser His Lys Gly Pro Thr Leu Ala Tyr Leu Lys Lys Val Asn Asp
                100                 105                 110
Ala Arg Thr Asp Ser Gly Val Gly Asp Gly Trp Phe Lys Ile Gln His
            115                 120                 125
Asp Gly Phe Asp Gly Thr Thr Trp Gly Thr Glu Arg Val Ile Phe Gly
```

```
            130               135                140
Gln Gly Arg His Thr Ile Lys Ile Pro Glu Cys Ile Glu Pro Gly Gln
145                 150                 155                 160

Tyr Leu Leu Arg Ala Glu Met Ile Ala Leu His Gly Ala Gln Asn Tyr
                165                 170                 175

Pro Gly Ala Gln Phe Tyr Met Glu Cys Ala Gln Leu Asn Ile Val Gly
            180                 185                 190

Gly Thr Gly Thr Lys Lys Pro Ser Thr Val Ser Phe Pro Gly Ala Tyr
        195                 200                 205

Lys Gly Thr Asp Pro Gly Val Lys Leu Ser Ile Trp Trp Pro Pro Val
    210                 215                 220

Thr Asn Tyr Val Ile Pro Gly Pro Asp Val Phe Lys Cys
225                 230                 235

<210> SEQ ID NO 17
<211> LENGTH: 705
<212> TYPE: DNA
<213> ORGANISM: Humicola insolens

<400> SEQUENCE: 17
atgaagctcc tctcaaccct cgccgccatt gcggccacct tggccacggc ggatgcgcac    60
tacatcttca acatcctgta cgtcaacggc cagcgcatgg gcggcgagta cacctacgtg   120
cggcgcaact ccaactcgta cttccccgtg ttccccgaca tcctcaactc caacgacatg   180
cgttgcaacg tgggtgccag accgggcaac acccaaaccg ccaccgtcag gccggcgac   240 aggatcggct tcaaggtctt caacaacgag gtcatcgagc acctggtcc cggcttcatc   300 tacatgtcca agcccggg cagcgtcaac aactatgacg gcagcgggga ctggttcaag   360
gtttacgaga ccggtctctg ccgcggtggt ggcaacgtcg acaccaactg gtgctcgtac   420
tacaaggacc ggctcgagtt taccatcccg cccaagactc ctcccggcga gtatctggtg   480
cgtatcgagc atatcggtct gcacgagggc cacgtcaaca gggcgcagtt ctacatcacc   540
tgcgcgcagc tcaagattga ggggcccggc ggcggcaacc gaacccact cgtgaagatc   600 ccgggcatct acagggccaa cgaccccggc atcgcctaca caagtggac caacaacccg   660 gcgccgtaca tcatgccggg tcccaaggtg tgggatggca actaa                   705

<210> SEQ ID NO 18
<211> LENGTH: 234
<212> TYPE: PRT
<213> ORGANISM: Humicola insolens

<400> SEQUENCE: 18

Met Lys Leu Leu Ser Thr Leu Ala Ala Ile Ala Ala Thr Leu Ala Thr
1               5                   10                  15

Ala Asp Ala His Tyr Ile Phe Asn Ile Leu Tyr Val Asn Gly Gln Arg
            20                  25                  30

Met Gly Gly Glu Tyr Thr Tyr Val Arg Arg Asn Ser Asn Ser Tyr Phe
        35                  40                  45

Pro Val Phe Pro Asp Ile Leu Asn Ser Asn Asp Met Arg Cys Asn Val
    50                  55                  60

Gly Ala Arg Pro Gly Asn Thr Gln Thr Ala Thr Val Arg Ala Gly Asp
65                  70                  75                  80

Arg Ile Gly Phe Lys Val Phe Asn Asn Glu Val Ile Glu His Pro Gly
                85                  90                  95

Pro Gly Phe Ile Tyr Met Ser Lys Ala Pro Gly Ser Val Asn Asn Tyr
```

```
                100                 105                 110
Asp Gly Ser Gly Asp Trp Phe Lys Val Tyr Glu Thr Gly Leu Cys Arg
            115                 120                 125

Gly Gly Gly Asn Val Asp Thr Asn Trp Cys Ser Tyr Tyr Lys Asp Arg
        130                 135                 140

Leu Glu Phe Thr Ile Pro Pro Lys Thr Pro Gly Glu Tyr Leu Val
145                 150                 155                 160

Arg Ile Glu His Ile Gly Leu His Glu Gly His Val Asn Arg Ala Gln
                165                 170                 175

Phe Tyr Ile Thr Cys Ala Gln Leu Lys Ile Glu Gly Pro Gly Gly Gly
            180                 185                 190

Asn Pro Asn Pro Leu Val Lys Ile Pro Gly Ile Tyr Arg Ala Asn Asp
        195                 200                 205

Pro Gly Ile Ala Tyr Asn Lys Trp Thr Asn Asn Pro Ala Pro Tyr Ile
    210                 215                 220

Met Pro Gly Pro Lys Val Trp Asp Gly Asn
225                 230
```

<210> SEQ ID NO 19
<211> LENGTH: 753
<212> TYPE: DNA
<213> ORGANISM: Humicola insolens

<400> SEQUENCE: 19

```
atgctgggaa gcgctcttct gctcctgggc actgccctgg gcgccaccgc ccactacacg      60
ttccctagga tcaacagcgg cggcgactgg cagtatgtcc gccgggccga caactggcag     120
gacaacggct cgttggcaa cgtcaactcg cctcagatcc ggtgcttcca gagcaggcac     180
caggccgccc cggccaccct caacgtcacc gccggctcca cggtgaccta ctacgccaat     240
cccaacgtct atcaccccgg cccgatggcc ttctacatgg cccgcgtccc cgatggccag     300
gatatcaact cgtggaccgg cgagggtgcc gtgtggttca agatctacca cgagcagcct     360
accggcctgg ccagcagct gaggtggtct agcgatggta cgtgaatggt gatcctgtgg     420
catctcaacc tcttccagac ttctgacccg agccccgcg ccctacagg caagaactcg     480
ttccaggttc agatccccg ctgcatccgc tctggctact acctgctccg tgctgagcac     540
atcggcttgc acagccgg cagccctggt ggcgctcagt tctacatctc ttgcgcccag     600
ctcgccgtca acggcggtgg cagcaccgag ccccccaaca aggtgtcctt ccctggtgcc     660
tacagccgt ccgaccccgg cattcagatc aacatctact ggcctgttcc gacctcgtac     720
aagaaccccg gcccccggt cttccagtgc taa                                   753
```

<210> SEQ ID NO 20
<211> LENGTH: 226
<212> TYPE: PRT
<213> ORGANISM: Humicola insolens

<400> SEQUENCE: 20

```
Met Leu Gly Ser Ala Leu Leu Leu Gly Thr Ala Leu Gly Ala Thr
1               5                   10                  15

Ala His Tyr Thr Phe Pro Arg Ile Asn Ser Gly Gly Asp Trp Gln Tyr
                20                  25                  30

Val Arg Arg Ala Asp Asn Trp Gln Asp Asn Gly Phe Val Gly Asn Val
            35                  40                  45

Asn Ser Pro Gln Ile Arg Cys Phe Gln Ser Arg His Gln Ala Ala Pro
        50                  55                  60
```

Ala Thr Leu Asn Val Thr Ala Gly Ser Thr Val Thr Tyr Tyr Ala Asn
65                  70                  75                  80

Pro Asn Val Tyr His Pro Gly Pro Met Ala Phe Tyr Met Ala Arg Val
            85                  90                  95

Pro Asp Gly Gln Asp Ile Asn Ser Trp Thr Gly Glu Gly Ala Val Trp
            100                 105                 110

Phe Lys Ile Tyr His Glu Gln Pro Thr Gly Leu Gly Gln Gln Leu Arg
            115                 120                 125

Trp Ser Ser Asp Gly Lys Asn Ser Phe Gln Val Gln Ile Pro Arg Cys
130                 135                 140

Ile Arg Ser Gly Tyr Tyr Leu Leu Arg Ala Glu His Ile Gly Leu His
145                 150                 155                 160

Ser Ala Gly Ser Pro Gly Gly Ala Gln Phe Tyr Ile Ser Cys Ala Gln
            165                 170                 175

Leu Ala Val Asn Gly Gly Gly Ser Thr Glu Pro Pro Asn Lys Val Ser
            180                 185                 190

Phe Pro Gly Ala Tyr Ser Pro Ser Asp Pro Gly Ile Gln Ile Asn Ile
            195                 200                 205

Tyr Trp Pro Val Pro Thr Ser Tyr Lys Asn Pro Gly Pro Pro Val Phe
210                 215                 220

Gln Cys
225

<210> SEQ ID NO 21
<211> LENGTH: 854
<212> TYPE: DNA
<213> ORGANISM: Humicola insolens

<400> SEQUENCE: 21
atgaagctgc ttcctgggtt gcttctggca gccacggctg cccaagccca ttgtacgttt      60
ccgatcccca agaccatctt cgagaatttt cgagccagat cttctgaga gagttgctga     120 caattcctgc tagacacatt ccccaggctc gttgtcaacg ggcagcctga ggagagggac     180
tggtcggtca ctcggatgac aaagaaccac cagagcaagt cgggaattga aacccaact     240 agccccgaca tccgttgcta cagctcgcag actgcccta acgtggcgat tgtgccggcc     300
gggtctacca tccactacat ctcgacccaa caaatcaacc atcctggccc gactcagtac     360
tatctcgcca aggtcccagc tggtcagtca gccaagacct gggatggctc tggcaacgtg     420
tggttcaaga tcgccacgag catgccggag tacgatcaaa acaggcagct ggtttggccc     480
ggtcatagta aggactcact ctcgtccgat catctctttt gagtgagtct tgggcatacc     540
cactgactac gtctgctatg acagatacct atcagaccat caacgccacc atcccggcca     600
acacgccgag cggagagtac ctcctgcgtg tcgagcaaat tgccctccac atggccagcc     660
agccgaacaa ggcccagttc tacatctcgt gctctcagat tcagattacc aatggcggaa     720
acggcactcc gggccctcta gttgcattcc gggggcata caggagcaac gaccctggca     780
tcctggtcaa tctctacagc ggcatgcagc cttcgcagta ccagccccct ggaccggccg     840
tgtggcgtgg ctga     854

<210> SEQ ID NO 22
<211> LENGTH: 231
<212> TYPE: PRT
<213> ORGANISM: Humicola insolens

<400> SEQUENCE: 22

Met Lys Leu Leu Pro Gly Leu Leu Ala Ala Thr Ala Gln Ala
1               5                   10                  15

His Tyr Thr Phe Pro Arg Leu Val Val Asn Gly Gln Pro Glu Arg
            20                  25                  30

Asp Trp Ser Val Thr Arg Met Thr Lys Asn His Gln Ser Lys Ser Gly
        35                  40                  45

Ile Glu Asn Pro Thr Ser Pro Asp Ile Arg Cys Tyr Ser Ser Gln Thr
50                  55                  60

Ala Pro Asn Val Ala Ile Val Pro Ala Gly Ser Thr Ile His Tyr Ile
65              70                  75                  80

Ser Thr Gln Gln Ile Asn His Pro Gly Pro Thr Gln Tyr Tyr Leu Ala
                85                  90                  95

Lys Val Pro Ala Gly Gln Ser Ala Lys Thr Trp Asp Gly Ser Gly Asn
            100                 105                 110

Val Trp Phe Lys Ile Ala Thr Ser Met Pro Glu Tyr Asp Gln Asn Arg
        115                 120                 125

Gln Leu Val Trp Pro Gly His Asn Thr Tyr Gln Thr Ile Asn Ala Thr
130                 135                 140

Ile Pro Ala Asn Thr Pro Ser Gly Glu Tyr Leu Leu Arg Val Glu Gln
145             150                 155                 160

Ile Ala Leu His Met Ala Ser Gln Pro Asn Lys Ala Gln Phe Tyr Ile
                165                 170                 175

Ser Cys Ser Gln Ile Gln Ile Thr Asn Gly Gly Asn Gly Thr Pro Gly
            180                 185                 190

Pro Leu Val Ala Phe Pro Gly Ala Tyr Arg Ser Asn Asp Pro Gly Ile
        195                 200                 205

Leu Val Asn Leu Tyr Ser Gly Met Gln Pro Ser Gln Tyr Gln Pro Pro
210                 215                 220

Gly Pro Ala Val Trp Arg Gly
225                 230

<210> SEQ ID NO 23
<211> LENGTH: 863
<212> TYPE: DNA
<213> ORGANISM: Humicola insolens

<400> SEQUENCE: 23
atgctcctga actcggtcat cggctcggcc gtcctcctgg ccaccggcgc cgccgcccac      60
ggtgccgtga ccagctacgt cattgccggg aagaactacc tgggtaggt aacctcgtgg     120 aagcgaatgc aggcagttca ttcactaaca catacctccg ttagctacaa cggctacgcc    180
ccgtccacca cccccaacac gatccagtgg caatggtcga cctacgaccc catctactcc    240
gccaccgacc ccaagctccg ctgcaacggc ggccgctcgg ccacgcagtc cgccccggct    300
gctccgggcg acaacatcac cgccatctgg cagcagtgga cgcatagcca gggccccatc    360
ctcgtctgga tgtacaagtg tcccggcgcc ttcagctcgt cgacggctc gggccagggc     420 tggttcaaga ttgacgaggc cggcttcaat ggcgacggca agaccgtgtt cctcgacacc    480
gagcgcccct ccggctggga gatcgccaag ctggttggcg caacaagggg ctggaccagc    540
accatcccca agaacctggc cccgggcaac tacctggtcc gccacgagtt gattgccctt    600
caccaggcca acgcccgca gtggtaccct gagtgcgcgc aggtcgtgat caccggctcg     660
ggcactaagg agccgcctgc gtcgtacaag gctgccattc ccggctactg caaccagaac    720
gatcccaaca ttcgggtatg tgaggcctat ttggagttcg gctaaggcat gatactaact    780

```
ctacccccca ggttcctatc aacgaccact ccatccccca gacctacaag atccctggcc      840
ctccggtctg gcgcggcgag taa                                              863
```

<210> SEQ ID NO 24
<211> LENGTH: 248
<212> TYPE: PRT
<213> ORGANISM: Humicola insolens

<400> SEQUENCE: 24

```
Met Leu Leu Asn Ser Val Ile Gly Ser Ala Val Leu Ala Thr Gly
1               5                  10                  15

Ala Ala Ala His Gly Ala Val Thr Ser Tyr Val Ile Ala Gly Lys Asn
             20                  25                  30

Tyr Pro Gly Tyr Asn Gly Tyr Ala Pro Ser Thr Thr Pro Asn Thr Ile
         35                  40                  45

Gln Trp Gln Trp Ser Thr Tyr Asp Pro Ile Tyr Ser Ala Thr Asp Pro
     50                  55                  60

Lys Leu Arg Cys Asn Gly Gly Arg Ser Ala Thr Gln Ser Ala Pro Ala
65                  70                  75                  80

Ala Pro Gly Asp Asn Ile Thr Ala Ile Trp Gln Gln Trp Thr His Ser
                 85                  90                  95

Gln Gly Pro Ile Leu Val Trp Met Tyr Lys Cys Pro Gly Ala Phe Ser
            100                 105                 110

Ser Cys Asp Gly Ser Gly Gln Gly Trp Phe Lys Ile Asp Glu Ala Gly
        115                 120                 125

Phe Asn Gly Asp Gly Lys Thr Val Phe Leu Asp Thr Glu Arg Pro Ser
    130                 135                 140

Gly Trp Glu Ile Ala Lys Leu Val Gly Gly Asn Lys Gly Trp Thr Ser
145                 150                 155                 160

Thr Ile Pro Lys Asn Leu Ala Pro Gly Asn Tyr Leu Val Arg His Glu
                165                 170                 175

Leu Ile Ala Leu His Gln Ala Asn Ala Pro Gln Trp Tyr Pro Glu Cys
            180                 185                 190

Ala Gln Val Val Ile Thr Gly Ser Gly Thr Lys Glu Pro Pro Ala Ser
        195                 200                 205

Tyr Lys Ala Ala Ile Pro Gly Tyr Cys Asn Gln Asn Asp Pro Asn Ile
    210                 215                 220

Arg Val Pro Ile Asn Asp His Ser Ile Pro Gln Thr Tyr Lys Ile Pro
225                 230                 235                 240

Gly Pro Pro Val Trp Arg Gly Glu
                245
```

<210> SEQ ID NO 25
<211> LENGTH: 883
<212> TYPE: DNA
<213> ORGANISM: Humicola insolens

<400> SEQUENCE: 25

```
atgaagctca ccacctccat cgccctgctg gctgcggccg gcgcgcaggc tcactgtacg      60
tgctccctca tctcatccat ctcctcagac catgttttac ctattggtta ctaacaagct     120
ctcacgcaga cacctttccc cgcaccaagg tcgacggcgt cacctcgggc gagtgggaga     180
cgatccgcat caccgagaac cactggtcgc acgccccgt gacggacgtg acctcgcagg      240
ccatgacgtg ctacgagaag acgcccggcc agggcgcgcc caagacggtt aacgtgaagg     300
```

```
ccggcggcac cgtcaccttc accgtcgaca cggacgtggg ccacccgggc ccgctgcact    360
tctacttggc caaggtgccc gcgggcaaga cggccgcgac gtttgacggc aagggcgccg    420
tgtggttcaa gatttaccag gacggccccg gcgggttggg gaccagctcg ttgacttggc    480
ctagctttgg tgagctttct tttctttatt tcttcaatc ctcccataat tacctcccga     540
cgaggaaata aatataccctt acctgatatt aacccatccc ccccccacctc ctccaggcaa  600
gaaggaagtc tctgtccaaa tccccccctg cgtgcaggac ggcgagtacc tgctgcgcgt    660
cgagcacatt gcgctgcaca cgccgcgag cgtcggcggc gcgcagctct acatttcgtg     720
cgcgcaaatc aacgtcaccg gcggcaccgg cacgctcaac ccgggccagc tcgtctcgtt    780
cccgggcgcc tacaagccca ccgacccggg catcctgttc cagctctact ggccgccgcc    840
gacccagtac atcaaccccg gtccggcgcc ggtgaagtgc tga                       883
```

```
<210> SEQ ID NO 26
<211> LENGTH: 233
<212> TYPE: PRT
<213> ORGANISM: Humicola insolens

<400> SEQUENCE: 26

Met Lys Leu Thr Thr Ser Ile Ala Leu Leu Ala Ala Gly Ala Gln
1               5                   10                  15

Ala His Tyr Thr Phe Pro Arg Thr Lys Val Asp Gly Val Thr Ser Gly
                20                  25                  30

Glu Trp Glu Thr Ile Arg Ile Thr Glu Asn His Trp Ser His Gly Pro
            35                  40                  45

Val Thr Asp Val Thr Ser Gln Ala Met Thr Cys Tyr Glu Lys Thr Pro
        50                  55                  60

Gly Gln Gly Ala Pro Lys Thr Val Asn Val Lys Ala Gly Gly Thr Val
65                  70                  75                  80

Thr Phe Thr Val Asp Thr Asp Val Gly His Pro Gly Pro Leu His Phe
                85                  90                  95

Tyr Leu Ala Lys Val Pro Ala Gly Lys Thr Ala Ala Thr Phe Asp Gly
            100                 105                 110

Lys Gly Ala Val Trp Phe Lys Ile Tyr Gln Asp Gly Pro Gly Gly Leu
        115                 120                 125

Gly Thr Ser Ser Leu Thr Trp Pro Ser Phe Lys Lys Glu Val Ser
130                 135                 140

Val Gln Ile Pro Pro Cys Val Gln Asp Gly Glu Tyr Leu Leu Arg Val
145                 150                 155                 160

Glu His Ile Ala Leu His Ser Ala Ala Ser Val Gly Gly Ala Gln Leu
                165                 170                 175

Tyr Ile Ser Cys Ala Gln Ile Asn Val Thr Gly Gly Thr Gly Thr Leu
            180                 185                 190

Asn Pro Gly Gln Leu Val Ser Phe Pro Gly Ala Tyr Lys Pro Thr Asp
        195                 200                 205

Pro Gly Ile Leu Phe Gln Leu Tyr Trp Pro Pro Thr Gln Tyr Ile
    210                 215                 220

Asn Pro Gly Pro Ala Pro Val Lys Cys
225                 230

<210> SEQ ID NO 27
<211> LENGTH: 928
<212> TYPE: DNA
<213> ORGANISM: Humicola insolens
```

<400> SEQUENCE: 27

```
atgaagactc tcgcatccgc cctcattgcc gcgggccttc tggcccagta cgccgctgcc      60
catgccattt tccagtttgc cagcagcggt ggcactgact ttgggacgtc ctgtgttagg     120
atgccggtga gtgaacgggt gcccctgaac atgtgttgct cacgaaacaa ggttatgttg     180
actctataca gcccaacaac tctcccgtca cgagcgtcac cagcagtgac atggcttgca     240
atgttggcgg atctcgcggt gtatctggca tttgcgaggt gaacggtaag agttctcctc     300
agccttttct ctgtcaagca ctaaacagca ctcgctaacc atttcaatct cagccggctc     360
cgacttcacc gtcgagatgc acgcgcagcc aacgaccgg tcgtgcgcca gcgaagccat      420
tggcggcaac cacttcgggc ccgtcatggt gtacatggcc aaggtggacg acgcgacgcg     480
ggcggacggt gcgtcggcgt cttggttcaa ggtggacgag ttcggctacg acgccggctc     540
caagacatgg ggaaccgaca tgctcaacaa gaactgcggc aagcggacgt tccgcatccc     600
gagcaaaatc ccgtctgggg actatctggt gcgtgcggag gctattgctt tgcacaccgc     660
gggccagccg tcgggtgcgc agttttatat gagctgctat gtgagttctt ccatgcttcc     720
ccttgtggtg tcactgtata gaagatgcta atatctccca cagcaagttc gcatcaaggg     780
cagcaacaac ggtcagcttc cggctggtgt tcggattcct ggcgcctaca gcgcgacgga     840
cccgggcatc ctcgtcgata tctggggcaa tggtttcagc cagtacacta ttcctggccc     900
tcgtgtcatt gatgggagct ttttctga                                       928
```

<210> SEQ ID NO 28
<211> LENGTH: 243
<212> TYPE: PRT
<213> ORGANISM: Humicola insolens

<400> SEQUENCE: 28

```
Met Lys Thr Leu Ala Ser Ala Leu Ile Ala Ala Gly Leu Leu Ala Gln
1               5                   10                  15

Tyr Ala Ala Ala His Ala Ile Phe Gln Phe Ala Ser Ser Gly Gly Thr
            20                  25                  30

Asp Phe Gly Thr Ser Cys Val Arg Met Pro Pro Asn Asn Ser Pro Val
        35                  40                  45

Thr Ser Val Thr Ser Ser Asp Met Ala Cys Asn Val Gly Gly Ser Arg
    50                  55                  60

Gly Val Ser Gly Ile Cys Glu Val Asn Ala Gly Ser Asp Phe Thr Val
65                  70                  75                  80

Glu Met His Ala Gln Pro Asn Asp Arg Ser Cys Ala Ser Glu Ala Ile
                85                  90                  95

Gly Gly Asn His Phe Gly Pro Val Met Val Tyr Met Ala Lys Val Asp
            100                 105                 110

Asp Ala Thr Arg Ala Asp Gly Ala Ser Ala Ser Trp Phe Lys Val Asp
        115                 120                 125

Glu Phe Gly Tyr Asp Ala Gly Ser Lys Thr Trp Gly Thr Asp Met Leu
    130                 135                 140

Asn Lys Asn Cys Gly Lys Arg Thr Phe Arg Ile Pro Ser Lys Ile Pro
145                 150                 155                 160

Ser Gly Asp Tyr Leu Val Arg Ala Glu Ala Ile Ala Leu His Thr Ala
                165                 170                 175

Gly Gln Pro Ser Gly Ala Gln Phe Tyr Met Ser Cys Tyr Gln Val Arg
            180                 185                 190

Ile Lys Gly Ser Asn Asn Gly Gln Leu Pro Ala Gly Val Arg Ile Pro
```

```
            195                 200                 205
Gly Ala Tyr Ser Ala Thr Asp Pro Gly Ile Leu Val Asp Ile Trp Gly
        210                 215                 220

Asn Gly Phe Ser Gln Tyr Thr Ile Pro Gly Pro Arg Val Ile Asp Gly
225                 230                 235                 240

Ser Phe Phe

<210> SEQ ID NO 29
<211> LENGTH: 1092
<212> TYPE: DNA
<213> ORGANISM: Humicola insolens

<400> SEQUENCE: 29
atgcctcgct tcaccaagtc cattgtctcg ccctggccg gcgcttccct ggtcgcagcc     60
cacggccatg tcacccacat cgtcatcaac ggcgtgctgt acccgaactt cgaccctaca    120
tcccacccct tacctgcagaa cccgccgacc gttgtgggct ggaccgccgc caacaccgac   180
aacggcttcg ttgctcccga ccagttcgcc tcgggcgata tcatctgcca caaccaggcc   240
accaacgcgg gcggccacgc cgtggtcgcg gccggcgaca agatttggat ccagtgggac   300
cagtggcctg agagccacca cggccccgtc ctcgactacc tcgcctcctg cggcagctcg   360
ggctgcgagt cggtcaacaa gctcgacctc gagttcttca agatcggcga aaagggcctg   420
atcgacggct cctccgcgcc gggccggtgg cgtcggacg agctgatcgc caacaacgcc    480
ggctggctgg tccagatccc cgccgacatt gcgcccggcc actacgtcct cgccacgaa    540 atcatcgccc tccacgccgc cggccagccc aacggcgccc agaactaccc gcagtgcttc   600
aacctcctcg tcacgggctc cggcaccgcg cggccgcagg cgtcaaggg aacagcgctg    660 tacaccccca cgacaagggg catcttggcg ggcatctaca atgcccccgt ctcgtacgag   720
attcccggcc ccgcgctcta ctccggcgcc gccaggaact tgcagcagag ctcgtcccag   780
gccacgtcga ctgccacggc tttgactggg gacgcggtgc ctgttccgac caagccccc    840 gtcactacca cttcctcttc ttcggccgat gccgccaccg ccacctccac caccgtccag   900 ccgcccccagc aaaccacccct cacgaccgcc atcgccacgt cgaccgctgc tgctgccccg   960
acgaccaccg ccggcagcgg aaacggtggc aaccggccct tccaacccg ctgccctggc    1020 ctggctgggc tcgggtttga caagcgccgt cgccagctcc gcgctgagga gggtgtgcag   1080
gtggttgctt ga                                                       1092

<210> SEQ ID NO 30
<211> LENGTH: 363
<212> TYPE: PRT
<213> ORGANISM: Humicola insolens

<400> SEQUENCE: 30

Met Pro Arg Phe Thr Lys Ser Ile Val Ser Ala Leu Ala Gly Ala Ser
1               5                   10                  15

Leu Val Ala Ala His Gly His Val Thr His Ile Val Ile Asn Gly Val
            20                  25                  30

Leu Tyr Pro Asn Phe Asp Pro Thr Ser His Pro Tyr Leu Gln Asn Pro
        35                  40                  45

Pro Thr Val Val Gly Trp Thr Ala Ala Asn Thr Asp Asn Gly Phe Val
    50                  55                  60

Ala Pro Asp Gln Phe Ala Ser Gly Asp Ile Ile Cys His Asn Gln Ala
65                  70                  75                  80
```

Thr Asn Ala Gly Gly His Ala Val Val Ala Gly Asp Lys Ile Trp
                85                  90                  95

Ile Gln Trp Asp Gln Trp Pro Glu Ser His His Gly Pro Val Leu Asp
            100                 105                 110

Tyr Leu Ala Ser Cys Gly Ser Ser Gly Cys Glu Ser Val Asn Lys Leu
        115                 120                 125

Asp Leu Glu Phe Phe Lys Ile Gly Glu Lys Gly Leu Ile Asp Gly Ser
    130                 135                 140

Ser Ala Pro Gly Arg Trp Ala Ser Asp Glu Leu Ile Ala Asn Asn Ala
145                 150                 155                 160

Gly Trp Leu Val Gln Ile Pro Ala Asp Ile Ala Pro Gly His Tyr Val
                165                 170                 175

Leu Arg His Glu Ile Ile Ala Leu His Ala Ala Gly Gln Pro Asn Gly
            180                 185                 190

Ala Gln Asn Tyr Pro Gln Cys Phe Asn Leu Leu Val Thr Gly Ser Gly
        195                 200                 205

Thr Ala Arg Pro Gln Gly Val Lys Gly Thr Ala Leu Tyr Thr Pro Asn
    210                 215                 220

Asp Lys Gly Ile Leu Ala Gly Ile Tyr Asn Ala Pro Val Ser Tyr Glu
225                 230                 235                 240

Ile Pro Gly Pro Ala Leu Tyr Ser Gly Ala Ala Arg Asn Leu Gln Gln
                245                 250                 255

Ser Ser Ser Gln Ala Thr Ser Thr Ala Thr Ala Leu Thr Gly Asp Ala
            260                 265                 270

Val Pro Val Pro Thr Gln Ala Pro Val Thr Thr Ser Ser Ser Ser
        275                 280                 285

Ala Asp Ala Ala Thr Ala Thr Ser Thr Thr Val Gln Pro Pro Gln Gln
290                 295                 300

Thr Thr Leu Thr Thr Ala Ile Ala Thr Ser Thr Ala Ala Ala Ala Pro
305                 310                 315                 320

Thr Thr Thr Ala Gly Ser Gly Asn Gly Gly Asn Arg Pro Phe Pro Thr
                325                 330                 335

Arg Cys Pro Gly Leu Ala Gly Leu Gly Phe Asp Lys Arg Arg Arg Gln
            340                 345                 350

Leu Arg Ala Glu Glu Gly Val Gln Val Val Ala
        355                 360

<210> SEQ ID NO 31
<211> LENGTH: 1086
<212> TYPE: DNA
<213> ORGANISM: Humicola insolens

<400> SEQUENCE: 31
atgaagggac ttctcagcat cgccgccctt tccctggcgg ttggtgaggc ttcggcccac      60
tacatcttcc agcagctctc gacgggtggc accaagcacc ccatgtgtgaa gtacatccgc    120 cagcacacca actacaactc tcccgtcatc gacctcgact ccaacgacct ccgctgcaat     180
gtcggtgccc ggggtgctgg aactgagacc gttacggtcg ctgctggctc gagcctgacc    240
ttccacctcg acaccccgt ctaccaccag ggccctgtgt cggtgtaagt agaagttctc     300
agacgaacca ccaatgtcgg cagataattt ctaactccga tgtccagcta tatgtccaag    360
gctcccggct ccgtgtcgga ctatgacggc agcggcggct ggttcaagat tcaagactgg    420
ggcccgacct tcaccggcag cggcgccacc tggaagctgg atgactccta cacctccaac    480 ccccctcgt gcattcccga cggcgagtac ctcgtccgca tccagtccct gggtatccac    540

```
aaccccctggc cggcgggtat tccgcagttc tatatctcgt gcgctcaggt gcgcgtcacc    600
ggcggtggca acgcgaaccc gagcccgcag gtgtcgatcc caggtgcctt caaggagacc    660
gacccgggct acactgccaa cgtgagtttc catccatgct acatatccct tttacgctct    720
cgatcccatg actaaccccc ccctgaaaag atctacaaca acttccgcag ctacaccgtc    780
cccggcccgt ccgtcttcac ctgcagcggc aacagcggcg gcggctccaa ccccagcaac    840 cctaacccccc cgaccccgac gaccttcacc acccaggtga ccaccccgac ccggcgtct    900 ccgccctctt gcaccgtcgc gaagtggtac gtctgaaaaa aaatctcctc caggccggac    960
atgagaaaac taacatgaac gaaaaacagg ggccagtgcg gtggccaggg ctacagcggc   1020
tgcaccaact gcgaggccgg ctcgacctgc aggcagcaga acgcttacta ttctcagtgc   1080
atctaa                                                              1086
```

<210> SEQ ID NO 32
<211> LENGTH: 296
<212> TYPE: PRT
<213> ORGANISM: Humicola insolens

<400> SEQUENCE: 32

```
Met Lys Gly Leu Leu Ser Ile Ala Ala Leu Ser Leu Ala Val Gly Glu
1               5                   10                  15

Ala Ser Ala His Tyr Ile Phe Gln Gln Leu Ser Thr Gly Gly Thr Lys
            20                  25                  30

His Pro Met Trp Lys Tyr Ile Arg Gln His Thr Asn Tyr Asn Ser Pro
        35                  40                  45

Val Ile Asp Leu Asp Ser Asn Asp Leu Arg Cys Asn Val Gly Ala Arg
    50                  55                  60

Gly Ala Gly Thr Glu Thr Val Thr Val Ala Ala Gly Ser Ser Leu Thr
65                  70                  75                  80

Phe His Leu Asp Thr Pro Val Tyr His Gln Gly Pro Val Ser Val Tyr
                85                  90                  95

Met Ser Lys Ala Pro Gly Ser Val Ser Asp Tyr Asp Gly Ser Gly Gly
            100                 105                 110

Trp Phe Lys Ile Gln Asp Trp Gly Pro Thr Phe Thr Gly Ser Gly Ala
        115                 120                 125

Thr Trp Lys Leu Asp Asp Ser Tyr Thr Phe Asn Ile Pro Ser Cys Ile
    130                 135                 140

Pro Asp Gly Glu Tyr Leu Val Arg Ile Gln Ser Leu Gly Ile His Asn
145                 150                 155                 160

Pro Trp Pro Ala Gly Ile Pro Gln Phe Tyr Ile Ser Cys Ala Gln Val
                165                 170                 175

Arg Val Thr Gly Gly Asn Ala Asn Pro Ser Pro Gln Val Ser Ile
            180                 185                 190

Pro Gly Ala Phe Lys Glu Thr Asp Pro Gly Tyr Thr Ala Asn Ile Tyr
        195                 200                 205

Asn Asn Phe Arg Ser Tyr Thr Val Pro Gly Pro Ser Val Phe Thr Cys
    210                 215                 220

Ser Gly Asn Ser Gly Gly Gly Ser Asn Pro Ser Asn Pro Asn Pro
225                 230                 235                 240

Thr Pro Thr Thr Phe Thr Thr Gln Val Thr Thr Pro Thr Pro Ala Ser
                245                 250                 255

Pro Pro Ser Cys Thr Val Ala Lys Trp Gly Gln Cys Gly Gly Gln Gly
            260                 265                 270
```

Tyr Ser Gly Cys Thr Asn Cys Glu Ala Gly Ser Thr Cys Arg Gln Gln
        275                 280                 285

Asn Ala Tyr Tyr Ser Gln Cys Ile
    290                 295

<210> SEQ ID NO 33
<211> LENGTH: 1032
<212> TYPE: DNA
<213> ORGANISM: Humicola insolens

<400> SEQUENCE: 33

```
atgaggccct tctcactcgt cgctctggcg acggccgtca gcggccacgc catcttccag      60
cgcgtgtcgg ttaacggcgt cgaccaaggc cagctcaagg gcgtccgcgc tcctcgagc     120
aactacccca tcgagaacgt caaccacccc gactttgcct gcaacaccaa catccagcac    180
cgcgacggca ccgtcatcaa gatccccgcc ggcgccaccg tcggcgcctg gtggcagcac    240
gagatcggcg ggccctcgtt cccgggtgac ccggataacc cgatcgctgc ttcgcacaag    300
ggtgagttcc catagataga tctcttctct cccgaccct tgtatcctct cataactaac     360
cacctcaacc ccccaggccc tatccaagtc tacctcgcca aggtcgacaa cgccgcgacc    420
gcctccccca acggcctgcg gtggttcaag attgccgaga agggcctgtc gggcggcgtc    480
tgggccgtcg acgagatgat ccgcaacaac ggctggcact acttcaccat gccgcagtgc    540
atcgcgcccg ccactacct gatgcgcgtc gagctgttgg cgctgcactc ggccagcttc    600
cccgcggcg cccagttcta catggagtgc gcccagatcg aggtcaccgg ctcgggcaac    660
ttctcgccct ccgagacggt cagcttcccc ggcgcctacc cggccaacca cccgggtatc    720
gtcgtcagca tctacgacgc ccagggtaac gccaacaacg gcgggcgcga gtaccagatc    780
cccgggccgc ggccgatcac ctgctccggc ggtggaagca caatggtgg cgggaacaac    840
aatggtggtg gaaacaacaa cggcggcggc aacaacaacg gcggtgggaa caacaacggt    900
ggtggtaaca ccggtggcgg ctcggcgccg ctctggggcc agtgcggcgg caatgggtat    960
accggcccga cgacttgtgc cgagggtact tgcaagaagc agaatgactg gtactcgcag   1020
tgtacgcctt ag                                                      1032
```

<210> SEQ ID NO 34
<211> LENGTH: 318
<212> TYPE: PRT
<213> ORGANISM: Humicola insolens

<400> SEQUENCE: 34

Met Arg Pro Phe Ser Leu Val Ala Leu Ala Thr Ala Val Ser Gly His
1               5                   10                  15

Ala Ile Phe Gln Arg Val Ser Val Asn Gly Val Asp Gln Gly Gln Leu
            20                  25                  30

Lys Gly Val Arg Ala Pro Ser Ser Asn Tyr Pro Ile Glu Asn Val Asn
        35                  40                  45

His Pro Asp Phe Ala Cys Asn Thr Asn Ile Gln His Arg Asp Gly Thr
    50                  55                  60

Val Ile Lys Ile Pro Ala Gly Ala Thr Val Gly Ala Trp Trp Gln His
65                  70                  75                  80

Glu Ile Gly Gly Pro Ser Phe Pro Gly Asp Pro Asp Asn Pro Ile Ala
                85                  90                  95

Ala Ser His Lys Gly Pro Ile Gln Val Tyr Leu Ala Lys Val Asp Asn
            100                 105                 110

```
Ala Ala Thr Ala Ser Pro Asn Gly Leu Arg Trp Phe Lys Ile Ala Glu
        115                 120                 125

Lys Gly Leu Ser Gly Gly Val Trp Ala Val Asp Glu Met Ile Arg Asn
    130                 135                 140

Asn Gly Trp His Tyr Phe Thr Met Pro Gln Cys Ile Ala Pro Gly His
145                 150                 155                 160

Tyr Leu Met Arg Val Glu Leu Leu Ala Leu His Ser Ala Ser Phe Pro
                165                 170                 175

Gly Gly Ala Gln Phe Tyr Met Glu Cys Ala Gln Ile Glu Val Thr Gly
            180                 185                 190

Ser Gly Asn Phe Ser Pro Ser Glu Thr Val Ser Phe Pro Gly Ala Tyr
        195                 200                 205

Pro Ala Asn His Pro Gly Ile Val Val Ser Ile Tyr Asp Ala Gln Gly
    210                 215                 220

Asn Ala Asn Asn Gly Gly Arg Glu Tyr Gln Ile Pro Gly Pro Arg Pro
225                 230                 235                 240

Ile Thr Cys Ser Gly Gly Ser Asn Asn Gly Gly Asn Asn Asn
                245                 250                 255

Gly Gly Gly Asn Asn Gly Gly Asn Asn Gly Gly Asn
            260                 265                 270

Asn Asn Gly Gly Gly Asn Thr Gly Gly Ser Ala Pro Leu Trp Gly
            275                 280                 285

Gln Cys Gly Gly Asn Gly Tyr Thr Gly Pro Thr Thr Cys Ala Glu Gly
    290                 295                 300

Thr Cys Lys Lys Gln Asn Asp Trp Tyr Ser Gln Cys Thr Pro
305                 310                 315

<210> SEQ ID NO 35
<211> LENGTH: 1113
<212> TYPE: DNA
<213> ORGANISM: Humicola insolens

<400> SEQUENCE: 35
atggtgttgc ggtctctctc tatcctggcc ttcgtagcca gaggcgtctt cgcccacggt      60
ggcctctcca actacacggt cggcgacacg tggtatagcg ggtgcgtcca tgaacaactc     120
ctatatcttc cccccctcca cattgcgacc gctgcacatc tcactcgtcc ataaacaaca     180
acatcaatcg gtagacactg tccaaaagct aaccaccgta cctcctgaac acagctacga     240
ccccttcacc cccgccgccg cccaactctc ccaaccctgg ctgatccaac gccaatggac     300
cagcatcgac ccgctcttct ccccgacctc tccctacctc gcctgcaact tccccggcac     360
cgcgccacca tcttacatcc ctctccgcgc cggcgacatc ctcaccgcgg tttactggtt     420
ctggctgcac cccgtggggc cgatgagcgt ttggctggcg cggtgcgcag gggactgccg     480
cgacgaggac gtgacgcggg cgcgctggtt caagatctgg catgcggggt ttctggaggg     540
gccgaatttg gagctcggga tgtggtatca agaagaagttc cagcggtggg atggcgggcc     600
ggcgctctgg cgggtgagga taccgagggg gttgaagaag gggttgtaca tggtcaggca     660
tgagattttg tcgattcatg tgggtggacg gccccagttt tatcccgagt gtgcgcactt     720
gaatgtgacg gagggtggtg aggtggtagt gccgggggag tggacgagaa ggttccctgg     780
ggcgtatgac gatgatggtg agtgccttgc tagacgggaa ggctctatgg atggggcgga     840
tgagacgaaa ggctggtgtg agactgtcag cactgacggc ctgcagacaa gtcagtcttc     900
atcgatatct accggccgga acatgaaaac aggacggtac gtgggacaag caagcctcgg     960
```

```
attttttcaga ttttcgactc tgacaacgaa caggactatg agatccctgg aggcccgatt      1020
tgggaaaggt acgtacaatc gcatcatctt gactctgtat tcagggcta acataaacac       1080 agcttggggg agatggagtt atggcctgaa tga                                    1113
```

<210> SEQ ID NO 36
<211> LENGTH: 259
<212> TYPE: PRT
<213> ORGANISM: Humicola insolens

<400> SEQUENCE: 36

```
Met Val Leu Arg Ser Leu Ser Ile Leu Ala Phe Val Ala Arg Gly Val
1               5                   10                  15

Phe Ala His Gly Gly Leu Ser Asn Tyr Thr Val Gly Asp Thr Trp Tyr
            20                  25                  30

Ser Gly Tyr Asp Pro Phe Thr Pro Ala Ala Ala Gln Leu Ser Gln Pro
        35                  40                  45

Trp Leu Ile Gln Arg Gln Trp Thr Ser Ile Asp Pro Leu Phe Ser Pro
    50                  55                  60

Thr Ser Pro Tyr Leu Ala Cys Asn Phe Pro Gly Thr Ala Pro Pro Ser
65                  70                  75                  80

Tyr Ile Pro Leu Arg Ala Gly Asp Ile Leu Thr Ala Val Tyr Trp Phe
                85                  90                  95

Trp Leu His Pro Val Gly Pro Met Ser Val Trp Leu Ala Arg Cys Ala
            100                 105                 110

Gly Asp Cys Arg Asp Glu Asp Val Thr Arg Ala Arg Trp Phe Lys Ile
        115                 120                 125

Trp His Ala Gly Phe Leu Glu Gly Pro Asn Leu Glu Leu Gly Met Trp
    130                 135                 140

Tyr Gln Lys Lys Phe Gln Arg Trp Asp Gly Gly Pro Ala Leu Trp Arg
145                 150                 155                 160

Val Arg Ile Pro Arg Gly Leu Lys Lys Gly Leu Tyr Met Val Arg His
                165                 170                 175

Glu Ile Leu Ser Ile His Val Gly Gly Arg Pro Gln Phe Tyr Pro Glu
            180                 185                 190

Cys Ala His Leu Asn Val Thr Glu Gly Gly Glu Val Val Val Pro Gly
        195                 200                 205

Glu Trp Thr Arg Arg Phe Pro Gly Ala Tyr Asp Asp Asp Lys Ser
    210                 215                 220

Val Phe Ile Asp Ile Tyr Arg Pro Glu His Glu Asn Arg Thr Asp Tyr
225                 230                 235                 240

Glu Ile Pro Gly Gly Pro Ile Trp Glu Ser Leu Gly Glu Met Glu Leu
                245                 250                 255

Trp Pro Glu
```

<210> SEQ ID NO 37
<211> LENGTH: 1103
<212> TYPE: DNA
<213> ORGANISM: Humicola insolens

<400> SEQUENCE: 37

```
atgaggaccg tcttcgccgc cgcactggca gcactcgctg cccgggaagt cgccggccat      60
gccacgttcc agcaactctg ggttgacgga accgattata taagtgcccc cctttttctcg    120 gttccatttg atatcatgat gctgacaccc ccagcacggc agcacctgcg tccgcctccc    180
```

```
cgccagcaac agcccsctga ccgacgtcac cagcagcgac ttcgcctgca acatcggcgg      240
ccggcgcggc gtgggcggca aatgccccgt caaagccggc ggcgtggtca cgatcgagat      300
gcatcagcag cccaacgacc ggaactgccg cagcgaggcc atcggcggca tgcactgggg      360
tccggtgcag gtctacctca gcaaggtccc cgacgcgtcg accgccgagc cgacgcaggt      420
gggctggttc aagatcttct ccaacgcgtg ggccaagaag cccggcggca actcgggcga      480
cgacgactac tggggcacgc gcgagctcaa cggctgctgc gggcgcatgg acgtgccgat      540
ccccaccgac ctggaagacg gcgactacct gctgcgcgcc gaggcgctgg cgctgcacgc      600
catgccgggc cagttctaca tgtcgtgcta ccagatcacc atcacgggcg gcacgggcac      660
cgcgaagccg gcgactgtcc gcttccccgg agcgtacacc aacaacgacg ccggcatccg      720
cgccaacatc cacgccccgc tgagcaccta catcgcgccc ggcccggagg tgtactccgg      780
cggtaccacc cgggcgcccg tgagggctg cccgggatgt gctacgacct gccaggttgg      840
ctcgtcgccc agcgcgcagg ctccaggcca tggcacggcc gtgggcggcg gagctggtgg      900
cccgtctgct tgcaccgtcc aggcgtatgg ccagtgcggt ggccagggat acacgggttg      960
caccgagtgc gcggtaagtt gggacttcct tgtcattaaa atcgcaaatg gaacggatgg     1020
gctaacattt gcgggtgcag gatggtttcg tttgccgcga cgtctcggct ccgtggtact     1080
ctcagtgcca gcctgctttc taa                                             1103
```

<210> SEQ ID NO 38
<211> LENGTH: 325
<212> TYPE: PRT
<213> ORGANISM: Humicola insolens

<400> SEQUENCE: 38

```
Met Arg Thr Val Phe Ala Ala Ala Leu Ala Ala Leu Ala Ala Arg Glu
1               5                   10                  15

Val Ala Gly His Ala Thr Phe Gln Gln Leu Trp Val Asp Gly Thr Asp
            20                  25                  30

Tyr Gly Ser Thr Cys Val Arg Leu Pro Ala Ser Asn Ser Pro Leu Thr
        35                  40                  45

Asp Val Thr Ser Ser Asp Phe Ala Cys Asn Ile Gly Gly Arg Arg Gly
    50                  55                  60

Val Gly Gly Lys Cys Pro Val Lys Ala Gly Gly Val Val Thr Ile Glu
65                  70                  75                  80

Met His Gln Gln Pro Asn Asp Arg Asn Cys Arg Ser Glu Ala Ile Gly
                85                  90                  95

Gly Met His Trp Gly Pro Val Gln Val Tyr Leu Ser Lys Val Pro Asp
            100                 105                 110

Ala Ser Thr Ala Glu Pro Thr Gln Val Gly Trp Phe Lys Ile Phe Ser
        115                 120                 125

Asn Ala Trp Ala Lys Lys Pro Gly Gly Asn Ser Gly Asp Asp Asp Tyr
    130                 135                 140

Trp Gly Thr Arg Glu Leu Asn Gly Cys Cys Gly Arg Met Asp Val Pro
145                 150                 155                 160

Ile Pro Thr Asp Leu Glu Asp Gly Asp Tyr Leu Leu Arg Ala Glu Ala
                165                 170                 175

Leu Ala Leu His Ala Met Pro Gly Gln Phe Tyr Met Ser Cys Tyr Gln
            180                 185                 190

Ile Thr Ile Thr Gly Gly Thr Gly Thr Ala Lys Pro Ala Thr Val Arg
        195                 200                 205
```

```
Phe Pro Gly Ala Tyr Thr Asn Asn Asp Ala Gly Ile Arg Ala Asn Ile
    210                 215                 220
His Ala Pro Leu Ser Thr Tyr Ile Ala Pro Gly Pro Glu Val Tyr Ser
225                 230                 235                 240
Gly Gly Thr Thr Arg Ala Pro Gly Glu Gly Cys Pro Gly Cys Ala Thr
                245                 250                 255
Thr Cys Gln Val Gly Ser Ser Pro Ser Ala Gln Ala Pro Gly His Gly
            260                 265                 270
Thr Ala Val Gly Gly Gly Ala Gly Gly Pro Ser Ala Cys Thr Val Gln
        275                 280                 285
Ala Tyr Gly Gln Cys Gly Gly Gln Gly Tyr Thr Gly Cys Thr Glu Cys
    290                 295                 300
Ala Asp Gly Phe Val Cys Arg Asp Val Ser Ala Pro Trp Tyr Ser Gln
305                 310                 315                 320
Cys Gln Pro Ala Phe
                325
```

```
<210> SEQ ID NO 39
<211> LENGTH: 1039
<212> TYPE: DNA
<213> ORGANISM: Humicola insolens

<400> SEQUENCE: 39
atgaggctcc cccaagtggc ttccgttctg gccctcgcgg cccaggtcca cggtcacggc      60
tacatctacc gtgtcaccgc cgacaacatt gtgtaagcgc cctcagattc cggacctctt     120
cctacctggt ggctaacctt ctctcaactc ttcagctacc cgggatacga catctatgtc     180
gatcccctcc tccaaccgcc cccgtaccgc attgcctacg tggtggccga cgggtccc      240
gtctatgata tcaacagcaa ggatatcgcc tgccagcgcg tccacagccc cgctccgggt     300
ctgattgccc aggctcgcgc gggcagcaac atcaccttct ggtggtcgcg gtggctgtac     360
agccacaagg gtcccatctc ggcatggatg gctccgtatg agggcgacat tgccaatgtg     420
gacgtcaacc agctcgagtt cttcaagatt ggcgaggagt tccacgatga accggcaag     480
tgggcgacgg agaagctggt ggacgacccc gagggcaagt ggaccgtcaa gatccccgcc     540
gatatcaagc ccggtctcta tgtcgtgcgg aacgaggtaa gtttcatccg tcccaaaaaa     600
ggggtcccat cccatgcatg gtgcatgccc agtctaatca tcatctcccg gatagatcat     660
cgccctccac ttcgccgtcc gcatgcctcc cttctttgcc gccttcaccc cctcggacc      720
gcagttctac atgaccctgct tcgccttcaa catcaccggc gacggcacgg ccactcccca     780
gggctacaag ttccctggcg cctacagcaa ggacgatccg gccctgtggt gggatctgga     840
ggagaacaag aacccgtacc ccggcgccgg ccccaagccc cacgtctcgg cctacgatgt     900
cgacctcgtc cccaacgagt tgtacatcgt cagcccgacg aacaacgcga cggctgatga     960
gctctactgg gaggcccaga ggcaggcgct tgctgcccag gcggcgacga cggagtactt    1020
tgactcgatt ggtggctaa                                                 1039
```

```
<210> SEQ ID NO 40
<211> LENGTH: 298
<212> TYPE: PRT
<213> ORGANISM: Humicola insolens

<400> SEQUENCE: 40

Met Arg Leu Pro Gln Val Ala Ser Val Leu Ala Leu Ala Ala Gln Val
1               5                   10                  15
```

His Gly His Gly Tyr Ile Tyr Arg Val Thr Ala Asp Asn Ile Val Tyr
            20                  25                  30

Pro Gly Tyr Asp Ile Tyr Val Asp Pro Leu Leu Gln Pro Pro Tyr
        35                  40                  45

Arg Ile Ala Tyr Gly Gly Gln Thr Gly Pro Val Tyr Asp Ile Asn
    50                  55                  60

Ser Lys Asp Ile Ala Cys Gln Arg Val His Ser Pro Ala Pro Gly Leu
65                  70                  75                  80

Ile Ala Gln Ala Arg Ala Gly Ser Asn Ile Thr Phe Trp Trp Ser Arg
                85                  90                  95

Trp Leu Tyr Ser His Lys Gly Pro Ile Ser Ala Trp Met Ala Pro Tyr
            100                 105                 110

Glu Gly Asp Ile Ala Asn Val Asp Val Asn Gln Leu Glu Phe Phe Lys
            115                 120                 125

Ile Gly Glu Glu Phe His Asp Glu Thr Gly Lys Trp Ala Thr Glu Lys
    130                 135                 140

Leu Val Asp Asp Pro Glu Gly Lys Trp Thr Val Lys Ile Pro Ala Asp
145                 150                 155                 160

Ile Lys Pro Gly Leu Tyr Val Val Arg Asn Glu Ile Ile Ala Leu His
                165                 170                 175

Phe Ala Val Arg Met Pro Pro Phe Phe Ala Ala Phe Thr Pro Leu Gly
            180                 185                 190

Pro Gln Phe Tyr Met Thr Cys Phe Ala Phe Asn Ile Thr Gly Asp Gly
        195                 200                 205

Thr Ala Thr Pro Gln Gly Tyr Lys Phe Pro Gly Ala Tyr Ser Lys Asp
    210                 215                 220

Asp Pro Ala Leu Trp Trp Asp Leu Glu Glu Asn Lys Asn Pro Tyr Pro
225                 230                 235                 240

Gly Ala Gly Pro Lys Pro His Val Ser Ala Tyr Asp Val Asp Leu Val
                245                 250                 255

Pro Asn Glu Leu Tyr Ile Val Ser Pro Thr Asn Asn Ala Thr Ala Asp
            260                 265                 270

Glu Leu Tyr Trp Glu Ala Gln Arg Gln Ala Leu Ala Ala Gln Ala Ala
        275                 280                 285

Thr Thr Glu Tyr Phe Asp Ser Ile Gly Gly
    290                 295

<210> SEQ ID NO 41
<211> LENGTH: 1025
<212> TYPE: DNA
<213> ORGANISM: Humicola insolens

<400> SEQUENCE: 41
atgcacgtcc agtctctcct tgccggagcg ctcgctctgg ctccgtcggc gtctgctcac      60
ttcctcttcc cgcacctgat gctgaacggt gtccgcacgg gagcctacga gtatgtccgg     120
gagcacgact tcggcttcat gccgcacaac aacgactgga tcaactcgcc cgatttccgt     180
tgcaacgagg ggtcctggcg tcatcgccgc gagcccaaga ccgccgtagt cactgccggc     240
gttgacgtcg tgggcttcaa cctgcacctg gactttgacc tgtaccatcc gggcccgtg      300 acggtaagca catctgagtc agaacatacc tccctgtgac gtagactaat gagtctctta     360
ccgcagatct atctctcccg cgcccccggc gacgtgcgtg actacgacgg atctggtgac     420
tggttcaagt gtgtaccagct gggcacccgc caacccttca cggcactga cgagggctgg     480 gccacttgga agatgaagaa ctggcagttc cgcctgcccg ctgagatccc ggcgggcgag     540

-continued

```
tacctgatgc gcatcgagca gatgagcgtg caccctcctt accgccagaa ggagtggtac    600
gtgcagtgcg cccacctaaa gatcaacagc aactacaacg gccccgcgcc cggcccgacc    660
atcaagattc ccggagggta caagatcagc gatcctgcga ttcaatatga ccagtgggcg    720
cagccgccgc cgacgtacgc gcccatgccg ggaccgccgc tgtggcccaa caacaatcct    780
cagcagggca acccgaatca gggcggaaat aacggcggtg caaccaggg cggcggcaat    840 ggtggctgca ccgttccgaa gtggtatgta gagttcttca ctattatcat gagatgcagc    900
gttggacttg tgcttacacc tagaacaggg gccaatgcgg tggtcagggt tacagcgggt    960
gcaggaactg cgagtctggc tcgacatgcc gtgcccagaa cgactggtac tcgcagtgcc   1020
tgtaa                                                                1025
```

<210> SEQ ID NO 42
<211> LENGTH: 298
<212> TYPE: PRT
<213> ORGANISM: Humicola insolens

<400> SEQUENCE: 42

```
Met His Val Gln Ser Leu Leu Ala Gly Ala Leu Ala Leu Ala Pro Ser
1               5                   10                  15

Ala Ser Ala His Phe Leu Phe Pro His Leu Met Leu Asn Gly Val Arg
            20                  25                  30

Thr Gly Ala Tyr Glu Tyr Val Arg Glu His Asp Phe Gly Phe Met Pro
        35                  40                  45

His Asn Asn Asp Trp Ile Asn Ser Pro Asp Phe Arg Cys Asn Glu Gly
    50                  55                  60

Ser Trp Arg His Arg Arg Glu Pro Lys Thr Ala Val Val Thr Ala Gly
65                  70                  75                  80

Val Asp Val Val Gly Phe Asn Leu His Leu Asp Phe Asp Leu Tyr His
                85                  90                  95

Pro Gly Pro Val Thr Ile Tyr Leu Ser Arg Ala Pro Gly Asp Val Arg
            100                 105                 110

Asp Tyr Asp Gly Ser Gly Asp Trp Phe Lys Val Tyr Gln Leu Gly Thr
        115                 120                 125

Arg Gln Pro Phe Asn Gly Thr Asp Glu Gly Trp Ala Thr Trp Lys Met
    130                 135                 140

Lys Asn Trp Gln Phe Arg Leu Pro Ala Glu Ile Pro Ala Gly Glu Tyr
145                 150                 155                 160

Leu Met Arg Ile Glu Gln Met Ser Val His Pro Pro Tyr Arg Gln Lys
                165                 170                 175

Glu Trp Tyr Val Gln Cys Ala His Leu Lys Ile Asn Ser Asn Tyr Asn
            180                 185                 190

Gly Pro Ala Pro Gly Pro Thr Ile Lys Ile Pro Gly Gly Tyr Lys Ile
        195                 200                 205

Ser Asp Pro Ala Ile Gln Tyr Asp Gln Trp Ala Gln Pro Pro Thr
    210                 215                 220

Tyr Ala Pro Met Pro Gly Pro Pro Leu Trp Pro Asn Asn Asn Pro Gln
225                 230                 235                 240

Gln Gly Asn Pro Asn Gln Gly Gly Asn Gly Gly Asn Gln Gly
                245                 250                 255

Gly Gly Asn Gly Gly Cys Thr Val Pro Lys Trp Gly Gln Cys Gly Gly
            260                 265                 270

Gln Gly Tyr Ser Gly Cys Arg Asn Cys Glu Ser Gly Ser Thr Cys Arg
```

Ala Gln Asn Asp Trp Tyr Ser Gln Cys Leu
    290                 295

<210> SEQ ID NO 43
<211> LENGTH: 1035
<212> TYPE: DNA
<213> ORGANISM: Humicola insolens

<400> SEQUENCE: 43

| | | | | | |
|---|---|---|---|---|---|
| atgccaccac | cactactggc | caccgtcctc | tccttgctag | ccctcacccg | cggcgccctt | 60 |
| tcccattccc | acctagccca | cgtcatcatc | aacggccagc | tctaccacgg | cttcgaccca | 120 |
| cgtccaaacc | aaaacaacca | tccagcccgt | gtcggctggt | ccacgaccgc | cacagatgac | 180 |
| ggcttcgtca | ccccgggcaa | ttactcccat | cccgacatca | tctgccaccg | cggcggcgtc | 240 |
| agcccgcgcg | cccacgctcc | cgtcaccgcc | ggcggcaagg | tccaggtcca | atggaacggc | 300 |
| tggccgatcg | gacacgtcgg | gccgatcctg | acctacatcg | cgccgtgcgg | cggactgccg | 360 |
| ggcgccgaag | aagggtgtac | gggcgtggac | aaaaccgacc | tgcgtggac | caagatcgac | 420 |
| gactcgatgc | cgccgttccg | gtttaccgac | gccaccaagc | cagtctctgg | cagagcgcag | 480 |
| ttcccgatag | ccaggtctg | gcgacggat | cgctggtcg | aggcgaataa | tagctggtcg | 540 |
| gtggtcattc | ccaggaatat | cccgccgggg | ccgtacgttt | tgaggcagga | gattgtggcc | 600 |
| ctgcattacg | cggcgaagtt | gaacggggcg | cagaactatc | cgttgtgtct | gaacctctgg | 660 |
| gtggaaaagg | ggcagcagga | tcagggagag | cccttcaaat | tcgatgctta | cgacgcgagg | 720 |
| gagttttaca | gcgaggacca | tccgggtgtg | ttgattgatg | ttatgacgat | ggttgggccg | 780 |
| agagccgtgt | accggatacc | tggaccgacc | gtggccagtg | gtgccacgag | aattccgcac | 840 |
| tcattgcaga | cgagcgccga | gacgtgggtg | gaagggacgc | cggtggccgt | gacgagggcg | 900 |
| acggaaacgg | ttcagatgga | gataactacg | acacctgcag | gtcagggagc | tggtgtgagg | 960 |
| acagctaccc | ctgccatgcc | aacaccaaca | gtgacgaaga | ggtggaaggg | aagatttgag | 1020 |
| atgggtaggc | catga | | | | | 1035 |

<210> SEQ ID NO 44
<211> LENGTH: 344
<212> TYPE: PRT
<213> ORGANISM: Humicola insolens

<400> SEQUENCE: 44

Met Pro Pro Pro Leu Leu Ala Thr Val Leu Ser Leu Leu Ala Leu Thr
1               5                   10                  15

Arg Gly Ala Leu Ser His Ser His Leu Ala His Val Ile Ile Asn Gly
            20                  25                  30

Gln Leu Tyr His Gly Phe Asp Pro Arg Pro Asn Gln Asn Asn His Pro
        35                  40                  45

Ala Arg Val Gly Trp Ser Thr Thr Ala Thr Asp Asp Gly Phe Val Thr
    50                  55                  60

Pro Gly Asn Tyr Ser His Pro Asp Ile Ile Cys His Arg Gly Gly Val
65                  70                  75                  80

Ser Pro Arg Ala His Ala Pro Val Thr Ala Gly Lys Val Gln Val
            85                  90                  95

Gln Trp Asn Gly Trp Pro Ile Gly His Val Gly Pro Ile Leu Thr Tyr
        100                 105                 110

Ile Ala Pro Cys Gly Gly Leu Pro Gly Ala Glu Glu Gly Cys Thr Gly

```
                  115                 120                 125
Val Asp Lys Thr Asp Leu Arg Trp Thr Lys Ile Asp Asp Ser Met Pro
130                 135                 140

Pro Phe Arg Phe Thr Asp Ala Thr Lys Pro Val Ser Gly Arg Ala Gln
145                 150                 155                 160

Phe Pro Ile Gly Gln Val Trp Ala Thr Asp Ala Leu Val Glu Ala Asn
                165                 170                 175

Asn Ser Trp Ser Val Val Ile Pro Arg Asn Ile Pro Pro Gly Pro Tyr
            180                 185                 190

Val Leu Arg Gln Glu Ile Val Ala Leu His Tyr Ala Ala Lys Leu Asn
        195                 200                 205

Gly Ala Gln Asn Tyr Pro Leu Cys Leu Asn Leu Trp Val Glu Lys Gly
    210                 215                 220

Gln Gln Asp Gln Gly Glu Pro Phe Lys Phe Asp Ala Tyr Asp Ala Arg
225                 230                 235                 240

Glu Phe Tyr Ser Glu Asp His Pro Gly Val Leu Ile Asp Val Met Thr
                245                 250                 255

Met Val Gly Pro Arg Ala Val Tyr Arg Ile Pro Gly Pro Thr Val Ala
            260                 265                 270

Ser Gly Ala Thr Arg Ile Pro His Ser Leu Gln Thr Ser Ala Glu Thr
        275                 280                 285

Trp Val Glu Gly Thr Pro Val Ala Val Thr Arg Ala Thr Glu Thr Val
    290                 295                 300

Gln Met Glu Ile Thr Thr Thr Pro Ala Gly Gln Gly Ala Gly Val Arg
305                 310                 315                 320

Thr Ala Thr Pro Ala Met Pro Thr Pro Thr Val Thr Lys Arg Trp Lys
                325                 330                 335

Gly Arg Phe Glu Met Gly Arg Pro
            340
```

<210> SEQ ID NO 45
<211> LENGTH: 1057
<212> TYPE: DNA
<213> ORGANISM: Humicola insolens

<400> SEQUENCE: 45

```
atgaagtccc tgacctacgc cgcgctggcc gccctctggg cccagcagac cgctgctcat      60
gccaccttcc agcaactctg ggtcgacggc gtcgactacg gcagtcagtg cgcccgcctg     120
ccgccgtcca actcccccat cgccagcgtc acctcgaccg ccatgcgctg caacaacggt     180
ccccgcgctg ccgccaagtg ccccgtcaag gctggcggca ccgtcaccat cgagatgcac     240
caggttggtt tccttgaagt gttcccctac cacatataca gaccgtagct aacacaccca     300
tccttagcaa cccggtgacc ggtcctgcaa ccaggacgcc attggcggtg cccaccacgg     360
ccccgtgatg gtgtacatgt ccaaggtctc tgatgccttc accgccgacg gctcgtcagg     420
ctggttcaag atcttccagg acggctgggc caagaacccc aacggccgcg ttggcgacga     480
cgacttctgg ggcaccaagg acctcaacac ctgctgcggc aagatgaacg tcaagatccc     540
cgccgacatc gccccggcg actacctgct ccgcgccgag gccatcgcgc tgcacgccgc     600
cggcccccagc ggtggcgccc agccctacgt cacctgctac cagctcaccg tcacgggcgg     660
cggcaacgcc aacccgccca ccgtcaactt cccccggcgcc tacagcgagc gtgaccctgg     720
catcgccgtc agcatccacg cgctctgtc caactacgtc gtccccggtc tccggtctca     780
ctcgggcggc agcgagaagc gcgctggcag ccctgcgag ggctgcgagg ccacctgcaa      840
```

```
ggtcggctcg agccccagcc agactcttgc tccttccaac ccggccccga cctctcccgc      900
caacggcggc ggcaacaacg gtggtggcaa cactggcggc ggctgcaccg tgcccaagtg      960
gcagcagtgc ggcggccagg gctactcggg ctgcaccgtc tgcgagtctg gctcgacttg     1020
ccgcgctcag aaccagtggt actctcagtg cgtgtaa                              1057
```

<210> SEQ ID NO 46
<211> LENGTH: 330
<212> TYPE: PRT
<213> ORGANISM: Humicola insolens

<400> SEQUENCE: 46

```
Met Lys Ser Leu Thr Tyr Ala Ala Leu Ala Ala Leu Trp Ala Gln Gln
1               5                   10                  15

Thr Ala Ala His Ala Thr Phe Gln Gln Leu Trp Val Asp Gly Val Asp
            20                  25                  30

Tyr Gly Ser Gln Cys Ala Arg Leu Pro Pro Ser Asn Ser Pro Ile Ala
        35                  40                  45

Ser Val Thr Ser Thr Ala Met Arg Cys Asn Asn Gly Pro Arg Ala Ala
    50                  55                  60

Ala Lys Cys Pro Val Lys Ala Gly Gly Thr Val Thr Ile Glu Met His
65                  70                  75                  80

Gln Gln Pro Gly Asp Arg Ser Cys Asn Gln Asp Ala Ile Gly Gly Ala
                85                  90                  95

His His Gly Pro Val Met Val Tyr Met Ser Lys Val Ser Asp Ala Phe
            100                 105                 110

Thr Ala Asp Gly Ser Ser Gly Trp Phe Lys Ile Phe Gln Asp Gly Trp
        115                 120                 125

Ala Lys Asn Pro Asn Gly Arg Val Gly Asp Asp Phe Trp Gly Thr
    130                 135                 140

Lys Asp Leu Asn Thr Cys Cys Gly Lys Met Asn Val Lys Ile Pro Ala
145                 150                 155                 160

Asp Ile Ala Pro Gly Asp Tyr Leu Leu Arg Ala Glu Ala Ile Ala Leu
                165                 170                 175

His Ala Ala Gly Pro Ser Gly Gly Ala Gln Pro Tyr Val Thr Cys Tyr
            180                 185                 190

Gln Leu Thr Val Thr Gly Gly Gly Asn Ala Asn Pro Pro Thr Val Asn
        195                 200                 205

Phe Pro Gly Ala Tyr Ser Glu Arg Asp Pro Gly Ile Ala Val Ser Ile
    210                 215                 220

His Gly Ala Leu Ser Asn Tyr Val Val Pro Gly Pro Pro Val Tyr Ser
225                 230                 235                 240

Gly Gly Ser Glu Lys Arg Ala Gly Ser Pro Cys Glu Gly Cys Glu Ala
                245                 250                 255

Thr Cys Lys Val Gly Ser Ser Pro Ser Gln Thr Leu Ala Pro Ser Asn
            260                 265                 270

Pro Ala Pro Thr Ser Pro Ala Asn Gly Gly Asn Asn Gly Gly Gly
        275                 280                 285

Asn Thr Gly Gly Gly Cys Thr Val Pro Lys Trp Gln Gln Cys Gly Gly
    290                 295                 300

Gln Gly Tyr Ser Gly Cys Thr Val Cys Glu Ser Gly Ser Thr Cys Arg
305                 310                 315                 320

Ala Gln Asn Gln Trp Tyr Ser Gln Cys Val
                325                 330
```

<210> SEQ ID NO 47
<211> LENGTH: 772
<212> TYPE: DNA
<213> ORGANISM: Humicola insolens

<400> SEQUENCE: 47

```
atgaagctcc tcctccccgc cctcctggct ctggccgccg agtccgtctc ggcgcactac      60
atcttccaac aactcaccgt cgccggcacc aagtaccccg tgtggaagta catccggcgc     120
aacagcaatc cggcgtggct tcaaaacggc cctgtgaccg acctcgcctc gaccgacctg     180
cgctgcaacg tgggcgggca ggtcagcaac ggcaccgaga ctctcaccgt ccgcgcgggc     240
gaccagttca cgttccacct cgacacggcg gtgtaccacc agggcccgac ctcgctgtac     300
atgtcgcgcg ctccgggcaa ggtggaggac tatgatggca gcgggccgtg gtttaagatt     360
tatgattggg ggccgacagg gaataattgg gtcatgaggg gtatggtttc ccctattaat     420
tattattatt gtttacttgg ggcatcatct ggtggtggtg ctggtgacga tgataagagt     480
gatggagaag gacctggctg acgacctaaa aacccgatca gattcgtaca cgtacaacat     540
cccccgctgc atccccgacg gcgagtatct cctgcgcatc cagcagctgg gtctgcacaa     600
tccgggcgcc gcgccgcagt tctacatcag ctgcgcccag atcaaggtca ccggcggcgg     660
cactaccaac ccgaccccca cggctctgat tccgggagcg ttcagggcta cggatccggg     720
atacactgtc aacgtaagtc aaactttgag caactccata tcaacctcgt ga             772
```

<210> SEQ ID NO 48
<211> LENGTH: 216
<212> TYPE: PRT
<213> ORGANISM: Humicola insolens

<400> SEQUENCE: 48

```
Met Lys Leu Leu Leu Pro Ala Leu Leu Ala Leu Ala Ala Glu Ser Val
1               5                   10                  15

Ser Ala His Tyr Ile Phe Gln Gln Leu Thr Val Ala Gly Thr Lys Tyr
            20                  25                  30

Pro Val Trp Lys Tyr Ile Arg Arg Asn Ser Asn Pro Ala Trp Leu Gln
        35                  40                  45

Asn Gly Pro Val Thr Asp Leu Ala Ser Thr Asp Leu Arg Cys Asn Val
    50                  55                  60

Gly Gly Gln Val Ser Asn Gly Thr Glu Thr Leu Thr Val Arg Ala Gly
65                  70                  75                  80

Asp Gln Phe Thr Phe His Leu Asp Thr Ala Val Tyr His Gln Gly Pro
                85                  90                  95

Thr Ser Leu Tyr Met Ser Arg Ala Pro Gly Lys Val Glu Asp Tyr Asp
            100                 105                 110

Gly Ser Gly Pro Trp Phe Lys Ile Tyr Asp Trp Gly Pro Thr Gly Asn
        115                 120                 125

Asn Trp Val Met Arg Asp Ser Tyr Thr Tyr Asn Ile Pro Arg Cys Ile
    130                 135                 140

Pro Asp Gly Glu Tyr Leu Leu Arg Ile Gln Gln Leu Gly Leu His Asn
145                 150                 155                 160

Pro Gly Ala Ala Pro Gln Phe Tyr Ile Ser Cys Ala Gln Ile Lys Val
                165                 170                 175

Thr Gly Gly Gly Thr Thr Asn Pro Thr Pro Thr Ala Leu Ile Pro Gly
            180                 185                 190
```

```
Ala Phe Arg Ala Thr Asp Pro Gly Tyr Thr Val Asn Val Ser Gln Thr
        195                 200                 205

Leu Ser Asn Ser Ile Ser Thr Ser
        210                 215

<210> SEQ ID NO 49
<211> LENGTH: 1536
<212> TYPE: DNA
<213> ORGANISM: Humicola insolens

<400> SEQUENCE: 49
atgcgttctg tttcccttct tgcggccgct ttcgcgccgc tggctacggc acacacggtc      60
tttacagctc tttttcatcaa caatgtccac cagggcgacg gcacttgcgt ccgtatggct    120
aagcagggca acctcgccac ccatcccgtc agtctgaaca gcaatgagat ggcctgcgt     180 gggtaggccc cgttcctcga gcagctgatc tcgaactaac atgttgattc ttgaactcca    240
ggtcgcgatg ccaacaacc agtggcattt acttgcccag cacctgcggg agccaagctg     300
accttattgt ttcgtatgtg ggcagatggc tctcagccag gttccatcga caagtctcac    360
gttggtccca tgtccatcta cctcaagaaa gtctcagata tgaacaccga ctcggccgca    420
gggcccgggt ggttcaagat ctggagtgag gctacgacg ctgcgacgaa gaaatgggcc    480
acggagaaac tcatcgccaa caacggtttg ctcagcgtca acctacctcc cggcctccct    540
gcaggctact acctcgcccg ccacgaaatc gtcactctcc aaaacgtcac caacaacaag   600
gccgatccgc agttctacgt cggctgtgcg cagctgttcg tccaagggtt gggcaccgcc    660
gcctccgtgc ctgctgacaa aaccgtttcc atccccggcc atctgaaccc caacgacccg   720
gcgctggtat tcaaccccta tacccaaaac gctgcgacat acccaagctt cggcccaccg    780
ctcttcttcc caaatgctgc ttcggcggga tcaaacaagg cccagtcaac actcaagcaa    840
acctccggcg tcatccctc cgactgcctc atcaaaaacg ccaactggtg cggccgtgaa    900
gttccagact ataccaacga ggcgggatgc tggacggcgg cggggaactg ttgggagcag   960
gctgatcaat gctacaagac agccccgcca tcgggccata agggatgcaa gacctgggag   1020
gagcagaagt gcaacgtcat ccagaactcc tgtgaagcga agaggttttc gggcccgcca   1080 aacaggggg tcaagtttgc tgatatggat gtgaatcagc ttgttccggg ggcgatccct   1140
gaagcagtga acgccggtca gaatggggag gcggttgttg ttgacggcac aacgagctct   1200
gcagatgaga aggcgagtgt ggatttgaca acatcgtctc taccgacgcc gacgcctgcg   1260
gctgaagaaa acgggaagga ggatgaaaga ctggctcttg atccgaccct gacggaggac   1320
gagtcgtttt tctcagttga gccaacgtct gagcccactg gtgttcaggt tgaggtgcct   1380
ttgacaactg tggtcctcct tccaacgctc acctcatctt tgaatccatt gccaaccccg   1440
acctcaattt cccagccggc tcacccggga agaccatgca caggtcgccg tcgtaggccg   1500
aggccagggt ttccgaaaca cccgcgcgat tttaa                              1536

<210> SEQ ID NO 50
<211> LENGTH: 490
<212> TYPE: PRT
<213> ORGANISM: Humicola insolens

<400> SEQUENCE: 50

Met Arg Ser Val Ser Leu Leu Ala Ala Ala Phe Ala Pro Leu Ala Thr
1               5                   10                  15

Ala His Thr Val Phe Thr Ala Leu Phe Ile Asn Asn Val His Gln Gly
            20                  25                  30
```

```
Asp Gly Thr Cys Val Arg Met Ala Lys Gln Gly Asn Leu Ala Thr His
         35                  40                  45
Pro Val Ser Leu Asn Ser Asn Glu Met Ala Cys Gly Arg Asp Gly Gln
 50                  55                  60
Gln Pro Val Ala Phe Thr Cys Pro Ala Pro Ala Gly Ala Lys Leu Thr
 65                  70                  75                  80
Leu Leu Phe Arg Met Trp Ala Asp Gly Ser Gln Pro Gly Ser Ile Asp
                 85                  90                  95
Lys Ser His Val Gly Pro Met Ser Ile Tyr Leu Lys Lys Val Ser Asp
                100                 105                 110
Met Asn Thr Asp Ser Ala Ala Gly Pro Gly Trp Phe Lys Ile Trp Ser
                115                 120                 125
Glu Gly Tyr Asp Ala Ala Thr Lys Lys Trp Ala Thr Glu Lys Leu Ile
        130                 135                 140
Ala Asn Asn Gly Leu Leu Ser Val Asn Leu Pro Pro Gly Leu Pro Ala
145                 150                 155                 160
Gly Tyr Tyr Leu Ala Arg His Glu Ile Val Thr Leu Gln Asn Val Thr
                    165                 170                 175
Asn Asn Lys Ala Asp Pro Gln Phe Tyr Val Gly Cys Ala Gln Leu Phe
                180                 185                 190
Val Gln Gly Leu Gly Thr Ala Ala Ser Val Pro Ala Asp Lys Thr Val
        195                 200                 205
Ser Ile Pro Gly His Leu Asn Pro Asn Asp Pro Ala Leu Val Phe Asn
210                 215                 220
Pro Tyr Thr Gln Asn Ala Ala Thr Tyr Pro Ser Phe Gly Pro Pro Leu
225                 230                 235                 240
Phe Phe Pro Asn Ala Ala Ser Ala Gly Ser Asn Lys Ala Gln Ser Thr
                245                 250                 255
Leu Lys Gln Thr Ser Gly Val Ile Pro Ser Asp Cys Leu Ile Lys Asn
                260                 265                 270
Ala Asn Trp Cys Gly Arg Glu Val Pro Asp Tyr Thr Asn Glu Ala Gly
            275                 280                 285
Cys Trp Thr Ala Ala Gly Asn Cys Trp Glu Gln Ala Asp Gln Cys Tyr
290                 295                 300
Lys Thr Ala Pro Pro Ser Gly His Lys Gly Cys Lys Thr Trp Glu Glu
305                 310                 315                 320
Gln Lys Cys Asn Val Ile Gln Asn Ser Cys Glu Ala Lys Arg Phe Ser
                325                 330                 335
Gly Pro Pro Asn Arg Gly Val Lys Phe Ala Asp Met Asp Val Asn Gln
                340                 345                 350
Leu Val Pro Gly Ala Ile Pro Glu Ala Val Asn Ala Gly Gln Asn Gly
            355                 360                 365
Glu Ala Val Val Asp Gly Thr Thr Ser Ser Ala Asp Glu Lys Ala
370                 375                 380
Ser Val Asp Leu Thr Thr Ser Ser Leu Pro Thr Pro Thr Pro Ala Ala
385                 390                 395                 400
Glu Glu Asn Gly Lys Glu Asp Glu Arg Leu Ala Leu Asp Pro Thr Leu
                405                 410                 415
Thr Glu Asp Glu Ser Phe Phe Ser Val Glu Pro Thr Ser Glu Pro Thr
                420                 425                 430
Gly Val Gln Val Glu Val Pro Leu Thr Thr Val Leu Leu Pro Thr
            435                 440                 445
```

```
Leu Thr Ser Ser Leu Asn Pro Leu Pro Thr Pro Thr Ser Ile Ser Gln
        450                 455                 460

Pro Ala His Pro Gly Arg Pro Cys Thr Gly Arg Arg Arg Pro Arg
465                 470                 475                 480

Pro Gly Phe Pro Lys His Pro Arg Asp Phe
                485                 490

<210> SEQ ID NO 51
<211> LENGTH: 921
<212> TYPE: DNA
<213> ORGANISM: Humicola insolens

<400> SEQUENCE: 51
atgttcttcc gcaacgccgc cactcttgct ctggcctacg ccaccaccgg cgtctcggcc     60
cacgcgctca tgtacggcgt ctgggtcaac ggcgtcgacc aaggcgacgg ccgcaacgtc    120
tacatccgca cgcccccaa caacagcccg gtcaaagacc tcgccagccc ggacatcgtc     180
tgcaacgtca acggcgggcg cgccgttccg gacttcgtcc aggcctcggc gggggacacc    240
ctcaccttcg agtggctgca acacccgc ggcgacgaca tcatcgaccg ctcccacctc      300
ggccccatca tcacctacat cgcccctttt accacgggca acccgacggg gcccgtctgg    360
accaaaatcg ccgaacaggg cttcaaccct ccacccgcc gctgggccgt cgacgatctg     420
atcgacaacg gcggcaagac cgacttcgtc ctgcccgcgt ccctcgcgcc gggcaggtac    480
atcatccggc aggagatcat cgcgcaccac gagtccgaaa ccacgttcga atccaacccg    540
gcgcggggtg cccagttcta cccgtcgtgc gtgcagatcc aagtctcttc tggctcgggc    600
accgccgtgc cggatcagaa ctttgacttc aacacgggct acacgtacgc cgaccccggc    660
atccacttca acatctacac ctcgttcaac agctactcca tccccggccc ggaggtttgg    720
acgggcgcta gcaccggcgg cggcaacggc aacggcaacg caacggcaa tgccacgcct     780 acgcagccta ctcccactcc cactgtcact cccactccca tcgagaccgc ccagccggtt    840
accacgacga ccacctcgac ccggccgttc cctacccgct gccctggccg ccgcctcaag    900
cgtgaggagc ccaaggcttg a                                              921

<210> SEQ ID NO 52
<211> LENGTH: 306
<212> TYPE: PRT
<213> ORGANISM: Humicola insolens

<400> SEQUENCE: 52

Met Phe Phe Arg Asn Ala Ala Thr Leu Ala Leu Ala Tyr Ala Thr Thr
1               5                   10                  15

Gly Val Ser Ala His Ala Leu Met Tyr Gly Val Trp Val Asn Gly Val
            20                  25                  30

Asp Gln Gly Asp Gly Arg Asn Val Tyr Ile Arg Thr Pro Pro Asn Asn
        35                  40                  45

Ser Pro Val Lys Asp Leu Ala Ser Pro Asp Ile Val Cys Asn Val Asn
    50                  55                  60

Gly Gly Arg Ala Val Pro Asp Phe Val Gln Ala Ser Ala Gly Asp Thr
65                  70                  75                  80

Leu Thr Phe Glu Trp Leu His Asn Thr Arg Gly Asp Asp Ile Ile Asp
                85                  90                  95

Arg Ser His Leu Gly Pro Ile Ile Thr Tyr Ile Ala Pro Phe Thr Thr
            100                 105                 110

Gly Asn Pro Thr Gly Pro Val Trp Thr Lys Ile Ala Glu Gln Gly Phe
```

|  |  |  | 115 |  |  |  | 120 |  |  |  | 125 |  |
|---|---|---|---|---|---|---|---|---|---|---|---|---|

Asn Pro Ser Thr Arg Arg Trp Ala Val Asp Asp Leu Ile Asp Asn Gly
                    130                 135                 140

Gly Lys Thr Asp Phe Val Leu Pro Ala Ser Leu Ala Pro Gly Arg Tyr
145                 150                 155                 160

Ile Ile Arg Gln Glu Ile Ile Ala His His Glu Ser Glu Thr Thr Phe
                165                 170                 175

Glu Ser Asn Pro Ala Arg Gly Ala Gln Phe Tyr Pro Ser Cys Val Gln
            180                 185                 190

Ile Gln Val Ser Ser Gly Ser Gly Thr Ala Val Pro Asp Gln Asn Phe
        195                 200                 205

Asp Phe Asn Thr Gly Tyr Thr Tyr Ala Asp Pro Gly Ile His Phe Asn
    210                 215                 220

Ile Tyr Thr Ser Phe Asn Ser Tyr Ser Ile Pro Gly Pro Glu Val Trp
225                 230                 235                 240

Thr Gly Ala Ser Thr Gly Gly Asn Gly Asn Gly Asn Gly Asn Gly
                    245                 250                 255

Asn Ala Thr Pro Thr Gln Pro Thr Pro Thr Pro Thr Val Thr Pro Thr
                260                 265                 270

Pro Ile Glu Thr Ala Gln Pro Val Thr Thr Thr Thr Ser Thr Arg
            275                 280                 285

Pro Phe Pro Thr Arg Cys Pro Gly Arg Arg Leu Lys Arg Glu Glu Pro
    290                 295                 300

Lys Ala
305

<210> SEQ ID NO 53
<211> LENGTH: 1092
<212> TYPE: DNA
<213> ORGANISM: Humicola insolens

<400> SEQUENCE: 53

| atggctcatc catgggcacg ttgcgtctat acagccatct ggctcgctgc ctccgcttct | 60 |
|---|---|
| ggacgtaggt acaagactcc ggcagtgcca tttatgaacc acaacgtgg actggtcccg | 120 |
| tgctaacaca tcacagactc gcgcgtttgg agtgtctcgg tcaatggacg ctaccaggga | 180 |
| ccgggtgttg atgactacct gcgcgcaccg ccaagtgact ctccggtggt ggacctggac | 240 |
| tcaccaaccc tcaactgcaa tgtcaatgga acaagcctg ttccagggtt tgttgaggtg | 300 |
| tctgcgggag attctctgga atggaagtgg tactacatca cccgtacaa cccaagcgac | 360 |
| atgatcatcg cggcagaaca ccgcggaccg atcatcacct acatcacgaa ttacaccgat | 420 |
| ggccagcctc aaggagctgt ctggaccaag attgatcacg aaggctacga tcctgtgaca | 480 |
| gaccggttcg ccgtcgacaa cttgatcgcc aacagggat ggaaagcaat caagcttccc | 540 |
| atgctcgccg acgggaagta catcctgcga caggagatca tcgcactcca cagcgcacac | 600 |
| aaccaaggcg gggcccagct gtatccgaac tgcattcaga tcaaggtcgt tggtggcaag | 660 |
| ggaagcgcgg tgcccaacca gaactttgat ctcaacaagg ggtacacatc cgatcacccg | 720 |
| ggacttcggt tcaacctgtg caaccattc aacaattaca ccattcccgg tcctgaggtc | 780 |
| tggaagggag ttgtggttgc gagcaatggt acaacgaaca gcaccacaaa tctccaccaac | 840 |
| aacaccggca ccggttttgc gaacagcact atggccactg gtgaaacaag gaccgagagg | 900 |
| agttttatga cacttaccgc atcacattca gactactggcg tccccgccaa atctcatact | 960 |
| gtggctgtaa gctggacaac atccgccgcc gttgttgggt ctccgattag cgttaccaca | 1020 | actttcagtt cctttaccac aacaccggtt ccgacgaact ctaccggtgc ttatctctac    1080 cggtacaagt ga    1092

<210> SEQ ID NO 54
<211> LENGTH: 339
<212> TYPE: PRT
<213> ORGANISM: Humicola insolens

<400> SEQUENCE: 54

Met Ala His Pro Trp Ala Arg Cys Val Tyr Thr Ala Ile Trp Leu Ala
1               5                   10                  15

Ala Ser Ala Ser Gly His Ser Arg Val Trp Ser Val Ser Val Asn Gly
            20                  25                  30

Arg Tyr Gln Gly Pro Gly Val Asp Asp Tyr Leu Arg Ala Pro Pro Ser
        35                  40                  45

Asp Ser Pro Val Val Asp Leu Asp Ser Pro Thr Leu Asn Cys Asn Val
    50                  55                  60

Asn Gly Asn Lys Pro Val Pro Gly Phe Val Glu Val Ser Ala Gly Asp
65                  70                  75                  80

Ser Leu Glu Trp Lys Trp Tyr Tyr Ile Asn Pro Tyr Asn Pro Ser Asp
                85                  90                  95

Met Ile Ile Ala Ala Glu His Arg Gly Pro Ile Ile Thr Tyr Ile Thr
            100                 105                 110

Asn Tyr Thr Asp Gly Gln Pro Gln Gly Ala Val Trp Thr Lys Ile Asp
        115                 120                 125

His Glu Gly Tyr Asp Pro Val Thr Asp Arg Phe Ala Val Asp Asn Leu
    130                 135                 140

Ile Ala Asn Arg Gly Trp Lys Ala Ile Lys Leu Pro Met Leu Ala Asp
145                 150                 155                 160

Gly Lys Tyr Ile Leu Arg Gln Glu Ile Ile Ala Leu His Ser Ala His
                165                 170                 175

Asn Gln Gly Gly Ala Gln Leu Tyr Pro Asn Cys Ile Gln Ile Lys Val
            180                 185                 190

Val Gly Gly Lys Gly Ser Ala Val Pro Asn Gln Asn Phe Asp Leu Asn
        195                 200                 205

Lys Gly Tyr Thr Ser Asp His Pro Gly Leu Arg Phe Asn Leu Trp Gln
    210                 215                 220

Pro Phe Asn Asn Tyr Thr Ile Pro Gly Pro Glu Val Trp Lys Gly Val
225                 230                 235                 240

Val Val Ala Ser Asn Gly Thr Thr Asn Ser Thr Thr Asn Leu Thr Asn
                245                 250                 255

Asn Thr Gly Thr Gly Phe Ala Asn Ser Thr Met Ala Thr Gly Glu Thr
            260                 265                 270

Arg Thr Glu Arg Ser Phe Met Thr Leu Thr Ala Ser His Ser Asp Thr
        275                 280                 285

Gly Val Pro Ala Lys Ser His Thr Val Ala Val Ser Trp Thr Thr Ser
    290                 295                 300

Ala Ala Val Val Gly Ser Pro Ile Ser Val Thr Thr Thr Phe Ser Ser
305                 310                 315                 320

Phe Thr Thr Thr Pro Val Pro Thr Asn Ser Thr Gly Ala Tyr Leu Tyr
                325                 330                 335

Arg Tyr Lys

```
<210> SEQ ID NO 55
<211> LENGTH: 42
<212> TYPE: DNA
<213> ORGANISM: Artificial Sequence
<220> FEATURE:
<223> OTHER INFORMATION: Synthetic Construct

<400> SEQUENCE: 55
acacaactgg ggatccacca tgaagctcag cgttgtcctc ac                              42

<210> SEQ ID NO 56
<211> LENGTH: 35
<212> TYPE: DNA
<213> ORGANISM: Artificial Sequence
<220> FEATURE:
<223> OTHER INFORMATION: Synthetic Construct

<400> SEQUENCE: 56
gtcaccctct agatcttcag cacgtctcaa ccggc                                     35

<210> SEQ ID NO 57
<211> LENGTH: 35
<212> TYPE: DNA
<213> ORGANISM: Artificial Sequence
<220> FEATURE:
<223> OTHER INFORMATION: Synthetic Construct

<400> SEQUENCE: 57
acacaactgg ggatccacca tgcgcccctt cctcg                                     35

<210> SEQ ID NO 58
<211> LENGTH: 38
<212> TYPE: DNA
<213> ORGANISM: Artificial Sequence
<220> FEATURE:
<223> OTHER INFORMATION: Synthetic Construct

<400> SEQUENCE: 58
gtcaccctct agatctttac tcagactcgg ggcacgtc                                  38

<210> SEQ ID NO 59
<211> LENGTH: 43
<212> TYPE: DNA
<213> ORGANISM: Artificial Sequence
<220> FEATURE:
<223> OTHER INFORMATION: Synthetic Construct

<400> SEQUENCE: 59
acacaactgg ggatccacca tgagactctc cctgacaacc ctc                            43

<210> SEQ ID NO 60
<211> LENGTH: 35
<212> TYPE: DNA
<213> ORGANISM: Artificial Sequence
<220> FEATURE:
<223> OTHER INFORMATION: Synthetic Construct

<400> SEQUENCE: 60
gtcaccctct agatcttcag cactgaatcg gctcc                                     35

<210> SEQ ID NO 61
<211> LENGTH: 36
<212> TYPE: DNA
<213> ORGANISM: Artificial Sequence
<220> FEATURE:
<223> OTHER INFORMATION: Synthetic Construct
```

<400> SEQUENCE: 61
acacaactgg ggatccacca tgggaccgac ctgggc                      36

<210> SEQ ID NO 62
<211> LENGTH: 33
<212> TYPE: DNA
<213> ORGANISM: Artificial Sequence
<220> FEATURE:
<223> OTHER INFORMATION: Synthetic Construct

<400> SEQUENCE: 62
gtcaccctct agatcttcac cccgtccaca ccg                         33

<210> SEQ ID NO 63
<211> LENGTH: 40
<212> TYPE: DNA
<213> ORGANISM: Artificial Sequence
<220> FEATURE:
<223> OTHER INFORMATION: Synthetic Construct

<400> SEQUENCE: 63
acacaactgg ggatccacca tgaaggccct caccctcctc                  40

<210> SEQ ID NO 64
<211> LENGTH: 39
<212> TYPE: DNA
<213> ORGANISM: Artificial Sequence
<220> FEATURE:
<223> OTHER INFORMATION: Synthetic Construct

<400> SEQUENCE: 64
gtcaccctct agatctttac aagcactgcg aataccacg                   39

<210> SEQ ID NO 65
<211> LENGTH: 39
<212> TYPE: DNA
<213> ORGANISM: Artificial Sequence
<220> FEATURE:
<223> OTHER INFORMATION: Synthetic Construct

<400> SEQUENCE: 65
acacaactgg ggatccacca tggctcccaa gacctcgac                   39

<210> SEQ ID NO 66
<211> LENGTH: 41
<212> TYPE: DNA
<213> ORGANISM: Artificial Sequence
<220> FEATURE:
<223> OTHER INFORMATION: Synthetic Construct

<400> SEQUENCE: 66
gtcaccctct agatctttag atgcactgcg agtaccagtc g                41

<210> SEQ ID NO 67
<211> LENGTH: 43
<212> TYPE: DNA
<213> ORGANISM: Artificial Sequence
<220> FEATURE:
<223> OTHER INFORMATION: Synthetic Construct

<400> SEQUENCE: 67
acacaactgg ggatccacca tgtatctttt acctatcgcc gcg              43

<210> SEQ ID NO 68
<211> LENGTH: 39

<212> TYPE: DNA
<213> ORGANISM: Artificial Sequence
<220> FEATURE:
<223> OTHER INFORMATION: Synthetic Construct

<400> SEQUENCE: 68
gtcaccctct agatctttat ccgtgttggt tcaccttgg                                39

<210> SEQ ID NO 69
<211> LENGTH: 42
<212> TYPE: DNA
<213> ORGANISM: Artificial Sequence
<220> FEATURE:
<223> OTHER INFORMATION: Synthetic Construct

<400> SEQUENCE: 69
acacaactgg ggatccacca tgaagctcct cgctcctctg at                           42

<210> SEQ ID NO 70
<211> LENGTH: 38
<212> TYPE: DNA
<213> ORGANISM: Artificial Sequence
<220> FEATURE:
<223> OTHER INFORMATION: Synthetic Construct

<400> SEQUENCE: 70
gtcaccctct agatctttag cacttgaaga catcgggg                                38

<210> SEQ ID NO 71
<211> LENGTH: 41
<212> TYPE: DNA
<213> ORGANISM: Artificial Sequence
<220> FEATURE:
<223> OTHER INFORMATION: Synthetic Construct

<400> SEQUENCE: 71
acacaactgg ggatccacca tgaagctcct ctcaaccctc g                            41

<210> SEQ ID NO 72
<211> LENGTH: 38
<212> TYPE: DNA
<213> ORGANISM: Artificial Sequence
<220> FEATURE:
<223> OTHER INFORMATION: Synthetic Construct

<400> SEQUENCE: 72
gtcaccctct agatctttag ttgccatccc acaccttg                                38

<210> SEQ ID NO 73
<211> LENGTH: 39
<212> TYPE: DNA
<213> ORGANISM: Artificial Sequence
<220> FEATURE:
<223> OTHER INFORMATION: Synthetic Construct

<400> SEQUENCE: 73
acacaactgg ggatccacca tgctgggaag cgctcttct                               39

<210> SEQ ID NO 74
<211> LENGTH: 36
<212> TYPE: DNA
<213> ORGANISM: Artificial Sequence
<220> FEATURE:
<223> OTHER INFORMATION: Synthetic Construct

<400> SEQUENCE: 74

```
gtcaccctct agatctttag cactggaaga ccgggg                                         36
```

<210> SEQ ID NO 75
<211> LENGTH: 40
<212> TYPE: DNA
<213> ORGANISM: Artificial Sequence
<220> FEATURE:
<223> OTHER INFORMATION: Synthetic Construct

<400> SEQUENCE: 75

```
acacaactgg ggatccacca tgaagctgct tcctgggttg                                     40
```

<210> SEQ ID NO 76
<211> LENGTH: 33
<212> TYPE: DNA
<213> ORGANISM: Artificial Sequence
<220> FEATURE:
<223> OTHER INFORMATION: Synthetic Construct

<400> SEQUENCE: 76

```
gtcaccctct agatcttcag ccacgccaca cgg                                            33
```

<210> SEQ ID NO 77
<211> LENGTH: 41
<212> TYPE: DNA
<213> ORGANISM: Artificial Sequence
<220> FEATURE:
<223> OTHER INFORMATION: Synthetic Construct

<400> SEQUENCE: 77

```
acacaactgg ggatccacca tgctcctgaa ctcggtcatc g                                   41
```

<210> SEQ ID NO 78
<211> LENGTH: 33
<212> TYPE: DNA
<213> ORGANISM: Artificial Sequence
<220> FEATURE:
<223> OTHER INFORMATION: Synthetic Construct

<400> SEQUENCE: 78

```
gtcaccctct agatctttac tcgccgcgcc aga                                            33
```

<210> SEQ ID NO 79
<211> LENGTH: 41
<212> TYPE: DNA
<213> ORGANISM: Artificial Sequence
<220> FEATURE:
<223> OTHER INFORMATION: Synthetic Construct

<400> SEQUENCE: 79

```
acacaactgg ggatccacca tgaagctcac cacctccatc g                                   41
```

<210> SEQ ID NO 80
<211> LENGTH: 34
<212> TYPE: DNA
<213> ORGANISM: Artificial Sequence
<220> FEATURE:
<223> OTHER INFORMATION: Synthetic Construct

<400> SEQUENCE: 80

```
gtcaccctct agatcttcag cacttcaccg gcgc                                           34
```

<210> SEQ ID NO 81
<211> LENGTH: 40
<212> TYPE: DNA
<213> ORGANISM: Artificial Sequence
<220> FEATURE:
<223> OTHER INFORMATION: Synthetic Construct

<400> SEQUENCE: 81
acacaactgg ggatccacca tgaagactct cgcatccgcc        40

<210> SEQ ID NO 82
<211> LENGTH: 41
<212> TYPE: DNA
<213> ORGANISM: Artificial Sequence
<220> FEATURE:
<223> OTHER INFORMATION: Synthetic Construct

<400> SEQUENCE: 82
gtcaccctct agatcttcag aaaaagctcc catcaatgac a        41

<210> SEQ ID NO 83
<211> LENGTH: 40
<212> TYPE: DNA
<213> ORGANISM: Artificial Sequence
<220> FEATURE:
<223> OTHER INFORMATION: Synthetic Construct

<400> SEQUENCE: 83
acacaactgg ggatccacca tgcctcgctt caccaagtcc        40

<210> SEQ ID NO 84
<211> LENGTH: 36
<212> TYPE: DNA
<213> ORGANISM: Artificial Sequence
<220> FEATURE:
<223> OTHER INFORMATION: Synthetic Construct

<400> SEQUENCE: 84
gtcaccctct agatcttcaa gcaaccacct gcacac        36

<210> SEQ ID NO 85
<211> LENGTH: 42
<212> TYPE: DNA
<213> ORGANISM: Artificial Sequence
<220> FEATURE:
<223> OTHER INFORMATION: Synthetic Construct

<400> SEQUENCE: 85
acacaactgg ggatccacca tgaagggact tctcagcatc gc        42

<210> SEQ ID NO 86
<211> LENGTH: 46
<212> TYPE: DNA
<213> ORGANISM: Artificial Sequence
<220> FEATURE:
<223> OTHER INFORMATION: Synthetic Construct

<400> SEQUENCE: 86
gtcaccctct agatctttag atgcactgag aatagtaagc gttctg        46

<210> SEQ ID NO 87
<211> LENGTH: 40
<212> TYPE: DNA
<213> ORGANISM: Artificial Sequence
<220> FEATURE:
<223> OTHER INFORMATION: Synthetic Construct

<400> SEQUENCE: 87
acacaactgg ggatccacca tgaggccctt ctcactcgtc        40

<210> SEQ ID NO 88
<211> LENGTH: 42
<212> TYPE: DNA
<213> ORGANISM: Artificial Sequence
<220> FEATURE:
<223> OTHER INFORMATION: Synthetic Construct

<400> SEQUENCE: 88
gtcaccctct agatctctaa ggcgtacact gcgagtacca gt                    42

<210> SEQ ID NO 89
<211> LENGTH: 45
<212> TYPE: DNA
<213> ORGANISM: Artificial Sequence
<220> FEATURE:
<223> OTHER INFORMATION: Synthetic Construct

<400> SEQUENCE: 89
acacaactgg ggatccacca tggtgttgcg gtctctctct atcct                 45

<210> SEQ ID NO 90
<211> LENGTH: 43
<212> TYPE: DNA
<213> ORGANISM: Artificial Sequence
<220> FEATURE:
<223> OTHER INFORMATION: Synthetic Construct

<400> SEQUENCE: 90
gtcaccctct agatcttcat aacgtcatta tcgttgtttg cgt                   43

<210> SEQ ID NO 91
<211> LENGTH: 38
<212> TYPE: DNA
<213> ORGANISM: Artificial Sequence
<220> FEATURE:
<223> OTHER INFORMATION: Synthetic Construct

<400> SEQUENCE: 91
acacaactgg ggatccacca tgaggaccgt cttcgccg                         38

<210> SEQ ID NO 92
<211> LENGTH: 39
<212> TYPE: DNA
<213> ORGANISM: Artificial Sequence
<220> FEATURE:
<223> OTHER INFORMATION: Synthetic Construct

<400> SEQUENCE: 92
gtcaccctct agatctttag aaagcaggct ggcactgag                        39

<210> SEQ ID NO 93
<211> LENGTH: 38
<212> TYPE: DNA
<213> ORGANISM: Artificial Sequence
<220> FEATURE:
<223> OTHER INFORMATION: Synthetic Construct

<400> SEQUENCE: 93
acacaactgg ggatccacca tgaggctccc ccaagtgg                         38

<210> SEQ ID NO 94
<211> LENGTH: 43
<212> TYPE: DNA
<213> ORGANISM: Artificial Sequence
<220> FEATURE:
<223> OTHER INFORMATION: Synthetic Construct

<400> SEQUENCE: 94
gtcaccctct agatctttag ccaccaatcg agtcaaagta ctc        43

<210> SEQ ID NO 95
<211> LENGTH: 41
<212> TYPE: DNA
<213> ORGANISM: Artificial Sequence
<220> FEATURE:
<223> OTHER INFORMATION: Synthetic Construct

<400> SEQUENCE: 95
acacaactgg ggatccacca tgcacgtcca gtctctcctt g          41

<210> SEQ ID NO 96
<211> LENGTH: 40
<212> TYPE: DNA
<213> ORGANISM: Artificial Sequence
<220> FEATURE:
<223> OTHER INFORMATION: Synthetic Construct

<400> SEQUENCE: 96
gtcaccctct agatctttac aggcactgcg agtaccagtc            40

<210> SEQ ID NO 97
<211> LENGTH: 40
<212> TYPE: DNA
<213> ORGANISM: Artificial Sequence
<220> FEATURE:
<223> OTHER INFORMATION: Synthetic Construct

<400> SEQUENCE: 97
acacaactgg ggatccacca tgccaccacc actactggcc            40

<210> SEQ ID NO 98
<211> LENGTH: 41
<212> TYPE: DNA
<213> ORGANISM: Artificial Sequence
<220> FEATURE:
<223> OTHER INFORMATION: Synthetic Construct

<400> SEQUENCE: 98
gtcaccctct agatcttcat ggcctaccca tctcaaatct t          41

<210> SEQ ID NO 99
<211> LENGTH: 41
<212> TYPE: DNA
<213> ORGANISM: Artificial Sequence
<220> FEATURE:
<223> OTHER INFORMATION: Synthetic Construct

<400> SEQUENCE: 99
acacaactgg ggatccacca tgaagtccct gacctacgcc g          41

<210> SEQ ID NO 100
<211> LENGTH: 43
<212> TYPE: DNA
<213> ORGANISM: Artificial Sequence
<220> FEATURE:
<223> OTHER INFORMATION: Synthetic Construct

<400> SEQUENCE: 100
gtcaccctct agatctttac acgcactgag agtaccactg gtt        43

```
<210> SEQ ID NO 101
<211> LENGTH: 38
<212> TYPE: DNA
<213> ORGANISM: Artificial Sequence
<220> FEATURE:
<223> OTHER INFORMATION: Synthetic Construct

<400> SEQUENCE: 101
acacaactgg ggatccacca tgaagctcct cctccccg                              38

<210> SEQ ID NO 102
<211> LENGTH: 41
<212> TYPE: DNA
<213> ORGANISM: Artificial Sequence
<220> FEATURE:
<223> OTHER INFORMATION: Synthetic Construct

<400> SEQUENCE: 102
gtcaccctct agatcttcac gaggttgata tggagttgct c                          41

<210> SEQ ID NO 103
<211> LENGTH: 42
<212> TYPE: DNA
<213> ORGANISM: Artificial Sequence
<220> FEATURE:
<223> OTHER INFORMATION: Synthetic Construct

<400> SEQUENCE: 103
acacaactgg ggatccacca tgcgttctgt ttcccttctt gc                         42

<210> SEQ ID NO 104
<211> LENGTH: 37
<212> TYPE: DNA
<213> ORGANISM: Artificial Sequence
<220> FEATURE:
<223> OTHER INFORMATION: Synthetic Construct

<400> SEQUENCE: 104
gtcaccctct agatctttaa aaatcgcgcg ggtgttt                               37

<210> SEQ ID NO 105
<211> LENGTH: 38
<212> TYPE: DNA
<213> ORGANISM: Artificial Sequence
<220> FEATURE:
<223> OTHER INFORMATION: Synthetic Construct

<400> SEQUENCE: 105
acacaactgg ggatccacca tgttcttccg caacgccg                              38

<210> SEQ ID NO 106
<211> LENGTH: 36
<212> TYPE: DNA
<213> ORGANISM: Artificial Sequence
<220> FEATURE:
<223> OTHER INFORMATION: Synthetic Construct

<400> SEQUENCE: 106
gtcaccctct agatcttcaa gccttgggct cctcac                                36

<210> SEQ ID NO 107
<211> LENGTH: 38
<212> TYPE: DNA
<213> ORGANISM: Artificial Sequence
<220> FEATURE:
<223> OTHER INFORMATION: Synthetic Construct
```

```
<400> SEQUENCE: 107
acacaactgg ggatccacca tggctcatcc atgggcac                               38

<210> SEQ ID NO 108
<211> LENGTH: 43
<212> TYPE: DNA
<213> ORGANISM: Artificial Sequence
<220> FEATURE:
<223> OTHER INFORMATION: Synthetic Construct

<400> SEQUENCE: 108
gtcaccctct agatcttcac ttgtaccggt agagataagc acc                         43
```